(12) United States Patent
Kleymann et al.

(10) Patent No.: US 11,278,534 B2
(45) Date of Patent: *Mar. 22, 2022

(54) ENANTIOMERS OF SUBSTITUTED THIAZOLES AS ANTIVIRAL COMPOUNDS

(71) Applicant: Innovative Molecules GmbH, Munich (DE)

(72) Inventors: Gerald Kleymann, Bad Salzuflen (DE); Christian Gege, Ehingen (DE)

(73) Assignee: Innovative Molecules GmbG, Munich (DE)

( * ) Notice: Subject to any disclaimer, the term of this patent is extended or adjusted under 35 U.S.C. 154(b) by 38 days.

This patent is subject to a terminal disclaimer.

(21) Appl. No.: 16/753,814

(22) PCT Filed: Oct. 4, 2018

(86) PCT No.: PCT/EP2018/077022
§ 371 (c)(1),
(2) Date: Apr. 6, 2020

(87) PCT Pub. No.: WO2019/068817
PCT Pub. Date: Apr. 11, 2019

(65) Prior Publication Data
US 2020/0289486 A1    Sep. 17, 2020

(30) Foreign Application Priority Data

Oct. 5, 2017 (EP) ..................... 17195047

(51) Int. Cl.
*A61K 31/425* (2006.01)
*A61K 31/44* (2006.01)
(Continued)

(52) U.S. Cl.
CPC ........ *A61K 31/4439* (2013.01); *A61K 31/426* (2013.01); *A61K 45/06* (2013.01);
(Continued)

(58) Field of Classification Search
CPC ........ A61P 31/22; A61P 31/12; A61K 31/427; A61K 31/4439
(Continued)

(56) References Cited

U.S. PATENT DOCUMENTS 6,150,385 A    11/2000    Thaisrivongs et al.
6,458,959 B1   10/2002    Crute et al.
(Continued)

FOREIGN PATENT DOCUMENTS

DE    19959958 A1    8/2001
DE    10039265 A1    2/2002
(Continued)

OTHER PUBLICATIONS

James "Helicase-Primase as a target of new therapies for herpes simplex virus infections," Clinical Pharmacology & Therapeutics, 2015, vol. 97, No. 1, pp. 66-78 (Year: 2015).*
(Continued)

*Primary Examiner* — Shengjun Wang
(74) *Attorney, Agent, or Firm* — Rankin, Hill & Clark LLP; Christopher Jan Korff

(57) ABSTRACT

The present invention relates to novel antiviral compounds with specific stereoconfiguration, especially to specific novel enantiomers, to a process for their preparation and to their use as medicaments, in particular as antiviral medicaments.

19 Claims, 16 Drawing Sheets

Specification includes a Sequence Listing.

(51) Int. Cl.

| | | |
|---|---|---|
| *C07D 277/00* | (2006.01) | |
| *A61K 31/4439* | (2006.01) | |
| *A61P 31/22* | (2006.01) | |
| *A61K 31/426* | (2006.01) | |
| *A61K 45/06* | (2006.01) | |
| *C07D 277/46* | (2006.01) | |
| *C07D 417/12* | (2006.01) | |

(52) U.S. Cl.
CPC ............ *A61P 31/22* (2018.01); *C07D 277/46* (2013.01); *C07D 417/12* (2013.01)

(58) Field of Classification Search
USPC ........................................ 514/369, 370, 342
See application file for complete search history.

(56) References Cited

U.S. PATENT DOCUMENTS

| | | |
|---|---|---|
| 6,500,817 B1 | 12/2002 | Fischer et al. |
| 7,105,553 B2 | 9/2006 | Fischer et al. |
| 7,883,713 B2 | 2/2011 | Betz et al. |
| 8,759,335 B2 | 6/2014 | Hadida Ruah et al. |
| 8,784,887 B2 | 7/2014 | Laich et al. |
| 10,590,094 B2 | 3/2020 | Kleymann et al. |
| 2002/0119995 A1 | 8/2002 | Hendrix et al. |
| 2002/0160932 A1 | 10/2002 | Kleymann et al. |
| 2004/0235916 A1 | 11/2004 | Schohe-Loop et al. |
| 2007/0004735 A1 | 1/2007 | Betz et al. |

FOREIGN PATENT DOCUMENTS

| | | |
|---|---|---|
| DE | 10044328 A1 | 3/2002 |
| DE | 10044358 A1 | 3/2002 |
| DE | 10129716 A1 | 1/2003 |
| DE | 10129717 A1 | 1/2003 |
| DE | 10210319 A1 | 9/2003 |
| EP | 2 101 640 B1 | 5/2013 |
| EP | 2 602 258 B1 | 3/2014 |
| WO | 99/24416 A1 | 5/1999 |
| WO | 99/42455 | 8/1999 |
| WO | 00/76966 A2 | 12/2000 |
| WO | 01/47904 A1 | 7/2001 |
| WO | 01/96874 A1 | 12/2001 |
| WO | 03/007946 A1 | 1/2003 |
| WO | 2004/015416 A2 | 2/2004 |
| WO | 2012/061190 A1 | 5/2012 |
| WO | 2012/160034 A1 | 11/2012 |
| WO | 2017/174640 A1 | 10/2017 |

OTHER PUBLICATIONS

Espacenet bibliographic data for DE10039265 published Feb. 21, 2002, two pages.
Espacenet bibliographic data for DE10044328 published Mar. 21, 2002, two pages.
Espacenet bibliographic data for DE10044358 published Mar. 21, 2002, two pages.
Espacenet bibliograhic data for DE10129716 published Jan. 2, 2003, two pages.
Espacenet bibliographic data for DE10129717 published Jan. 2, 2003, two pages.
Espacenet bibliographic data for DE10210319 published Sep. 18, 2003, two pages.
Espacenet bibliographic data for DE19959958 published Aug. 30, 2001, two pages.
Espacenet bibliographic data for WO 00/76966 published Dec. 21, 2000, two pages.
Espacenet bibliographic data for WO 2004015416 published Feb. 19, 2004, one page.
Espacenet bibliographic data for WO 03007946 published Jan. 30, 2003, two pages.
International Search Report for corresponding PCT/EP2017/058077 dated Jul. 24, 2017, four pages.
Ziegler, et al., "2-Aminothiazolesulfonamides" J. Org. Chem. vol. 25, pp. 1454-1455, 1960.
Yer, et al., "Inhibition Profiling of Human Carbonic Anhydrase II by High-Throughput Screening of Structurally Diverse, Biologically Active Compounds", J. Biomol. Screen., vol. 11, pp. 782-791, 2006.
Katritzky, et al. "Synthesis and Physicochemical Properties of Thiadiazolo [3,2-a] pyrimidlinesulfonamides and Thiadiazolo [3,2-a] triazinesulfonamides as Candidates for Topically Effective Carbonic Anhydrase Inhibitors", J. Med. Chem., vol. 30, pp. 2058-2062, 1987.
Lucking, "Sulfoximines: A neglected Opportunity in Medicinal Chemistry" Angew. Chem. Int. Ed., vol. 52, pp. 9399-9408, 2013.
Harder, et al., "Efficient Stacking on Protein Amide Fragments", ChemMedChem vol. 8, pp. 397-404, 2013.
Park, et al., "N-Cyano Sulfoxximines: COX Inhibition, Anticancer Activity, Cellular Toxicity, and Mutagenicity", ChemMedChem, vol. 8, pp. 217-220, 2013.
Durand-Cavagna, et al., "Urothelial Hyperplasia Induced by Carbonic Anhydrase Inhibitors (CAIs) in Animals and It's Relationship to Urinary Na and pH", Fund. Appl. Toxicol. vol. 18, pp. 137-143 1992.
Lipinski, et al., "Experimental and computational approaches to estimate solubility and permeability in drug discovery and development settings", Adv. Drug Del. Rev., vol. 46 No 3, pp. 3-25, 1997.
Kleymann, et al. "A Generally Applicable, High-Throughput Screening-Compatible Assay to Identify, Evaluate, and Optimize Antimicrobial Agents for Drug Therapy", J. Biomol. Screen., vol. 9 No 7, pp. 578-587, 2004.
Betz, et al. "Potent In Vivo Antiviral Activity of the Herpes Simplex Virus Primase-Helicase Inhibitor BAY 57-1293", Antimicrob. Agents Chemother., vol. 46 No 6, pp. 1766-1772, 2002.
Kleymann et al., "New helicase-primase inhibitors as drug candidates for the treatment of herpes simplex disease", Nat Med., vol. 8, pp. 392-398, 2002.
International Search Report for corresponding PCT/EP2018/077022 dated Dec. 3, 2018, seven pages.
U.S. Appl. No. 16/747,061, filed Jan. 20, 2020.
N. Uhlig et al. Antiviral Research "Helicase primase inhibitors (HPIs) are efficacious for therapy of human herpes simplex virus (HSV) disease in an infection mouse model", Antiviral Research, pp. 1-9 (2021), available online Oct. 16, 2021.
Goldberg, et al., "General synthetic strategies towards N-alkyl sulfoximine building blocks for medicinal chemistry and the use of dimethylsulfoximine as a versatile precursor", Tetrahedron, vol. 70, pp. 6613-6622 (2014).
Lücking, et al., "The Lab Oddity Prevails: Discovery of Pan-CDK Inhibitor (R)-S-Cyclopropyl-S-(4-{[4-{[(1R,2R)-2-hydroxymethylproply]oxy}-5-(trifluoromethyl)pyrimidin-2-yl]amino}phenyl)sulfoximide (BAY 1000394) for the Treatment of Cancer", ChemMedChem, vol. 8, pp. 1067-1085 (2013).
Kaufman et al., "Efficacy of a Helicase-Primase Inhibitor in Animal Models Of Ocular Herpes Simplex Virus Type 1 Infection", Journal of Ocular Pharmacology And Therapeutics, vol. 24, No. 1, pp. 34-42 (2008).
Scott, et al., "Circumventing Seizure Activity in a Series of G Protein Coupled Receptor 119 (GPR119) Agonists", Journal of Medicinal Chemistry, vol. 57, pp. 8984-8998 (2014).
Indian Examination Report for corresponding Indian Application No. 202017010464, dated Oct. 12, 2021, 9 pages.

* cited by examiner

ENANTIOMERS OF SUBSTITUTED THIAZOLES AS ANTIVIRAL COMPOUNDS

SUMMARY OF THE INVENTION

The present invention relates to novel antiviral compounds with specific stereoconfiguration, especially to specific novel enantiomers, to a process for their preparation and to their use as medicaments, in particular as antiviral medicaments.

INTRODUCTION

The pandemic of viral infections has plagued humanity since ancient times, causing muco-cutaneous infection such as herpes labialis and herpes genitalis. Disease symptoms often interfere with everyday activities and occasionally HSV infections are the cause of life-threatening (encephalitis) or sight-impairing disease (keratitis), especially in neonates, elderly and the immunocompromised patient population such as transplant or cancer patients or patients with an inherited immunodeficiency syndrome or disease. After infection the alpha herpesviridae persist for life in neurons of the host in a latent form, periodically reactivating and often resulting in significant psychosocial distress for the patient. Currently no cure is available.

So far, vaccines, interleukins, interferones, therapeutic proteins, antibodies, immunomodulators and small-molecule drugs with specific or non-specific modes of action either lacked efficacy or the required safety profile to replace the nucleosidic drugs acyclovir, valacyclovir and famciclovir as the first choice of treatment.

The known thiazolylamides are the most potent drugs in development today. These antiviral agents act by a novel mechanism of action and display low resistance rates in vitro and superior efficacy in animal models compared to nucleosidic drugs, however, development is hampered by off target carbonic anhydrase activity and an unusual pharmacokinetic profile.

This patent application discloses new antiviral compounds lacking (or at least with significantly reduced) carbonic anhydrase activity, showing an improved solubility and a suitable pharmacokinetic profile for use as a medicament.

SEQUENCE LISTING

The instant application contains a Sequence Listing which has been submitted electronically in ASCII format and is hereby incorporated by reference in its entirety. Said ASCII copy, created on Mar. 11, 2020, is named GIL-47584-Listing.txt and is 4,096 bytes in size.

PRIOR ART

2-Aminothiazol-5-sulfonamides are known from the publication C. Ziegler et al., *J. Org. Chem.* 1960:25, 1454. Moreover, the German Offenlegungsschrift 2101640 describes N-thiazol-2-yl-amides and -ureas having herbicidal action.

WO97/24343 relates to phenylthiazole derivates having anti-herpes virus properties.

WO99/42455 likewise relates to phenylthiazole derivates having anti-herpes virus properties.

WO99/47507 relates to 1,3,4-thiadiazoles derivates having anti-herpes virus properties.

WO0147904 (A1) and the corresponding US2004/0006076 relate to thiazolyl amides having anti-herpes virus properties.

WO2003/000259 relates to topical application of thiazolyl amides.

WO2004060860 (A2) relates to a method for inhibiting the replication of herpes viruses.

WO0220014 (A1) relates to incompetitive inhibitors of helicase-primase.

WO0212211 (A1) relates to inverse thiazolylamide derivatives.

WO0053591 (A1) relates to thiazolyl urea derivatives and their utilization as antiviral agents.

WO03000260 (A1) relates to thiazolyl amides and their use as antiviral drugs.

WO0196874 (A1) and EP1319185 (A1) relate to a method for identifying compounds with anti-herpes activity.

WO2004015416 relates to methods for the identification of agents with anti-microbial action.

WO03007946 relates to secondary 1,3-thiazole-5-yl sulfonamide derivatives and their use as antiviral agents.

WO0076966 relates to indolinylamide derivatives.

DE19959958 relates to new 2-ureido-thiazole-5-sulfonic acid amide derivatives useful as antiviral agents, especially against herpes simplex infections.

DE10210319 relates to new thiazole-5-sulfonamide derivatives, useful for the treatment of viral infections in humans and animals, especially herpes simplex or human cytomegalovirus infections.

DE10129717 relates to a combination preparation containing nucleoside compound and 5-sulfonyl-2-phenylacetamido-thiazole derivative, useful as antiviral agent effective against herpes viruses, especially herpes simplex.

DE10129716 relates to a combination preparation useful as antiviral agent effective against herpes viruses, especially herpes simplex, contains acetylsalicylic acid and 5-sulfonyl-2-phenylacetamido-thiazole derivative.

DE10044358 relates to new thiazole-5-sulfonamide derivatives useful as antiviral agents, especially for control of herpes simplex infections.

DE10044328 relates to new thiazole-5-sulfonamide derivatives useful as antiviral agents, especially for control of herpes simplex infections.

DE10039265 relates to new 2-acylamino-5-aminosulfonyl-1,3-thiazole derivatives, useful as antiviral agents, especially for treatment or prophylaxis of herpes simplex virus infections.

HRP20140352 relates to N-[5-aminosulfonyl)-4-methyl-1,3-thiazol-2-yl]-N-methyl-2-[4-(2-pyridinyl)phenyl]acetamide mesylate monohydrate.

WO2006103011 and EP1865921 relate to a pharmaceutical preparation of N-[5-(aminosulfonyl)-4-methyl-1,3-thiazol-2-yl]-N-methyl-2-[4-(2-pyridinyl)phenyl]acetamide.

WO2005075435 relates to compounds being ATP-binding cassette transporter modulators useful in the treatment of i.a. cystic fibrosis and Alzheimer's disease.

WO2018095576, WO2018096170 and WO2018096177 describe topical pharmaceutical formulations of pritelivir salts or free bases and new polymorphs of pritelivir (e.g. free base hemihydrate or maleate salt).

WO2018127207 relates to other thiazole-5-sulfonamide derivatives.

However, none of said prior art documents covers aminosulfonimidoyl, methylsulfonimidoyl, cyclopropylsulfonimidoyl or N-cyano-S-methyl-sulfonimidoyl derivatives of the thiazolylacet-amide series.

The unpublished international application PCT/EP2017/058077 describes novel antiviral compounds of the general Formula (I)

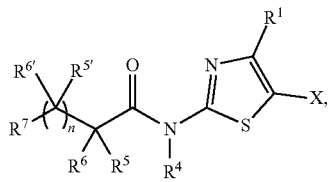

(I)

wherein X may have the meaning of

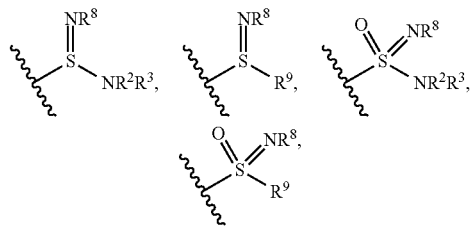

with the substituent definitions provided therein, however, without disclosing any specific stereoisomer or a specific stereoconfiguration of any specific compound disclosed therein.

The present invention now discloses novel antiviral compounds with specific stereoconfiguration according to Formula (Ia) and (Ib) as described herein, specific novel enantiomers, as well as surprisingly superior characteristics thereof, and further provides a process for the preparation thereof from a mixture of stereoisomers of the general Formula (I) as described herein.

Moreover, similar as the mixture comprising the stereoisomers of the compounds of the present invention, also the novel isolated enantiomers show no or at least significantly reduced off target carbonic anhydrase activity at increased solubility and have been found to act more actively for treating viral infections, such as in particular herpes simplex viruses.

Even more surprisingly the enantiomers with a specific optical rotation counterclockwise, levo or negative rotation in a polarimeter or CD spectra eluting first from a defined chiral HPLC column are at least a factor of 2 more potent in vitro than the respective enantiomers showing a clockwise, dextro or positive optical rotation in a polarimeter eluting last from a defined chiral HPLC column.

Surprisingly the enantiomers with a negative specific rotation show higher exposures in the pharmacokinetic profile compared to the respective mixture of stereoisomers or the racemate or the respective enantiomer with a positive specific rotation.

The optimised pharmacokinetic profile of selected stereoisomers leads to a profound antiviral activity in treated mammals suitable for clinical development in humans and use as a medicament.

DETAILED DESCRIPTION OF THE INVENTION

The present invention relates to antiviral compounds with specific stereoconfiguration according to the formula

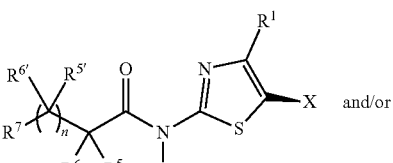

(Ia)

and/or

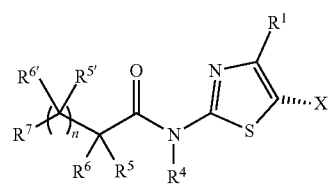

(Ib)

an enantiomer, diastereomer, tautomer, N-oxide, solvate, formulation and pharmaceutically acceptable salt thereof, wherein in Formula (Ia) and (Ib)
X is selected from

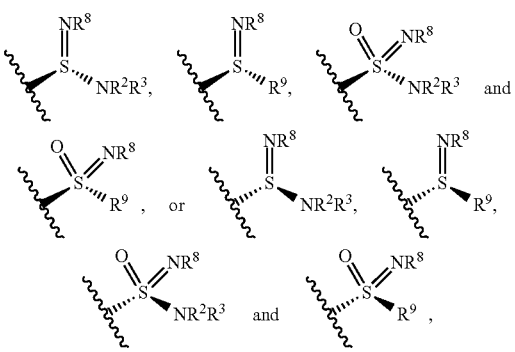

respectively;

$R^1$ is selected from H, halogen, $C_{1-6}$-alkyl, halo-$C_{1-6}$-alkyl, hydroxy-$C_{1-6}$-alkyl, $C_{3-6}$-cycloalkyl, halo-$C_{3-6}$-cycloalkyl, —O—$C_{1-6}$-alkyl, —O-halo-$C_{1-6}$-alkyl and —NH—$C_{1-6}$-alkyl;

$R^2$ is selected from H, —CN, —NO$_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$R$^{13}$, $C_{0-10}$-alkylene-SO$_3$R$^{11}$, $C_{0-10}$-alkylene-SO$_2$NR$^{11}$R$^{12}$, $C_{0-10}$-alkylene-NR$^{11}$C(=O)R$^{11}$, $C_{0-10}$-alkylene-NR$^{11}$C(=S)R$^{11}$, $C_{0-10}$-alkylene-NR$^{11}$SO$_2$R$^{13}$, $C_{0-10}$-alkylene-NR$^{11}$C(=O)NR$^{11}$R$^{12}$, $C_{0-10}$-alkylene-NR$^{11}$C(=S)NR$^{11}$R$^{12}$, $C_{0-10}$-alkylene-NR$^{11}$SO$_2$NR$^{11}$R$^{12}$, $C_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, NR$^{11}$SO$_2$R$^{13}$, $NR^{11}C(=O)NR^{11}R^{12}$, $NR^{11}SO_2NR^{11}R^{12}$, $C_{3-10}$-cycloalkyl, $O-C_{3-10}$-cycloalkyl, $C_{3-10}$-heterocycloalkyl, $O-C_{3-10}$-heterocycloalkyl and $NR^{11}R^{12}$;

$R^3$ is selected from H, $C_{1-6}$-alkyl, halo-$C_{1-6}$-alkyl, $-O-C_{1-6}$-alkyl, $-O$-halo-$C_{1-6}$-alkyl, $C_{3-6}$-cycloalkyl and $C_{3-6}$-heterocycloalkyl, wherein alkyl, cycloalkyl and heterocycloalkyl are optionally substituted with 1 to 5 substituents independently selected from halogen, $-CN$, OH, oxo, $C_{1-3}$-alkyl, halo-$C_{1-3}$-alkyl, $O-C_{1-3}$-alkyl, $O$-halo-$C_{1-3}$-alkyl, $SO_2-C_{1-3}$-alkyl, $CO_2H$;

or $R^2$ and $R^3$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, $-CN$, $-NO_2$, OH, oxo, $C_{1-3}$-alkyl, halo-$C_{1-3}$-alkyl, $O-C_{1-3}$-alkyl, $O$-halo-$C_{1-3}$-alkyl, $SO_2-C_{1-3}$-alkyl, $CO_2H$;

$R^4$ is selected from H, $C_{1-6}$-alkyl, $C_{1-6}$-acyl, $C_{2-6}$-alkenyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, $-CN$, OH, oxo, $C_{1-3}$-alkyl, halo-$C_{1-3}$-alkyl, $O-C_{1-3}$-alkyl, O-halo-$C_{1-3}$-alkyl;

$R^5$ and $R^6$ and $R^{5'}$ and $R^{6'}$ are independently selected from H, halogen, $C_{1-6}$-alkyl, $NH_2$, $NHC_{1-6}$-alkyl, $N(C_{1-6}$-alkyl$)_2$, $C_{0-6}$-alkylene-$C(=O)NH_2$;

or $R^5$ and $R^6$ and $R^{5'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, $-CN$, $-NO_2$, OH, oxo, $C_{1-3}$-alkyl, halo-$C_{1-3}$-alkyl, $O-C_{1-3}$-alkyl, O-halo-$C_{1-3}$-alkyl, $SO_2-C_{1-3}$-alkyl, $CO_2H$;

or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, $-CN$, $-NO_2$, OH, oxo, $C_{1-3}$-alkyl, halo-$C_{1-3}$-alkyl, $O-C_{1-3}$-alkyl, O-halo-$C_{1-3}$-alkyl, $SO_2-C_{1-3}$-alkyl, $CO_2H$;

$R^7$ is selected from a 6-membered aryl and 5- or 6-membered heteroaryl, wherein aryl and heteroaryl are optionally substituted with 1 to 4 substituents independently selected from halogen, $-CN$, $-NO_2$, OH, $C_{1-6}$-alkyl, $O-C_{1-6}$-alkyl, $C_{3-6}$-cycloalkyl, $O-C_{3-6}$-cycloalkyl, $C_{3-6}$-heterocycloalkyl, $O-C_{3-6}$-heterocycloalkyl, $SO_y-C_{1-6}$-alkyl, $CO_2H$, $C(=O)O-C_{1-6}$-alkyl, 6- to 10-membered aryl, 5- or 10-membered heteroaryl, O-(6- to 10-membered aryl) and O-(5- or 10-membered heteroaryl), wherein alkyl, cycloalkyl, heterocycloalkyl, aryl and heteroaryl are optionally substituted with 1 to 5 substituents independently selected from halogen, $-CN$, $-NO_2$, OH, $R^{13}$, $OR^{13}$, $CO_2R^{11}$, $NR^{11}R^{12}$, $C(=O)R^{11}$, $C(=S)R^{11}$, $C(=O)NR^{11}R^{12}$, $NR^{11}C(=O)NR^{11}R^{12}$, $NR^{11}C(=O)OR^{13}$, $OC(=O)NR^{11}R^{12}$, $C(=S)NR^{11}R^{12}$, $NR^{11}C(=S)NR^{11}R^{12}$, $NR^{11}C(=S)OR^{13}$, $OC(=S)NR^{11}R^{12}$; $SO_y-C_{1-6}$-alkyl, $SO_y$-halo-$C_{1-6}$-alkyl, $SR^{11}$, $SO_xR^{13}$, $SO_3R^{11}$, $SO_2NR^{11}R^{12}$, $NR^{11}SO_2R^{13}$, $NR^{11}SO_2NR^{11}R^{12}$;

$R^8$ is selected from H, $-CN$, $-NO_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5 to 10-membered heteroaryl), $C_{0-10}$-alkylene-(6 to 10-membered aryl), $C_{0-10}$-alkylene-(6 to 10-membered heteroaryl), $C_{0-10}$-alkylene-$OR^{11}$, $C_{0-10}$-alkylene-$CO_2R^{11}$, $C_{0-10}$-alkylene-$C(=O)NR^{11}R^{12}$, $C_{0-10}$-alkylene-$C(=S)NR^{11}R^{12}$, $C_{0-10}-O$-alkylene-$C(=O)NR^{11}SO_2R^{13}$, $C_{0-10}$-alkylene-$C(=S)NR^{11}SO_2R^{11}$, $C_{0-10}$-alkylene-$C(=O)R^{11}$, $C_{0-10}$-alkylene-$C(=S)R^{11}$, $C_{0-10}$-alkylene-$SR^{11}$, $C_{0-10}$-alkylene-$SO_x-R^{13}$, $C_{0-10}$-alkylene-$SO_3R^{11}$, $C_{0-10}$-alkylene-$SO_2NR^{11}R^{12}$, $C_{0-10}$-alkylene-$NR^{11}C(=O)R^{11}$, $C_{0-10}$-alkylene-$NR^{11}C(=S)R^{11}$, $C_{0-10}$-alkylene-$NR^{11}SO_2R^{11}$, $C_{0-10}$-alkylene-$NR^{11C}(=O)NR^{11}R^{12}$, $C_{0-10}$-alkylene-$NR^{11C}(=S)NR^{11}R^{12}$, $C_{0-10}$-alkylene-$NR^{11}-SO_2-NR^{11}R^{12}$, $C_{0-10}$-alkylene-$NR^{11}R^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $-NO_2$, $OR^{11}$, $O-C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $PO(OH)_2$, $SO_2NR^{11}R^{12}$, $NR^{11}COR^{11}$, $NR^{11}SO_2R^{11}$, $NR^{11}-CO-NR^{11}R^{12}$, $NR^{11}-SO_2-NR^{11}R^{12}$, $C_{3-10}$-cycloalkyl, $O-C_{3-10}$-cycloalkyl, $C_{3-10}$-heterocycloalkyl, $O-C_{3-10}$-heterocycloalkyl and $NR^{11}R^{12}$;

$R^9$ is selected from $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-$OR^{11}$, $C_{0-10}$-alkylene-$CO_2R^{11}$, $C_{0-10}$-alkylene-$C(=O)NR^{11}R^{12}$, $C_{0-10}$-alkylene-$C(=S)NR^{11}R^{12}$, $C_{0-10}-O$-alkylene-$C(=O)NR^{11}SO_2R^{13}$, $C_{0-10}$-alkylene-$C(=S)NR^{11}SO_2R^{11}$, $C_{0-10}$-alkylene-$C(=O)R^{11}$, $C_{0-10}$-alkylene-$C(=S)R^{11}$, $C_{0-10}$-alkylene-$SR^{11}$, $C_{0-10}$-alkylene-$SO_xR^{13}$, $C_{0-10}$-alkylene-$SO_3R^{11}$, $C_{0-10}$-alkylene-$SO_2NR^{11}R^{12}$, $C_{0-10}$-alkylene-$NR^{11}C(=O)R^{11}$, $C_{0-10}$-alkylene-$NR^{11}C(=S)R^{11}$, $C_{0-10}$-alkylene-$NR^{11}SO_2R^{13}$, $C_{0-10}$-alkylene-$NR^{11}C(=O)NR^{11}R^{12}$, $C_{0-10}$-alkylene-$NR^{11}C(=S)NR^{11}R^{12}$, $C_{0-10}$-alkylene-$NR^{11}SO_2NR^{11}R^{12}$, $C_{0-10}$-alkylene-$NR^{11}R^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $-NO_2$, $OR^{11}$, $O-C_{2-6}$-alkylene-$OR^{11}$, $C_{1-6}$-alkyl, halo-$C_{1-6}$-alkyl, halogen, $CO_2R^{11}$, $C(=O)NR^{11}R^{12}$, $C(=O)NR^{11}SO_2R^{11}$, $C(=O)R^{11}$, $SR^{11}$, $SO_xR^{11}$, $SO_3R^{11}$, $P(=O)(OR^{11})_2$, $SO_2NR^{11}R^{12}$, $NR^{11}C(=O)R^{11}$, $NR^{11}SO_2R^{13}$, $NR^{11}C(=O)NR^{11}R^{12}$, $NR^{11}SO_2NR^{11}R^{12}$, $C_{3-10}$-cycloalkyl, $O-C_{3-10}$-cycloalkyl, $C_{3-10}$-heterocycloalkyl, $O-C_{3-10}$-heterocycloalkyl and $NR^{11}R^{12}$;

$R^{11}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents independently selected from the group consisting of halogen, $-CN$, OH, oxo, $C_{1-3}$-alkyl, halo-$C_{1-3}$-alkyl, $O-C_{1-3}$-alkyl, O-halo-$C_{1-3}$-alkyl, $NH_2$, $NH(C_{1-3}$-alkyl), $N(C_{1-3}$-alkyl$)_2$, $C_{3-6}$-heterocycloalkyl, $C_{3-6}$-cycloalkyl, $SO_2-NHC_{1-3}$-alkyl, $SO_2-N(C_{1-3}$-alkyl$)_2$ and $SO_2-C_{1-3}$-alkyl, wherein cycloalkyl and heterocycloalkyl is unsubstituted or substituted with 1 to 3 substituents independently selected from the group consisting of F, OH, oxo, $CH_3$, $CHF_2$ and $CF_3$;

$R^{12}$ is independently selected from H, $C_{1-6}$-alkyl, halo-$C_{1-6}$-alkyl and $C_{3-6}$-cycloalkyl;

or $R^{11}$ and $R^{12}$ when taken together with the nitrogen to which they are attached complete a 3-to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;

$R^{13}$ is independently selected from $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents independently selected from the group consisting of halogen, —CN, OH, oxo, $C_{1-3}$-alkyl, halo-$C_{1-3}$-alkyl, O—$C_{1-3}$-alkyl, O-halo-$C_{1-3}$-alkyl, NH$_2$, NH($C_{1-3}$-alkyl), N($C_{1-3}$-alkyl)$_2$, $C_{3-6}$-heterocycloalkyl, $C_{3-6}$-cycloalkyl, $C_{3-6}$-alkyl, SO$_2$—NHC$_{1-3}$-alkyl, SO$_2$—N($C_{1-3}$-alkyl)$_2$ and SO$_2$—$C_{1-3}$-alkyl, wherein cycloalkyl and heterocycloalkyl is unsubstituted or substituted with 1 to 3 substituents independently selected from the group consisting of F, OH, oxo, CH$_3$, CHF$_2$ and CF$_3$;

n is selected from 0 and 1;

x is independently selected from 1 and 2;

y is independently selected from 0, 1 and 2;

and wherein optionally $R^1$ is connected to one residue selected from $R^2$, $R^3$, $R^8$, $R^9$ or $R^{12}$ to form a 5 to 8-membered heterocycle, which is optionally substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H.

In the context of the present invention "$C_{1-10}$-alkyl" means a saturated alkyl chain having 1 to 10 carbon atoms which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl and decyl. Preferred is "$C_{1-6}$-alkyl", more preferred is "$C_{1-4}$-alkyl", most preferred is "$C_{1-3}$-alkyl".

The term "halo-$C_{1-10}$-alkyl" or "halo-$C_{1-6}$-alkyl", respectively, means that one or more hydrogen atoms in the alkyl chain are replaced by a halogen, as defined below. A preferred example thereof is the formation of a —CF$_3$ group.

The term "hydroxy-$C_{1-6}$-alkyl" means that one or more hydrogen atoms in the alkyl chain, as defined above, are replaced by a hydroxyl group (—OH). Examples thereof include hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl etc. A preferred example thereof is hydroxymethyl (—CH$_2$OH).

"$C_{2-10}$-alkenyl" means an alkyl chain having 1 to 10 carbon atoms which may be straight chained or branched, containing at least one carbon to carbon double bond. Examples thereof include ethenyl, propenyl, decenyl, 2-methylenehexyl and (2E,4E)-hexa-2,4-dienyl. Preferred is "$C_{2-6}$-alkenyl".

"$C_{2-10}$-alkynyl" means an alkyl chain having 1 to 10 carbon atoms which may be straight chained or branched, containing at least one carbon to carbon triple bond. Examples thereof include ethynyl, propynyl and decynyl. Preferred is "$C_{2-6}$-alkynyl".

A "$C_{0-10}$-alkylene" means that the respective group is divalent and connects the attached residue with the remaining part of the molecule. Moreover, in the context of the present invention, "$C_0$-alkylene" is meant to be represent a bond. Preferred is "$C_{0-6}$-alkylene".

A $C_{3-10}$-cycloalkyl group or $C_{3-10}$-carbocycle means a saturated or partially unsaturated mono-, bi-, spiro- or multicyclic ring system comprising 3 to 10 carbon atoms. Examples include cyclopropyl, cyclobutyl, cyclopentyl, cyclohexyl, cyclohexenyl, bicyclo[2.2.2]octyl, bicyclo[2.2.1]heptyl, adamantyl and pentacyclo[4.2.0.0$^{2,5}$.0$^{3,8}$.0$^{4,7}$]octyl. Preferred is a $C_{3-6}$-cycloalkyl group. More preferred is a cyclopropyl group.

A $C_{3-10}$-heterocycloalkyl group means a saturated or partially unsaturated 3 to 10 membered carbon mono-, bi-, spiro- or multicyclic ring wherein 1, 2 or 3 carbon atoms are replaced by 1, 2 or 3 heteroatoms, respectively, wherein the heteroatoms are independently selected from N, O, S, SO and SO$_2$. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected via a carbon or nitrogen atom. Preferred is a $C_{3-6}$-heterocycloalkyl group.

A 5- to 10-membered mono- or bicyclic heteroaromatic ring system (within the application also referred to as heteroaryl) containing up to 5 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. Preferred are 5- to 6-membered monocyclic heteroaromatic rings. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl and pyrazolo[1,5-a]pyrimidinyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

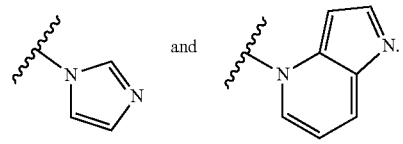 [SMILES: *n1ccnc1 ; *n1cccc2nccc1-2]

A 6- to 10-membered mono- or bicyclic aromatic ring system (within the application also referred to as aryl) means an aromatic carbon cycle such as phenyl or naphthalenyl. Preferred are 5- to 6-membered aromatic rings (aryl), such as in particular phenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with H$_2$O$_2$ or a peracid in an inert solvent.

Halogen is selected from fluorine, chlorine, bromine and iodine, preferred are fluorine and chlorine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

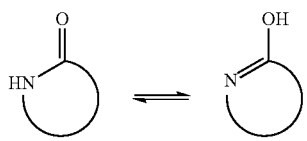

A $C_{3-10}$-cycloalkyl or $C_{3-10}$-heterocycloalkyl group can be connected straight or spirocyclic, e.g. when cyclohexane is substituted with the heterocycloalkyl group oxetane, the following structures are possible:

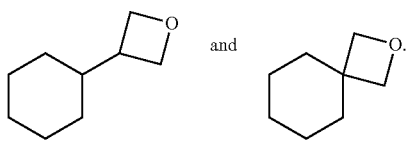 [SMILES: C1CCC(C2COC2)CC1 ; C1CCC2(CC1)COC2]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The optical rotation (depicted as (−) or (+) in the text) used in the compound name and Example number relates to the measured value at 365 nm, if not stated otherwise.

The compounds used or prepared in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Depending on the substitution pattern, the specific compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be separated into the stereoisomerically uniform components in a known manner.

The scope of the invention includes those compounds which are only converted into the actual active compounds of the Formulas (Ia), (Ib), (IIa) and (IIb) once inside the body (so-called prodrugs).

The invention relates in particular to the following embodiments:

A particularly preferred embodiment of the invention relates to compounds of the Formula (Ia) and/or (Ib) supra, wherein X is selected from

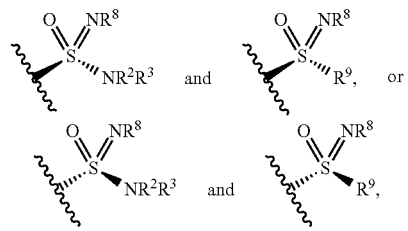

and wherein $R^1$, $R^2$, $R^3$, $R^4$, $R^5$, $R^6$, $R^{5'}$, $R^{6'}$, $R^7$, $R^8$, $R^9$, $R^{11}$, $R^{12}$, $R^{13}$, n, x and y have the meaning as defined in any of the embodiments described herein.

A further particularly preferred embodiment of the invention relates to compounds of the Formula (Ia) and/or (Ib) supra, wherein X is selected from

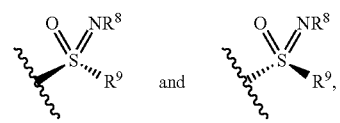

and wherein $R^1$, $R^2$, $R^3$, $R^4$, $R^5$, $R^6$, $R^{5'}$, $R^{6'}$ $R^7$, $R^8$, $R^9$, $R^{11}$, $R^{12}$, $R^{13}$, n, x and y have the meaning as defined in any of the embodiments described herein.

In an alternative preferred embodiment in combination with any of the above or below embodiments $R^1$ is selected from H, halogen, $C_{1-6}$-alkyl, halo-$C_{1-6}$-alkyl, hydroxy-$C_{1-6}$-alkyl, $C_{3-6}$-cycloalkyl, halo-$C_{3-6}$-cycloalkyl, —O—$C_{1-6}$-alkyl, —O-halo-$C_{1-6}$-alkyl and —NH—$C_{1-6}$-alkyl.

In a further preferred embodiment in combination with any of the above or below embodiments $R^1$ is selected from H, halogen, $C_{1-6}$-alkyl, halo-$C_{1-6}$-alkyl, $C_{3-6}$-cycloalkyl, halo-$C_{3-6}$-cycloalkyl, —O—$C_{1-6}$-alkyl, —O-halo-$C_{1-6}$-alkyl and —NH—$C_{1-6}$-alkyl.

In a further more preferred embodiment in combination with any of the above or below embodiments $R^1$ is $C_{1-6}$-alkyl or $C_{3-6}$-cycloalkyl.

In a further more preferred embodiment in combination with any of the above or below embodiments $R^1$ is methyl or cyclopropyl.

In an alternative preferred embodiment in combination with any of the above or below embodiments $R^2$ is selected from H, —CN, —NO$_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$R$^{13}$, $C_{0-10}$-alkylene-SO$_3$R$^{11}$, $C_{0-10}$-alkylene-SO$_2$NR$^{11}$R$^{12}$, $C_{0-10}$-alkylene-NR$^{11}$C(=O)R$^{11}$, $C_{0-10}$-alkylene-NR$^{11}$C(=S)R$^{11}$, $C_{0-10}$-alkylene-NR$^{11}$SO$_2$R$^{13}$, $C_{0-10}$-alkylene-NR$^{11}$C(=O)NR$^{11}$R$^{12}$, $C_{0-10}$-alkylene-NR$^{11}$C(=S)NR$^{11}$R$^{12}$, $C_{0-10}$-alkylene-NR$^{11}$SO$_2$NR$^{11}$R$^{12}$, $C_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, NR$^{11}$SO$_2$R$^{13}$ NR$^{11}$C(=O)NR$^{11}$R$^{12}$, NR$^{11}$SO$_2$NR$^{11}$R$^{12}$, $C_{3-10}$-cycloalkyl, O—$C_{3-10}$-cycloalkyl, $C_{3-10}$-heterocycloalkyl, O—$C_{3-10}$-heterocycloalkyl and NR$^{11}$R$^{12}$;

$R^3$ is selected from H, $C_{1-6}$-alkyl, halo-$C_{1-6}$-alkyl, —O—$C_{1-6}$-alkyl, —O-halo-$C_{1-6}$-alkyl, $C_{3-6}$-cycloalkyl and $C_{3-6}$-heterocycloalkyl, wherein alkyl, cycloalkyl and heterocycloalkyl are optionally substituted with 1 to 5 substituents independently selected from halogen, —CN, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;

or $R^2$ and $R^3$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H; and $R^{11}$, $R^{12}$, $R^{13}$ and x have the meaning as defined in any of the embodiments described herein.

In a further preferred embodiment in combination with any of the above or below embodiments $R^2$ and $R^3$ are independently selected from H or $C_{1-3}$-alkyl, or $R^2$ and $R^3$ when taken together with the nitrogen to which they are attached complete a 3- to 8-membered ring.

In a more preferred embodiment in combination with any of the above or below embodiments $R^2$ and $R^3$ are H.

In an alternative preferred embodiment in combination with any of the above or below embodiments $R^8$ is selected from H, —CN, —NO$_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5 to 10-membered heteroaryl), $C_{0-10}$-alkylene-(6 to 10-membered aryl), $C_{0-10}$-alkylene-(6 to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$—R$^{13}$, $C_{0-10}$-alkylene-SO$_3$R$^{11}$, $C_{0-10}$-alkylene-SO$_2$NR$^{11}$R$^{12}$, $C_{0-10}$-alkylene-NR$^{11}$C(=O)R$^{11}$, $C_{0-10}$-alkylene-NR$^{11}$C(=S)R$^{11}$, $C_{0-10}$-alkylene-NR$^{11}$SO$_2$R$^{11}$, $C_{0-10}$-alkylene-NR$^{11}$C(=O)NR$^{11}$R$^{12}$, $C_{0-10}$-alkylene-NR$^{11}$C(=S)NR$^{11}$R$^{12}$, $C_{0-10}$-alkylene-NR$^{11}$—SO$_2$-NR$^{11}$R$^{12}$, $C_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, CONR$^{11}$R$^{12}$, CONR$^{11}$SO$_2$R$^{11}$, COR$^{11}$, SO$_x$R$^{11}$, SO$_3$H, PO(OH)$_2$, SO$_2$NR$^{11}$R$^{12}$, NR$^{11}$COR$^{11}$, NR$^{11}$SO$_2$R$^{11}$, NR$^{11}$—CO—NR$^{11}$R$^{12}$, NR$^{11}$—SO$_2$—NR$^{11}$R$^{12}$, $C_{3-10}$-cycloalkyl, O—$C_{3-10}$-cycloalkyl, $C_{3-10}$-heterocycloalkyl, O—$C_{3-10}$-heterocycloalkyl and NR$^{11}$R$^{12}$; and $R^{11}$, $R^{12}$, $R^{13}$ and x have the meaning as defined in any of the embodiments described herein.

In a more preferred embodiment in combination with any of the above or below embodiments $R^8$ is selected from H, —CN, —NO$_2$, $C_{1-3}$-alkyl, —C(=O)R$^{11}$ or —C(=O)—O—R$^{11}$ with $R^{11}$ being (linear or branched) $C_{1-4}$-alkyl.

In a most preferred embodiment in combination with any of the above or below embodiments $R^8$ is selected from H.

In an alternative preferred embodiment in combination with any of the above or below embodiments $R^9$ is selected from $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$R$^{13}$, $C_{0-10}$-alkylene-SO$_3$R$^{11}$, $C_{0-10}$-alkylene-SO$_2$NR$^{11}$R$^{12}$, $C_{0-10}$-alkylene-NR$^{11}$C(=O)R$^{11}$, $C_{0-10}$-alkylene-NR$^{11}$C(=S)R$^{11}$, $C_{0-10}$-alkylene-NR$^{11}$SO$_2$R$^{13}$, $C_{0-10}$-alkylene-NR$^{11}$C(=O)NR$^{11}$R$^{12}$, $C_{0-10}$-alkylene-NR$^{11}$C(=S)NR$^{11}$R$^{12}$, $C_{0-10}$-alkylene-NR$^{11}$SO$_2$NR$^{11}$R$^{12}$, $C_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, NR$^{11}$SO$_2$R$^{13}$, NR$^{11}$C(=O)NR$^{11}$R$^{12}$, NR$^{11}$SO$_2$NR$^{11}$R$^{12}$, $C_{3-10}$-cycloalkyl, O—$C_{3-10}$-cycloalkyl, $C_{3-10}$-heterocycloalkyl, O—$C_{3-10}$-heterocycloalkyl and NR$^{11}$R$^{12}$; and $R^{11}$, $R^{12}$, $R^{13}$ and x have the meaning as defined in any of the embodiments described herein.

In a more preferred embodiment in combination with any of the above or below embodiments $R^9$ is selected from $C_{1-10}$-alkyl, $C_{0-10}$-alkylene-$C_{3-10}$-cycloalkyl, $C_{0-10}$-alkylene-$C_{3-10}$-heterocycloalkyl, wherein alkyl, alkylene, cycloalkyl and heterocycloalkyl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen; and $R^{11}$ has the meaning as defined in any of the embodiments described herein.

In an even more preferred embodiment in combination with any of the above or below embodiments $R^9$ is selected from $C_{1-4}$-alkyl and $C_{3-6}$-cycloalkyl, wherein alkyl and cycloalkyl is unsubstituted or substituted with 1 to 3 substituents independently selected from the group consisting of fluorine or methyl.

In an even more preferred embodiment in combination with any of the above or below embodiments $R^9$ is selected from methyl, ethyl, isopropyl and cyclopropyl.

In a most preferred embodiment in combination with any of the above or below embodiments $R^9$ is selected from methyl and cyclopropyl.

A further embodiment of the invention relates to compounds of the Formula (Ia) and/or (Ib) supra in combination with any of the above or below embodiments, wherein $R^4$ is selected from $C_{1-6}$-alkyl, $C_{1-6}$-acyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, $C_{1-3}$-alkyl, halo-$C_{1-3}$-alkyl, O—$C_{1-3}$-alkyl, O-halo-$C_{1-3}$-alkyl;

$R^5$ and $R^6$ and $R^{5'}$ and $R^{6'}$ are independently selected from H and $C_{1-3}$-alkyl;

or $R^5$ and $R^6$ and $R^{5'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, OH, oxo, Me (—CH$_3$), OMe (—O—CH$_3$), CHF$_2$, CF$_3$, OCHF$_2$, OCF$_3$;

or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, OH, oxo, Me (—CH$_3$), OMe (—O—CH$_3$), CHF$_2$, CF$_3$, OCHF$_2$, OCF$_3$;

$R^7$ is selected from a 6-membered aryl and 5- or 6-membered heteroaryl, wherein aryl and heteroaryl are optionally substituted with 1 to 3 substituents independently selected from halogen, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)NR$^{11}$R$^{12}$, NR$^{11}$C(=O)NR$^{11}$R$^{12}$, NR$^{11}$C(=O)OR$^{13}$, OC(=O)NR$^{11}$R$^{12}$, C(=S)NR$^{11}$R$^{12}$, NR$^{11}$C(=S)NR$^{11}$R$^{12}$, NR$^{11}$C(=S)OR$^{13}$, OC(=S)NR$^{11}$R$^{12}$; SO—$C_{1-6}$-alkyl, SO$_2$-halo-$C_{1-6}$-alkyl, SR$^{11}$, SO$_x$R$^{13}$, SO$_3$R$^{11}$, SO$_2$NR$^{11}$R$^{12}$, NR$^{11}$SO$_2$R$^{13}$, NR$^{11}$SO$_2$NR$^{11}$R$^{12}$;

and wherein the remaining substituents have the meaning as defined in any of the embodiments described herein.

In a further preferred embodiment in combination with any of the above or below embodiments $R^4$ is selected from $C_{1-6}$-alkyl, $C_{1-6}$-acyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, $C_{1-3}$-alkyl, halo-$C_{1-3}$-alkyl, O—$C_{1-3}$-alkyl, O-halo-$C_{1-3}$-alkyl.

In a more preferred embodiment in combination with any of the above or below embodiments $R^4$ is selected from $C_{1-3}$-alkyl and halo-$C_{1-3}$-alkyl.

In an even more preferred embodiment in combination with any of the above or below embodiments $R^4$ is selected from Me (—CH$_3$).

In an alternative preferred embodiment in combination with any of the above or below embodiments $R^5$ and $R^6$ and $R^{5'}$ and R6' are independently selected from H, halogen, $C_{1-6}$-alkyl, NH$_2$, NHC$_{1-6}$-alkyl, N($C_{1-6}$-alkyl)$_2$, $C_{0-6}$-alkylene-C(=O)NH$_2$;

or $R^5$ and $R^6$ and $R^{5'}$ and R6' independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;

or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H.

In a more preferred embodiment in combination with any of the above or below embodiments $R^5$ and $R^6$ and $R^{5'}$ and $R^{6'}$ are independently selected from H, $C_{1-3}$-alkyl and halo-$C_{1-3}$-alkyl.

In an even more preferred embodiment in combination with any of the above or below embodiments $R^5$ and $R^6$ and $R^{5'}$ and $R^{6'}$ are hydrogens.

In an alternative preferred embodiment in combination with any of the above or below embodiments n is selected from 0 and 1.

In an even more preferred embodiment in combination with any of the above or below embodiments n is 0.

In yet another alternative preferred embodiment in combination with any of the above or below embodiments $R^7$ is selected from a 6-membered aryl and 5- or 6-membered heteroaryl, wherein aryl and heteroaryl are optionally substituted with 1 to 4 substituents independently selected from halogen, —CN, —NO$_2$, OH, $C_{1-6}$-alkyl, O—$C_{1-6}$-alkyl, $C_{3-6}$-cycloalkyl, O—$C_{3-6}$-cycloalkyl, $C_{3-6}$-heterocycloalkyl, O—$C_{3-6}$-heterocycloalkyl, SO—$C_{1-6}$-alkyl, CO$_2$H, C(=O)O—$C_{1-6}$-alkyl, 6- to 10-membered aryl, 5- or 10-membered heteroaryl, O-(6- to 10-membered aryl) and O-(5- or 10-membered heteroaryl), wherein alkyl, cycloalkyl, heterocycloalkyl, aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)NR$^{11}$R$^{12}$, NR$^{11}$C(=O)NR$^{11}$R$^{12}$, NR$^{11}$C(=O)OR$^{13}$, OC(=O)NR$^{11}$R$^{12}$, C(=S)NR$^{11}$R$^{12}$, NR$^{11}$C(=S)NR$^{11}$R$^{12}$, NR$^{11}$C(=S)OR$^{13}$, OC(=S)NR¹¹R¹²; SO—C$_{1-6}$-alkyl, SO$_y$-halo-C$_{1-6}$-alkyl, SR¹¹, SO$_x$R¹³, SO$_3$R¹¹, SO$_2$NR¹¹R¹², NR¹¹SO$_2$R¹³, NR¹¹SO$_2$NR¹¹R¹²; and R¹¹, R¹², R¹³, x and y have the meaning as defined in any of the embodiments described herein.

In a more preferred embodiment in combination with any of the above or below embodiments R⁷ is selected from a 6-membered aryl and 5- or 6-membered heteroaryl, wherein aryl and heteroaryl are optionally substituted with 1 to 3 substituents independently selected from halogen, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from halogen, —CN, —NO$_2$, OH, R¹³, OR¹³, CO$_2$R¹¹, NR¹¹R¹², C(=O)R¹¹, C(=S)R¹¹, C(=O)NR¹¹R¹², NR¹¹C(=O) NR¹¹R¹², NR¹¹C(=O)OR¹³, OC(=O)NR¹¹R¹², C(=S) NR¹¹R¹², NR¹¹C(=S)NR¹¹R¹², NR¹¹C(=S)OR¹³, OC(=S)NR¹¹R¹²; SO—C$_{1-6}$-alkyl, SO$_y$-halo-C$_{1-6}$-alkyl, SR¹¹, SO$_x$R¹³, SO$_3$R¹¹, SO$_2$NR¹¹R¹², NR¹¹SO$_2$R¹³, NR¹¹SO$_2$NR¹¹R¹²; and R¹¹, R¹², R¹³, x and y have the meaning as defined in any of the embodiments described herein.

In an even more preferred embodiment in combination with any of the above or below embodiments R⁷ is selected from a 6-membered aryl and 5- or 6-membered heteroaryl, wherein aryl and heteroaryl are optionally substituted with 1 to 3 substituents independently selected from halogen, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from halogen, OH, Me (—CH$_3$), OMe (—O—CH$_3$), CHF$_2$, CF$_3$, OCHF$_2$, OCF$_3$.

A further embodiment of the invention relates to compounds of the Formula (Ia) and/or (Ib) supra in combination with any of the above or below embodiments, wherein R⁷ is phenyl, optionally substituted with 1 to 4 substituents (R$^x$), which independently have the meaning as defined in any of the embodiments described herein for the possible substituents of R⁷, and which are represented by Formula (IIa) and (IIb):

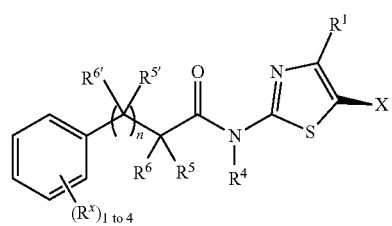

(IIa)

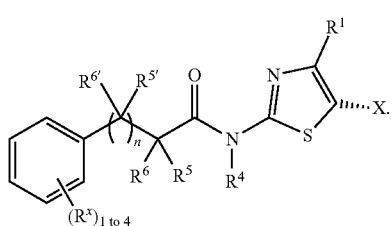

(IIb)

In an even more preferred embodiment in combination with any of the above or below embodiments R⁷ is selected from a phenyl, which is optionally substituted with 1 to 3 substituents independently selected from F, Cl, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from F, Cl, OH, Me (—CH$_3$), OMe (—O—CH$_3$), CHF$_2$, CF$_3$, OCHF$_2$, OCF$_3$.

In an even more preferred embodiment in combination with any of the above or below embodiments R⁷ is selected from an unsubstituted phenyl, which is substituted with phenyl or pyridyl, wherein phenyl or pyridyl are optionally substituted with 1 to 5 substituents independently selected from F, Cl, OH, Me (—CH$_3$), OMe (—O—CH$_3$), CHF$_2$, CF$_3$, OCHF$_2$, OCF$_3$.

In a most preferred embodiment in combination with any of the above or below embodiments R⁷ is selected from an unsubstituted phenyl, which is substituted with phenyl or pyridyl, wherein phenyl or pyridyl are optionally substituted with 1 to 3 substituents selected from F, Me (—CH$_3$), OMe (—O—CH$_3$), CHF$_2$, CF$_3$, OCHF$_2$, OCF$_3$.

An even more preferred embodiment of the invention relates to compounds of the Formula (Ia) and/or (Ib) and/or (IIa) and/or (IIb) supra in combination with any of the above or below embodiments, wherein R⁷ is selected from the group consisting of

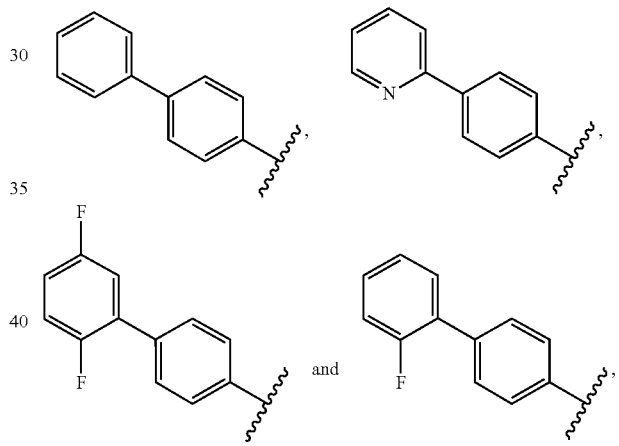

such as preferably from

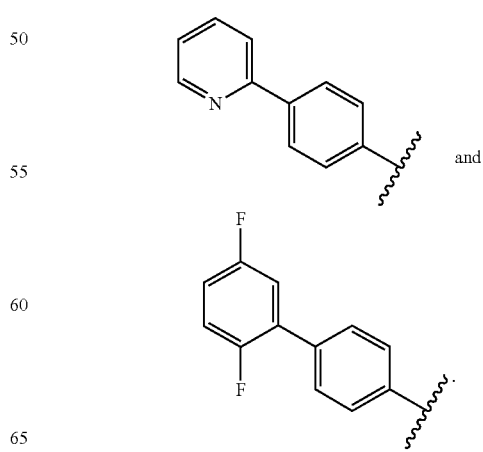

Another alternative preferred embodiment of the invention relates to compounds of the Formula (Ia) and/or (Ib) supra in combination with any of the above or below embodiments, wherein the group

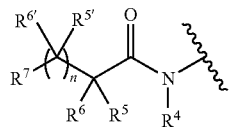

in Formula (Ia) and/or (Ib) is selected from the group consisting of

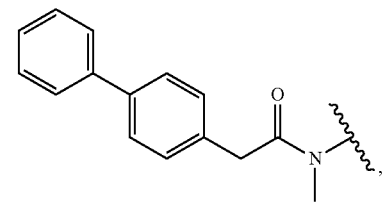

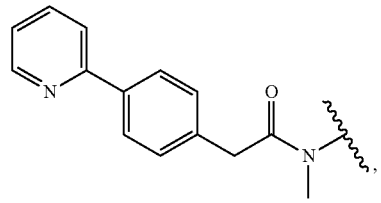

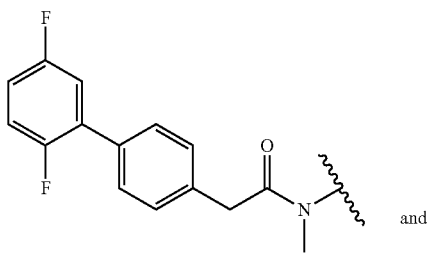

and

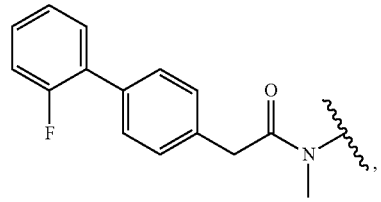

preferably from

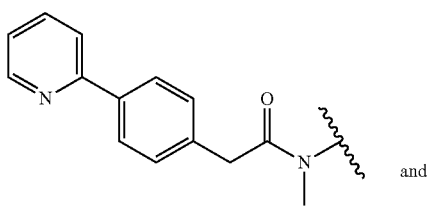

and

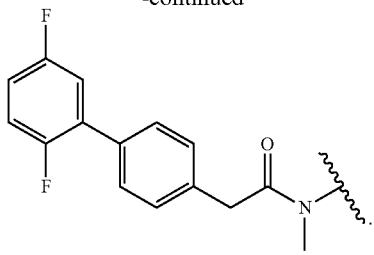

.

In yet another alternative preferred embodiment Formula (Ia) or (Ib) is selected from

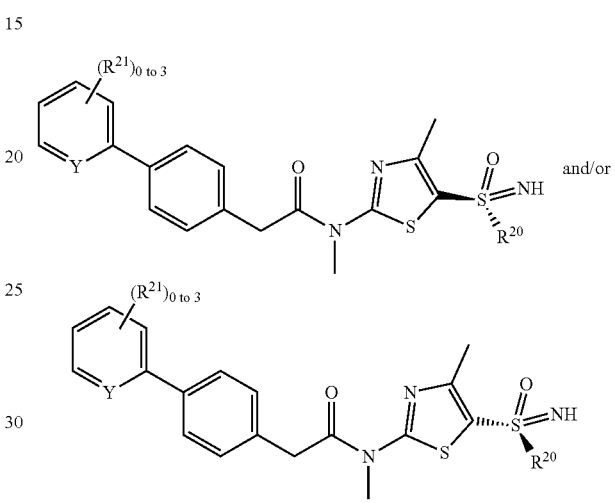

wherein
R$^{20}$ is selected from C$_{1-4}$-alkyl and C$_{3-6}$-cycloalkyl, wherein alkyl and cycloalkyl is unsubstituted or substituted with 1 to 3 substituents independently selected from the group consisting of F or Me;
R$^{21}$ is selected from F, Cl, OH, Me, OMe, CHF$_2$, CF$_3$, OCHF$_2$, OCF$_3$; and
Y is selected from nitrogen or carbon.

In a more preferred embodiment Formula (Ia) or (Ib) is selected from

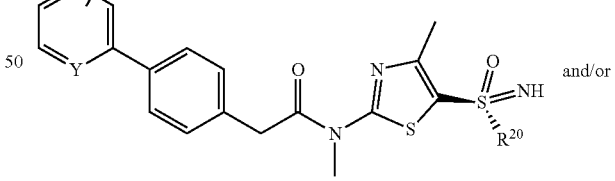

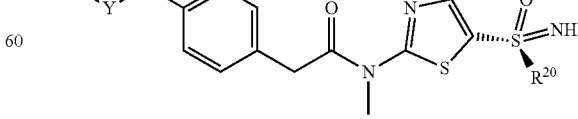

wherein
R$^{20}$ is selected from methyl, ethyl, isopropyl and cyclopropyl;

$R^{21}$ is selected from F, Cl, methyl, $CHF_2$, $CF_3$; and
Y is selected from nitrogen or carbon.

In yet another alternative preferred embodiment the compounds according to Formula (Ia) and/or (Ib) are selected from

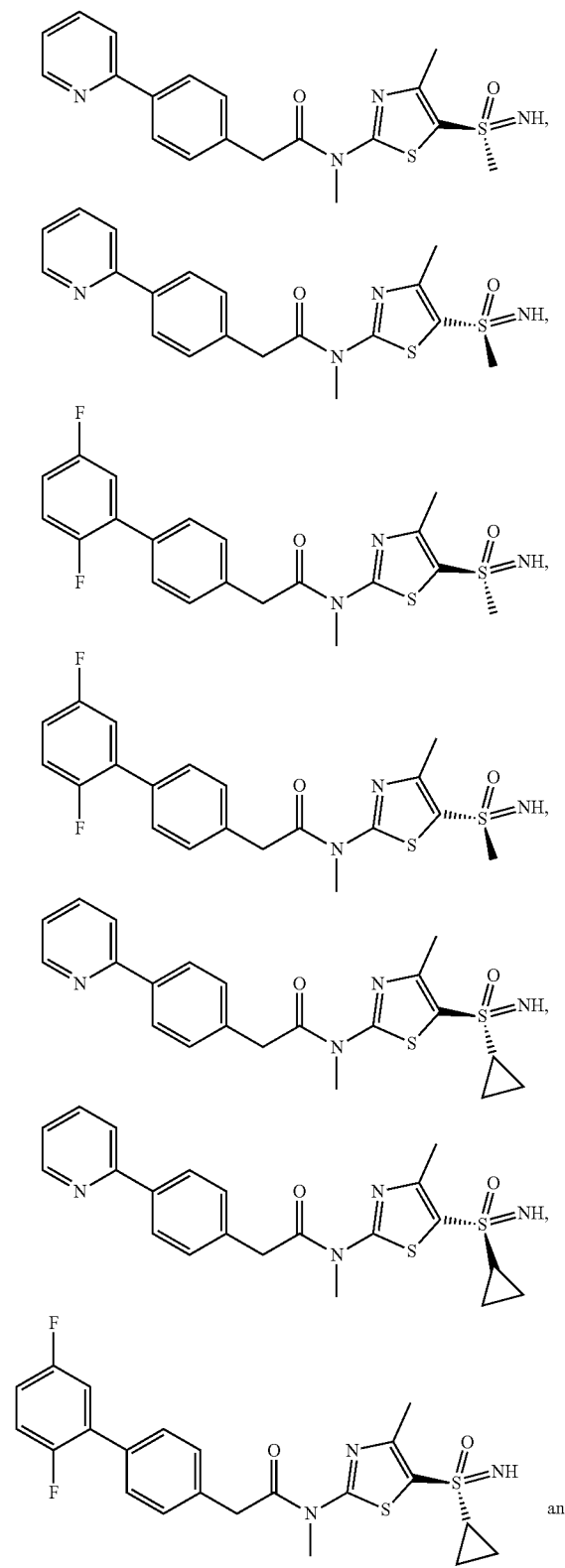

and

A further aspect of the present invention relates to the compounds according to the Formula (Ia), which are selected from the group consisting of

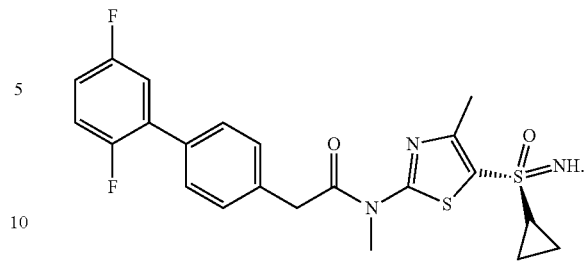

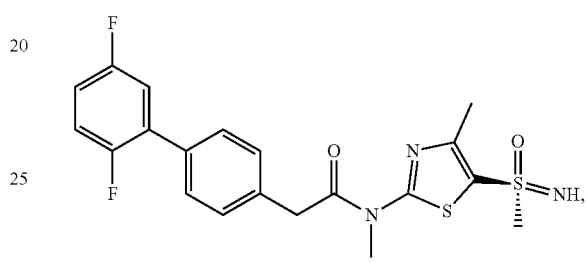

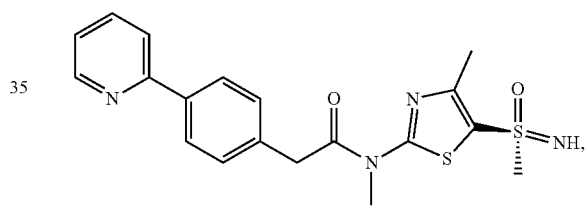

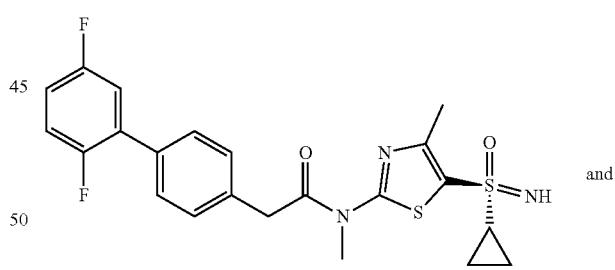 and

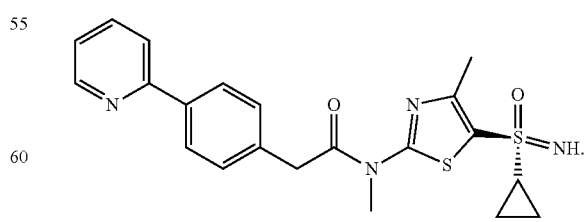

A further aspect of the present invention relates to the compounds according to the Formula (Ib), which are selected from the group consisting of

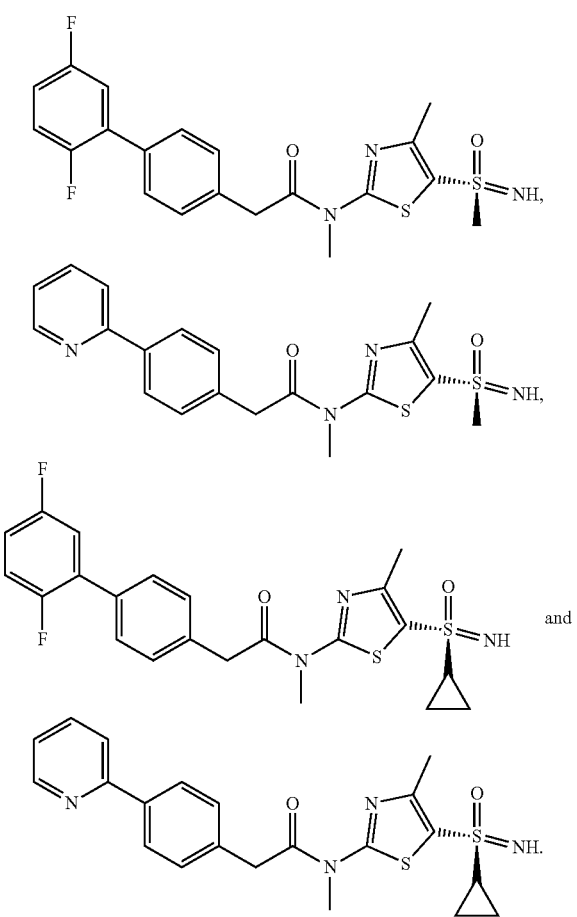

In another alternative preferred embodiment the compounds according to Formula (Ia) and/or (Ib) are selected from
(−)-N-Methyl-N-(4-methyl-5-(S-methylsulfonimidoyl)thiazol-2-yl)-2-(4-(pyridin-2-yl)phenyl)acetamide,
(−)-(S)-2-(2',5'-Difluoro-[, 1'-biphenyl]-4-yl)-N-methyl-N-(4-methyl-5-(S-methylsulfonimidoyl)thiazol-2-yl)acetamide,
(−)-N-(5-(Cyclopropanesulfonimidoyl)-4-methylthiazol-2-yl)-N-methyl-2-(4-(pyridin-2-yl)phenyl)acetamide, and
(−)-N-(5-(Cyclopropanesulfonimidoyl)-4-methylthiazol-2-yl)-2-(2',5'-difluoro-[1,1'-biphenyl]-4-yl)-N-methylacetamide.

In another alternative preferred embodiment the compounds according to Formula (Ia) and/or (Ib) are selected from
(−)-N-Methyl-N-(4-methyl-5-(S-methylsulfonimidoyl)thiazol-2-yl)-2-(4-(pyridin-2-yl)phenyl)acetamide.

In another alternative preferred embodiment the compounds according to Formula (Ia) or (Ib) are selected from
(−)-(S)-2-(2',5'-Difluoro-[, 1'-biphenyl]-4-yl)-N-methyl-N-(4-methyl-5-(S-methylsulfonimidoyl)thiazol-2-yl)acetamide.

In another alternative preferred embodiment the compounds according to Formula (Ia) or (Ib) are selected from
(−)-N-(5-(Cyclopropanesulfonimidoyl)-4-methylthiazol-2-yl)-N-methyl-2-(4-(pyridin-2-yl)phenyl)acetamide.

In another alternative preferred embodiment the compounds according to Formula (Ia) or (Ib) are selected from
(−)-N-(5-(Cyclopropanesulfonimidoyl)-4-methylthiazol-2-yl)-2-(2',5'-difluoro-[1,1'-biphenyl]-4-yl)-N-methylacetamide.

Preparation of Enantiomers

The enantiomers according to the present invention can be prepared by separation and isolation of the respective stereoselective compounds from the products resulting from non-stereoselective synthesis routes, thus comprising a mixture of the respective enantiomers, by preparative HPLC on an chiral column, such as e.g. described in the Examples 7, 7a, 7b and 7c below.

Further, it is possible to prepare the enantiomers as described herein by stereoselective synthesis and if necessary subsequent preparative HPLC on a chiral column or precipitation with chiral compounds etc.

Further, it is possible to prepare the enantiomers as described herein by stereoselective synthesis routes. The most common chiral, tetracoordinate sulfur compounds are sulfoximines which formally arise from achrial, unsymmetrical sulfones by replacement of one of the two oxygen atoms by the imino nitrogen. Consequently, replacement of both oxygen atoms in unsymmetrical sulfones by different imino groups leads to other chiral, tetracoordinate structures, namely sulfodiimides. Of interest is that chiral, optically active sulfonimidoyl chlorides have also been obtained. Due to the presence of a good leaving group, these chlorides are excellent substrates for nucleophilic substitution reaction and afford in a highly selective stereoselective way the corresponding esters and amides.

Syntheses of optically active sulfoximines is also possible from optically active sulfoxides. The review *Chem. Lett.* 2004:33, 482 summarizes routes for synthesis of sulfoximines. A recent publication in *Angew. Chem. Int. Ed.* 2016: 55, 7203 summarizes state of the art of synthesis of sulfoximines.

The chiral synthesis of sulfoximines can be accomplished by oxidation of readily available chiral sulfoxides (e.g. *Org. Lett.* 2006:8, 2349) or via chiral resolution of a racemic intermediate or racemic final compound via the tartrate (e.g. WO2012038411) or with camphorsulfonic acid (e.g. *Tetrahedron: Asymm.* 2001:12, 1255).

Thus, in a further aspect the present invention further relates to a process for preparing the compounds according to the Formula (Ia) and/or (Ib) supra, such as in particular the compounds according to any of the above described embodiments, the process comprising the steps a) providing a mixture comprising the compounds of the Formulae (Ia) and (Ib), such mixture being represented by the general Formula (I):

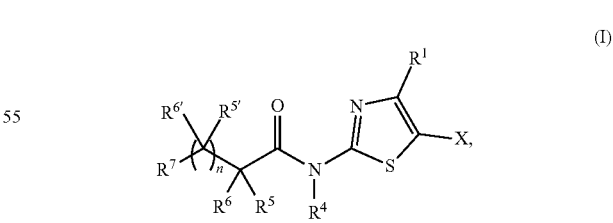

and b) separating and isolating the compounds of the Formula (Ia) and/or (Ib) using HPLC on a chiral column;

wherein in the Formula (I) the substituents have the meaning as defined in the embodiments described supra.

It is clear for a skilled person, that in the process of the present invention the substituents of Formula (I) have the particular meaning, corresponding to the meaning of any particular embodiment as defined supra.

In a more preferred embodiment Formula (Ia) and/or (Ib) is selected from

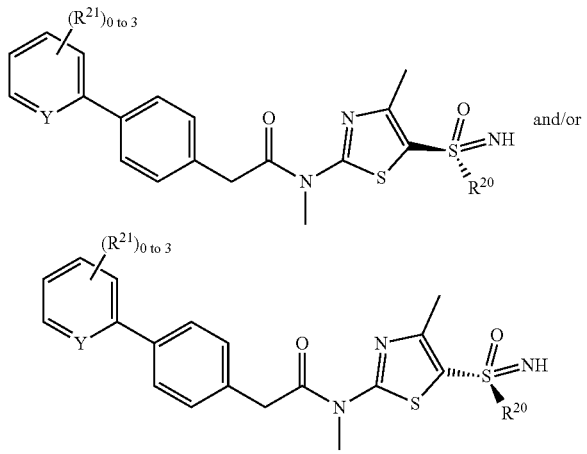

and in step b) the separation on a chiral column affords pure (−)-enantiomer.

In a further aspect the present invention relates to a process for preparing the compounds according to the Formula (Ia) and/or (Ib) supra, such as in particular the compounds according to any of the above described embodiments by stereoselective synthesis and optionally subsequent preparative HPLC on a chiral column or precipitation with chiral compounds.

Accordingly, in a further aspect the present invention relates to the compounds obtainable by any of the the processes as described herein.

A further aspect of the present invention relates to the compounds of any of the above described embodiments, as well as to the compounds obtainable by any of the processes of the present invention for the use as a medicament.

Particularly the invention relates to the described compounds of the present invention for use in the treatment or prophylaxis of a disease or disorder associated with viral infections.

More specifically the invention relates to the described compounds of the present invention for use in the treatment and prophylaxis of a disease or disorder associated with viral infections caused by wild type or genetically engineered viruses encoding a helicase and/or primase by inhibiting the helicase and/or primase enzymes.

More specifically the invention relates to the described compounds of the present invention for use in the treatment and prophylaxis of a disease or disorder associated with viral infections caused by wild type or genetically engineered viruses which nucleic acid encodes a helicase and/or primase and the related enzymes can be inhibited by said compounds at concentrations below 100 µM in vitro.

More particularly the invention relates to the described compounds of the present invention for use in the treatment or prophylaxis of a disease or disorder, which is associated with viral infections caused by herpes viruses, such as in particular by herpes simplex viruses or more particular HHV1 also named HSV-1 and/or HHV2 also named HSV-2.

In a further aspect the invention relates to the described compounds of the present invention for use in the treatment or prophylaxis neurodegenerative diseases caused by viruses, such as in particular Alzheimer's disease.

In a further aspect the invention relates to the described compounds of the present invention for the use in the treatment and prophylaxis of herpes infections, in particular herpes simplex infections in patients displaying herpes disease such as herpes labialis, herpes genitalis and herpes-related keratitis, Alzheimer's disease, encephalitis, pneumonia, hepatitis or viral shedding being a risk for transmission; in patients with a suppressed immune system, such as AIDS patients, cancer patients, patients having a genetic or inherited immunodeficiency, transplant patients; in new-born children and infants; in herpes-positive patients, in particular herpes-simplex-positive patients, for suppressing recurrence or viral shedding (suppression therapy); patients, in particular in herpes-positive patients, in particular herpes-simplex-positive patients, who are resistant to nucleosidic antiviral therapy such as acyclovir, penciclovir, famciclovir, ganciclovir, valacyclovir or resistant to foscarnet or cidofovir.

In a further aspect the invention relates to the described compounds of the present invention, which are characterized by an $IC_{50}$ value (HSV-1/Vero) in an in vitro activity selectivity assay HSV-1 on Vero cells as described in the Examples of the present invention of preferably $IC_{50}$ below 100 µM, more preferably $IC_{50}$ below 10 µM and very particularly preferable $IC_{50}$ below 1 µM.

In a further aspect the invention relates to the described compounds of the present invention, which are characterized by an $ED_{50}$ value in an in vivo animal model as described in the Examples of the present invention preferably of $ED_{50}$ of less than 10 mg/kg for HSV-1, more preferably of less than 5 mg/kg for HSV-1, and very particularly preferable of less than 2 mg/kg for HSV-1.

In a further aspect the invention relates to the described compounds, which are characterized by showing no or reduced carbonic anhydrase inhibition, such particularly inhibition of carbonic anhydrase I and/or carbonic anhydrase II. In the sense of the present invention no or reduced carbonic anhydrase inhibition is particularly defined by $IC_{50}$-values (inhibitory concentration) in a carbonic anhydrase II activity assay according to R. Iyer et al. *J. Biomol. Screen.* 2006:11, 782 and/or in a carbonic anhydrase I activity assay according to A. R. Katritzky et al. *J. Med. Chem.* 1987:30, 2058 of $IC_{50}$>2.0 µM, preferably >3.0 µM, more preferably >5.0 µM. Even more preferably, no or reduced carbonic anhydrase inhibition in the sense of the present invention is particularly defined by $IC_{50}$-values (inhibitory concentration) in a human carbonic anhydrase II activity assay as described in detail in the Examples of the present invention of $IC_{50}$>2.0 µM, preferably >3.0 µM, more preferably >5.0 µM and most preferably >10 µM.

The compounds of the present invention are considered for the use in the prophylaxis and treatment of the respective disorders and diseases in humans as well as in animals.

Accordingly, the invention relates to the use of the compounds of the present invention as described herein for the preparation of a medicament.

Further, the invention relates to a method of treating a disease or disorder associated with viral infections, such as a disease or disorder, which is associated with viral infections caused by herpes viruses, such as in particular by herpes simplex viruses as well as a method of treating neurodegenerative diseases caused by viruses, such as in particular Alzheimer's disease, said methods comprising administering to a human or animal in need thereof an effective amount of a compound of the present invention or of a composition comprising said compounds of the present invention as described herein.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray or as eye drops.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring such as cherry or orange flavour.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal, and the like may be employed. Dosage forms include tablets, troches, dispersions, suspensions, solutions, capsules, creams, ointments, aerosols, and the like. Preferably compounds of the present invention are administered orally or as eye drops, more preferably the compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

The compounds of the present invention may also be present in combination with further active ingredients, in particular with one or more active ingredients exhibiting advantageous effects in the treatment of any of the disorders or diseases as described herein. Very particularly the compounds of the present invention are present in a composition in combination with at least one further active substance being effective in treating a disease or disorder associated with viral infections (antiviral active compounds), preferably a disease or disorder being associated with viral infections caused by herpes viruses, such as in particular by herpes simplex viruses, thus relating to a so called combination therapy. The at least one further active substance being effective in treating a disease or disorder associated with viral infections (antiviral active compounds) are preferably selected from the group consisting of nucleosidic drugs such as acyclovir, valacyclovir, penciclovir, ganciclovir, famciclovir and trifluridine, as well as compounds such as foscarnet and cidofovir or its ester cidofovir [(S)-HPMPC] bearing a hexaethyleneglycol moiety.

Accordingly, the present invention further relates to a pharmaceutical composition comprising one or more of the novel compounds of the present invention as described herein and at least one pharmaceutically acceptable carrier and/or excipient and/or at least one further active substance being effective in treating a disease or disorder associated with viral infections (antiviral active compounds).

EXPERIMENTAL PART

The mixtures comprising the compounds of the present invention according to Formula (Ia) and (Ib) and as described in any of the embodiments above, used in step a) of the process of the present invention as described above, can be prepared by a combination of methods known in the art including the procedures described in Schemes I to III of the unpublished international application PCT/EP2017/058077 and comprising further details as presented below.

The synthesis of the acid building block $R^7(CR^5R^6)_n$ $CR^5R^6COOH$ can be made as described in WO2001/47904 and coupled to the appropriate thiazole building block.

Coupling of acid building block $R^7(CR^5R^6)_n$ $CR^5R^6COOH$ with 5-sulfonic acid-substituted thiazole can afford intermediate IIa (Scheme II), which can be converted to sulfonyl chloride IIb by treating with oxalyl chloride. Reaction of this intermediate with $NHR^2R^3$ and triphenylphosphine give target compound IIc, which finally can be oxidized e.g. with tert-butylhypo chlorite in prescence of $NH_2R^8$ to furnish target compound IId. An alternative route towards derivatives IId using readily available sulfonimides is described by Y. Chen et al. (*RSC Advances* 2015:5, 4171) through nucleophilic substitution of sulfonimidoyl chloride formed in situ with different amines. Additional routes for derivatives IId are described in *Angew. Chem. Int. Ed.* 2013:52, 9399 and *ChemMedChem* 2013:8, 1067.

Scheme II

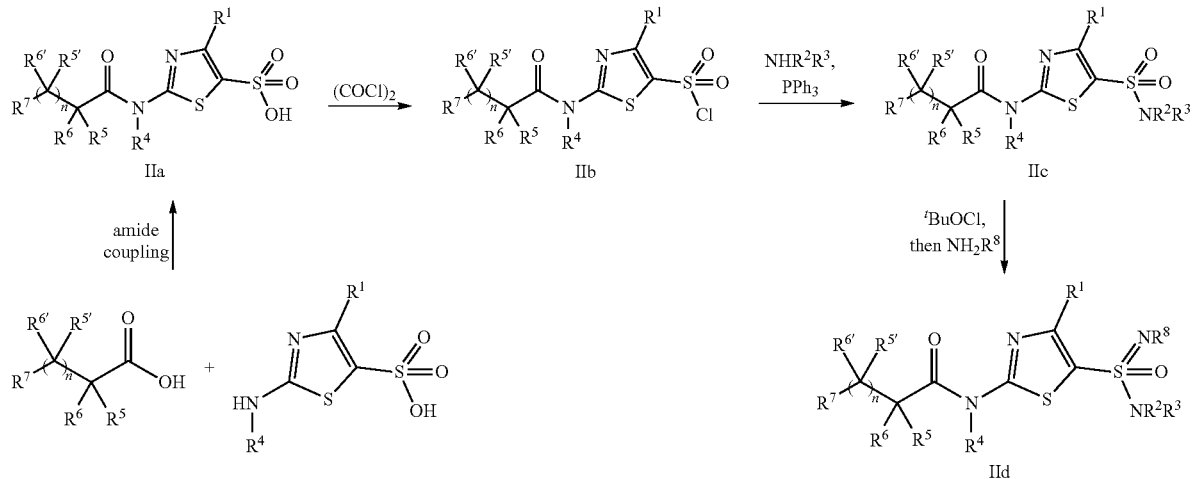

Coupling of acid building block $R^7(CR^{5'}R^{6'})_n$ $CR^5R^6COOH$ with 5-alkylthio-substituted thiazole can afford intermediate IIIa (Scheme III), which can get oxidized to the alkylsulfinyl derivative IIIb. Also, oxidation of intermediate IIIa with azido derivative $N_3R^8$ and $FeCl_2$ can furnish sulfinimidoyl derivative IIIc, which can further get oxidized, e.g. with $NaIO_4/RuCl_3$ to afford sulfonimidoyl derivative IIId. In case $R^8$ represents a cyano residue, an alternative route as outlined by S. J. Park et al. (*ChemMedChem* 2013:8, 217) can also be used ($H_2NCN$, $PhI(OAc)_2$, then metaCPBA).

In all cases $R^2$, $R^3$ or $R^8$ may serve as a protecting group and can get deprotected similar as described in e.g. Greene's Protective Groups in Organic Synthesis (ISBN: 978-1-118-05748-3).

Compounds of the invention have a chiral sulfur atom attached to the thiazole ring, giving rise to the existence of two enantiomers, having either R- or S-configuration at the sulfur atom, and which are the object of the present invention. In particular, this is the case for S-substituted sulfoximines as depicted in Scheme IV:

Scheme III

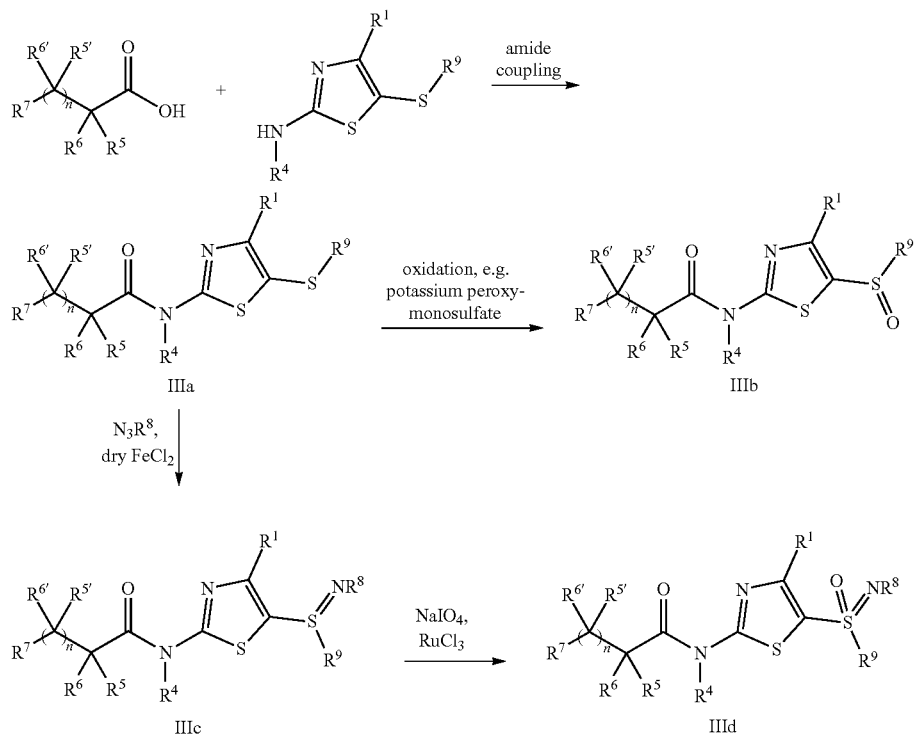

Scheme IV

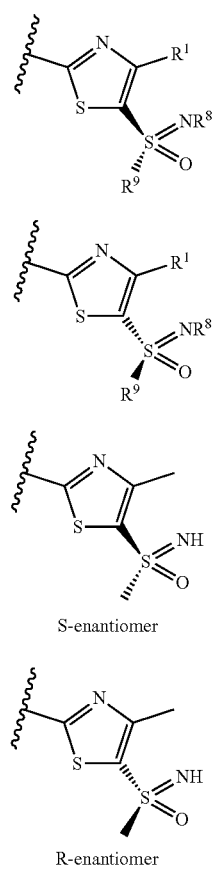

S-enantiomer

R-enantiomer

The general fragment structures Ia and Ib are pairs of enantiomers. In the case of $R^9$ is alkyl, e.g. methyl and $R^8$ is a proton, as depicted in the fragment structures IIIa and IIIb, IIIa has the S-configuration, IIIb has the R-configuration.

Homochiral compounds of the invention can be prepared by separation of the racemic mixture by chromatography on a chiral stationary phase, e.g. using HPLC or SCF technology with an appropriate chiral stationary phase (chiral column material) and appropriate mobile phases, under appropriate conditions such as flow rate, pressure and temperature.

Alternatively, homochiral compounds of the present invention may be prepared by classical resolution, using formation of an appropriate diastereomeric salt, subsequent recrystallization and final liberation of the free base. In addition, a racemic mixture of chiral sulfoximines may be resolved into its enantiomers by organocatalytic kinetic resolution as described in *J. Am. Chem. Soc.* 2016:138, 2166.

Also alternatively, homochiral compounds of the present invention may be prepared by stereoselective syntheses, giving rise to enantioenriched final compounds which may be recrystallized to afford enantiopure homochiral compounds.

Syntheses of optically active sulfoximines is also possible from optically active sulfoxides. The review *Chem. Lett.* 2004:33, 482 summarizes routes for synthesis of sulfoximines. A recent publication in *Angew. Chem. Int. Ed.* 2016: 55, 7203 summarizes state of the art of synthesis of sulfoximines.

In the reaction schemes the remaining substituents may have the meaning as defined in the present invention.

Abbreviations

ACN acetonitrile
aq. aqueous
DCM dichloromethane
DMF dimethylformamide
DMSO dimethylsulfoxide
EA ethyl acetate
h hour(s)
HPMC hydroxypropylmethylcellulose
IPA isopropyl alcohol
THF tetrahydrofuran
PE petroleum ether
rt room temperature (23° C.±2° C.)
sat. saturated (aqueous)

In particular, the following starting compounds can be prepared as follows, being obtainable in each case as mixtures (or racemates) comprising the respective specific stereo-isomers/enantiomers as obtainable by the process of the present invention.

Experimental Section

Example 4: 2-(2',5'-Difluoro-[1,1'-biphenyl]-4-yl)-N-methyl-N-(4-methyl-5-(methylsulfinyl) thiazol-2-yl)acetamide

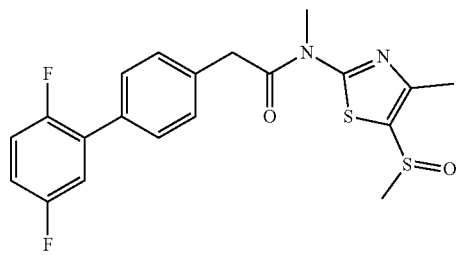

Step 1: N,4-Dimethyl-5-(methylthio)thiazol-2-amine (P4a)

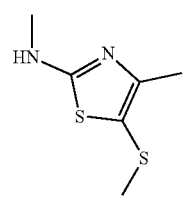

To a solution of 5-bromo-N,4-dimethylthiazol-2-amine (2.06 g, 9.95 mmol) in MeOH (20 mL) was slowly added under ice cooling a solution of NaSMe (1.74 g, 24.9 mmol) in MeOH (15 mL). The mixture was heated to 60° C. and stirred for 2 h, evaporated and suspended in MeCN. After centrifugation, the supernatant was separated and evaporated. The obtained solid was slurried with $Et_2O$ and centrifuged to give intermediate P4a.

Step 2: 2-(2',5'-Difluoro-[1,1'-biphenyl]-4-yl)-N-methyl-N-(4-methyl-5-(methylthio)thiazol-2-yl)acetamide (P4b)

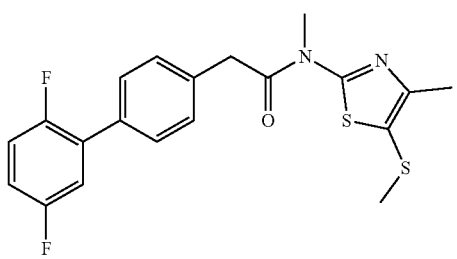

P4b

A solution of amine P4a (994 mg; 5.71 mmol) and DIPEA (1.89 mL, 11.4 mmol) in DMF (3 mL) was cooled to −20° C., then a cooled solution of 2-(2',5'-difluoro-[1,1'-biphenyl]-4-yl)acetic acid (1.56 g, 6.28 mmol; WO 2003/000259) and 1-[bis(dimethylamino)methylene]-1H-1,2,3-triazolo[4,5-b]pyridinium 3-oxid hexafluorophosphate (2.39 g, 6.28 mmol) in DMF (5 mL) was added and the mixture was stirred at rt overnight, poured into water and extracted with EtOAc (2×). The combined organic layer was washed with brine (2×) and a saturated solution of NaHCO₃, dried over Na₂SO₄, evaporated and purified by column chromatography (PE/DCM=1:0 to 1:1) to afford intermediate P4b (625 mg, 27%).

Step 3: 2-(2',5'-Difluoro-[1,1'-biphenyl]-4-yl)-N-methyl-N-(4-methyl-5-(methylsulfinyl)thiazol-2-yl)acetamide (4)

A solution of intermediate P4b (1.4 g, 3.46 mmol) in MeOH (35 mL) was cooled to 0° C., then potassium peroxymonosulfate (1.09 g, 1.77 mmol) in water (18 mL) was added and the solution was stirred for 20 min at 0° C., quenched with a saturated Na₂S₂O₃-solution and extracted with EtOAc (2×). The combined organic layer was washed with water (2×) and brine, dried over Na₂SO₄, evaporated and purified by column chromatography (PE/DCM/MeOH=1:0:0 to 1:1:0 to 0:19:1) to afford the Example 4 (419 mg, 29%). $^1$H-NMR (CDCl₃, 250 MHz) δ: 7.57-7.53 (m, 2H), 7.37 (d, 2H), 7.17-6.98 (m, 3H), 4.09 (s, 2H), 3.75 (s, 3H), 2.96 (s, 3H), 2.51 (s, 3H). MS found: 421.3 [M+H]⁺, 841.5 [2M+H]⁺.

The resulting product comprises a mixture of the respective enantiomers/stereoisomers and can be used for preparing the particular enantiomeric compounds according to the present invention, e.g. in step a) of the process of the present invention as described above, by isolating the enantiomers therefrom.

Example 5: 2-(2',5'-Difluoro-[1,1'-biphenyl]-4-yl)-N-methyl-N-(4-methyl-5-(S-methyl-N-((1,1-dimethylethoxy)carbonyl)sulfinimidoyl)thiazol-2-yl)acetamide

5

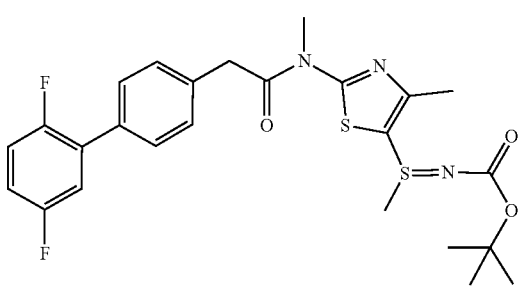

A solution of compound P4b (197 mg, 390 μmol) and tert-butyl azidoformate (277 mg, 1.95 mmol) in dry, degassed DCM (1.5 mL) was cooled to −20° C. under argon. Then anhydrous FeCl₂ (49 mg, 390 μmol) was added and the solution was allowed to reach rt and stirred for 4 h, diluted with water and extracted with EtOAc (2×). The combined organic layer was washed with water and brine, dried over Na₂SO₄ and evaporated to afford Example 5. MS found: 520.4 [M+H]⁺.

The resulting product comprises a mixture of the respective enantiomers/stereoisomers and can be used for preparing the particular enantiomeric compounds according to the present invention, e.g. in step a) of the process of the present invention as described above, by isolating the enantiomers therefrom.

Example 6: 2-(2',5'-Difluoro-[1,1'-biphenyl]-4-yl)-N-methyl-N-(4-methyl-5-(S-methyl-N-((1,1-dimethylethoxy)carbonyl)sulfonimidoyl)thiazol-2-yl)acetamide

6

To a solution of compound 5 (100 mg, 193 μmol) in THF (10 mL) was added a solution of NaIO₄ (206 mg, 963 μmol) in water (3 mL) and ruthenium(III) chloride hydrate in water (330 μL). After 5 min the mixture was diluted with water and EtOAc and extracted with EtOAc (3×). The combined organic layer was washed with water and brine, dried over Na₂SO₄, evaporated and purified by HPLC to afford Example 6.

The resulting product comprises a mixture of the respective enantiomers/stereoisomers and can be used for preparing the particular enantiomeric compounds according to the present invention, e.g. in step a) of the process of the present invention as described above, by isolating the enantiomers therefrom.

Example 7: 2-(2',5'-Difluoro-[1,1'-biphenyl]-4-yl)-N-methyl-N-(4-methyl-5-(S-methylsulfonimidoyl)thiazol-2-yl)acetamide

7

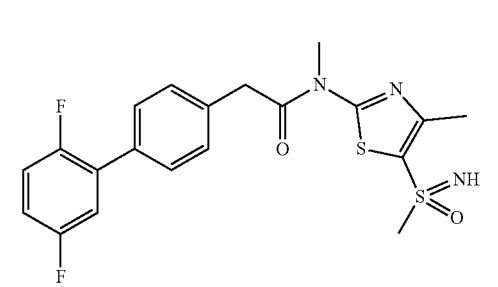

To a solution of compound 6 in DCM was added 50% aq. trifluoroacetic acid at −20° C. and the mixture was stirred for 1 h at rt, evaporated and lyophilized from tert-BuOH/H$_2$O (4:1) to obtain Example 7. $^1$H-NMR (CDCl$_3$, 400 MHz) δ: 7.56-7.53 (m, 2H), 7.36 (d, 2H), 7.18-6.95 (m, 3H), 4.08 (s, 2H), 3.75 (s, 3H), 2.95 (s, 3H), 2.51 (s, 3H). MS found: 436.3 [M+H]$^+$.

The resulting product comprises a mixture of the respective enantiomers/stereoisomers and can be used for preparing the particular enantiomeric compounds according to the present invention, e.g. in step a) of the process of the present invention as described above, by isolating the enantiomers there from.

Preparation of Enantiomers of Example 7

Example 7(−): (−)-(S)-2-(2',5'-Difluoro-[1,1'-biphenyl]-4-yl)-N-methyl-N-(4-methyl-5-(S-methylsulfonimidoyl)thiazol-2-yl)acetamide

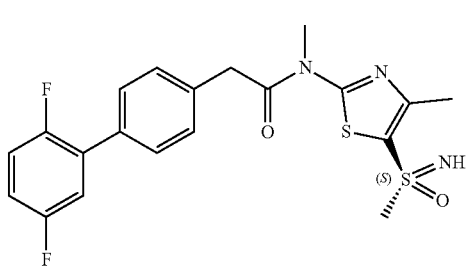

7(−)

The title compound was prepared and further characterized by separation of the racemic mixture 7 by chiral SFC chromatography, using as stationary phase Chiralcel OJ-H and as mobile phase 70/30 vol. % CO$_2$/MeOH.

The following conditions were applied:

| Injection Info | |
|---|---|
| Injection Date Time Stamp | 6/26/2017 2:52:00 PM |
| Injection Volume | 5 |
| Co-Solvent | MeOH |
| Column | OJ-H (4.6*100*5 um) |
| Sample | ZFX-435-M |
| Sample Well | P1: 1D |
| Column Temperature | 39.3 |
| CO2 Flow Rate | 2.8 |
| Co-Solvent Flow Rate | 1.2 |
| Co-Solvent % | 30 |
| Total Flow | 4 |
| Front Pressure | 157 |
| Back Pressure | 120 |
| Pressure Drop | 37 |
| PDA Start Wavelength | 214 |
| PDA Stop Wavelength | 359 |

Example 7(−) is the first eluting enantiomer (retention time: 2.4 min, FIG. 1a and 1b). Assignment to (S)-configuration was accomplished via X-ray analysis of Example 8.

Said enantiomer is further characterized by a negative specific optical rotation of $[α]^{20}_{Hg365\ nm}$−19° (c=1 g/100 mL, CHCl$_3$).

$^1$H-NMR (DMSO-d$_6$, 500 MHz) δ: 7.56-7.58 (m, 2H), 7.45-7.36 (m, 4H), 7.29-7.25 (m, 1H), 4.69 (s, 1H), 4.23 (s, 2H), 3.72 (s, 3H), 3.14 (d, J=0.5 Hz, 3H), 2.52 (s, 3H). MS found: 436.3 [M+H]$^+$.

Alternative Enantiomeric Separation for Example 7(−):

The title compound was prepared and further characterized by separation of the racemic mixture 7 by chiral SFC chromatography, using as stationary phase OJ 20×250 mm, 10 μm (Daicel) and as mobile phase CO$_2$/IPA:ACN=55/45 and additional following data:

Instrument: SFC-80 (Thar, Waters)
Column temperature: 35° C.
Flow rate: 80 g/min
Back pressure: 100 bar
Detection wavelength: 254 nm
Cycle time: 4 min
Sample solution: 60 g dissolved in 2000 mL IPA
Injection volume: 4.5 mL Example 7(−) is the first eluting enantiomer (retention time: 3.1 min). It has a positive specific optical rotation of $[α]^{20}_{589\ nm}$+3.4° (c=0.9644 g/100 mL, ACN).

Example 7(+): (+)-(R)-2-(2',5'-Difluoro-[1,1'-biphenyl]-4-yl)-N-methyl-N-(4-methyl-5-(S-methylsulfonimidoyl)thiazol-2-yl)acetamide

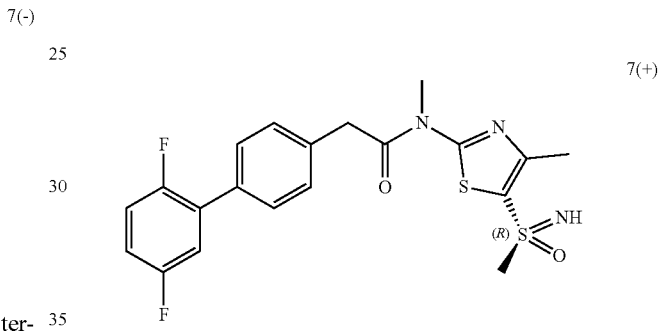

7(+)

The title compound was prepared and further characterized by separation of the racemic mixture 7, resulting from Example 7, by chiral SFC chromatography, using as stationary phase Chiralcel OJ-H and as mobile phase 70/30 vol. % CO$_2$/MeOH.

The following conditions were applied:

| Injection Into | |
|---|---|
| Injection Date Time Stamp | 6/26/2017 2:52:00 PM |
| Injection Volume | 5 |
| Co-Solvent | MeOH |
| Column | OJ-H (4.6*100*5 um) |
| Sample | ZFX-435-M |
| Sample Well | P1: 1D |
| Column Temperature | 39.3 |
| CO2 Flow Rate | 2.8 |
| Co-Solvent Flow Rate | 1.2 |
| Co-Solvent % | 30 |
| Total Flow | 4 |
| Front Pressure | 157 |
| Back Pressure | 120 |
| Pressure Drop | 37 |
| PDA Start Wavelength | 214 |
| PDA Stop Wavelength | 359 |

Example 7(+) is the second eluting enantiomer (retention time: 3.2 min, FIGS. 1a and 1c). Assignment to (R)-configuration was accomplished via X-ray analysis of Example 8.

Said enantiomer is further characterized by a positive specific optical rotation of $[α]^{20}_{Hg365\ nm}$+20° (c=1 g/100 mL, CHCl$_3$).

$^1$H-NMR (DMSO-d$_6$, 500 MHz) δ: 7.56-7.58 (m, 2H), ), 7.45-7.36 (m, 4H), 7.29-7.25 (m, 1H), 4.69 (s, 1H), 4.23 (s, 2H), 3.72 (s, 3H), 3.14 (d, J=0.5 Hz, 3H), 2.52 (s, 3H). MS found: 436.3 [M+H]$^+$.

Example 7a: N-[5-(Cyclopropylsulfonimidoyl)-4-methyl-thiazol-2-yl]-2-[4-(2,5-difluorophenyl)phenyl]-N-methyl-acetamide

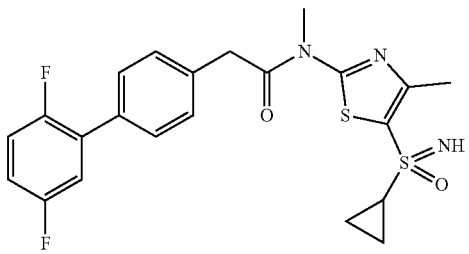

Step 1: Cyclopropanethiol (P7aa)

To a solution of cyclopropyl magnesium bromide (80 mL, 80 mmol) in THF (20 mL) was added sulfur (2.56 g, 80 mmol) and the mixture was stirred under reflux for 1 h. After cooling to 0° C., LiAlH$_4$ (0.76 g, 80 mmol) was added, the mixture was stirred under reflux for 1 h, then cooled to rt. 25% aq. H$_2$SO$_4$ was added slowly and the mixture was extracted with Et$_2$O. The organic phase was washed with water, sat. NaHCO$_3$ and brine and dried over Na$_2$SO$_4$. The crude product P7aa was used directly in the next step without purification.

Step 2: 5-(Cyclopropylthio)-N,4-dimethylthiazol-2-amine (P7ab)

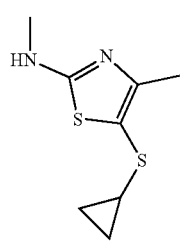

To a solution of 5-bromo-N,4-dimethylthiazol-2-amine in DMF (20 mL) (2.5 g, 12.1 mmol), was added a solution of crude product P7aa from Step 1 (80 mmol, th.) and K$_2$CO$_3$ (3.3 g, 24.2 mmol) and the mixture was stirred at 60° C. for 16 h. The mixture was filtered through Celite, water was added and the mixture was extracted with EtOAc. The organic phase was washed with water and brine, dried over Na$_2$SO$_4$, filtered, and concentrated. The residue was purified by column chromatography on silica gel to afford the title compound (0.60 g, 25%) as a solid.

N-[5-(Cyclopropylsulfonimidoyl)-4-methyl-thiazol-2-yl]-2-[4-(2,5-difluorophenyl)phenyl]-N-methyl-acetamide (7a)

Example 7a was prepared using a similar method as described for Example 7, using compound P7ab as starting material. $^1$H-NMR (CDCl$_3$, 400 MHz) δ: 7.56-7.54 (m, 2H), 7.35 (d, J=8.4 Hz, 2H), 7.14-7.07 (m, 2H), 7.02-6.97 (m, 1H), 4.07 (s, 2H), 3.73 (s, 3H), 3.22-2.84 (s, br, 1H), 2.70-2.66 (m, 1H), 1.41-1.34 (m, 1H), 1.30-1.21 (m, 1H), 1.10-1.01 (m, 1H), 1.00-0.91 (m, 1H). MS found: 461.1 [M+H]$^+$.

The resulting product comprises a mixture of the respective enantiomers/stereoisomers and can be used for preparing the particular enantiomeric compounds according to the present invention, e.g. in step a) of the process of the present invention as described above, by isolating the enantiomers therefrom.

Preparation of Enantiomers of Example Compound 7a

Example 7a(−): (−)-N-(5-(Cyclopropanesulfonimidoyl)-4-methylthiazol-2-yl)-2-(2′,5′-difluoro-[1,1′-biphenyl]-4-yl)-N-methylacetamide

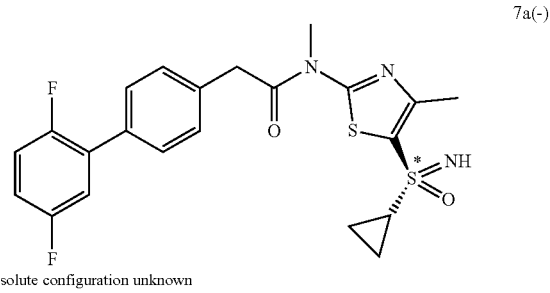

* absolute configuration unknown

Step a)
The racemic mixture 7a resulting from Example 7a, comprising a mixture of the respective enantiomers/stereoisomers was provided.

Step b)
The title compound was prepared by separation of the racemic mixture 7a by chiral SFC chromatography, using as stationary phase Chiralcel OD-3 and as mobile phase 65/35 vol. % CO$_2$/(EtOH/ACN).

The following conditions were applied:
Column: CHIRALCEL OD-3(46*100 mm, 3 um)
Co_Solvent: EtOH/ACN
Column_Temperature: 35
Co_Solvent %: 35
Back_Pressure: 2000 psi
Flow_rate: 2 mL/min
Proc. Chnl. Descr.: PDA 2805 nm (210-400 ) nm
PDA_Start_Wavelength: 200 nm
PDA_Stop_Wavelength: 400 nm
Example 7a(−) is the enantiomer eluting first (retention time: 1.8 min, FIGS. 2a and 2b).

Said enantiomer is further characterized by a negative specific optical rotation of $[\alpha]^{20}_{Hg365\ nm}$ −84° (c=0.5 g/100 mL, CHCl$_3$), $[\alpha]^{20}_{Na589\ nm}$ −22° (c=1 g/100 mL, CHCl$_3$).

$^1$H-NMR (CDCl$_3$, 400 MHz) δ: 7.54 (d, J=8.0 Hz, 2H), 7.35 (d, J=8.0 Hz, 2H), 7.15-7.08 (m, 2H), 7.02-6.98 (m, 1H), 4.08 (s, 2H), 3.74 (s, 3H), 3.06 (s, 1H), 2.71-2.67 (m, 1H), 1.41-1.36 (m, 1H), 1.31-1.26 (m, 1H), 1.08-1.05 (m, 1H), 0.98-0.94-0.91 (m, 1H). MS found: 461.0 [M+H]$^+$.

Example 7a(+): (+)-N-(5-(Cyclopropanesulfonimidoyl)-4-methylthiazol-2-yl)-2-(2',5'-difluoro-[1,1'-biphenyl]-4-yl)-N-methylacetamide

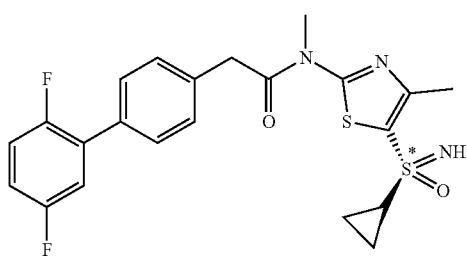

7a(+)

* absolute configuration unknown

Step a)

The racemic mixture 7a resulting from Example 7a, comprising a mixture of the respective enantiomers/stereoisomers was provided.

Step b)

The title compound was prepared by separation of the racemic mixture 7a by chiral SFC chromatography, using as stationary phase Chiralcel OD-3 and as mobile phase 65/35 vol. % CO$_2$/(EtOH/ACN).

The following conditions were applied:

Column: CHIRALCEL OD-3(46*100 mm, 3 um)

Co_Solvent: EtOH/ACN

Column_Temperature: 35

Co_Solvent %: 35

Back_Pressure: 2000 psi

Flow_rate: 2 mL/min

Proc. Chnl. Descr.: PDA 2805 nm (210-400) nm

PDA_Start_Wavelength: 200 nm

PDA_Stop_Wavelength: 400 nm

Example 7a(+) is the enantiomer eluting second (retention time: 2.3 min, FIGS. 2a and 2c).

Said enantiomer is further characterized by a positive specific optical rotation of $[\alpha]^{20}_{Hg365\ nm}$ +83° (c=0.5 g/100 mL, CHCl$_3$), $[\alpha]^{20}_{Na589\ nm}$ +23° (c=1 g/100 mL, CHCl$_3$).

$^1$H-NMR (CDCl$_3$, 400 MHz) δ: 7.54 (d, J=8.0 Hz, 2H), 7.35 (d, J=8.0 Hz, 2H), 7.15-7.08 (m, 2H), 7.02-6.98 (m, 1H), 4.08 (s, 2H), 3.74 (s, 3H), 3.06 (s, 1H), 2.71-2.67 (m, 1H), 1.41-1.36 (m, 1H), 1.31-1.26 (m, 1H), 1.08-1.05 (m, 1H), 0.98-0.94-0.91 (m, 1H). MS found: 461.0 [M+H]$^+$.

Example 7b: N-[5-(Cyclopropylsulfonimidoyl)-4-methyl-thiazol-2-yl]-N-methyl-2-[4-(2-pyridyl)phenyl]acetamide

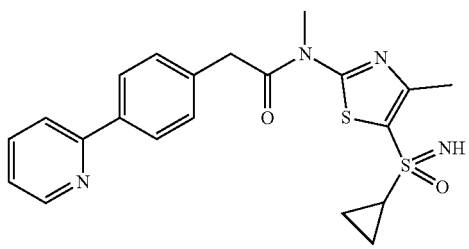

7b

Example 7b was prepared similar as described for Example 7a using 2-(4-(pyridin-2-yl)phenyl)acetic acid in place of 2-(2',5'-difluoro-[1,1'-biphenyl]-4-yl)acetic acid.

$^1$H-NMR (CDCl$_3$, 400 MHz) δ: 8.70-8.68 (m, 1H), 7.99 (d, J=8.4 Hz, 2H), 7.80-7.65 (m, 2H), 7.37 (d, J=8.4 Hz, 2H), 7.30-7.21 (m, 1H), 4.09 (s, 2H), 3.71 (s, 3H), 3.06 (s, 1H), 2.72-2.62 (m, 1H), 2.63 (s, 3H), 1.42-1.22 (m, 2H), 1.10-0.92 (m, 2H). MS found: 427.2 [M+H]$^+$.

The resulting product comprises a mixture of the respective enantiomers/stereoisomers and can be used for preparing the particular enantiomeric compounds according to the present invention, e.g. in step a) of the process of the present invention as described above, by isolating the enantiomers therefrom.

Preparation of Enantiomers of Example Compound 7b

Example 7b(−): (−)-N-(5-(Cyclopropanesulfonimidoyl)-4-methylthiazol-2-yl)-N-methyl-2-(4-(pyridin-2-yl)phenyl)acetamide

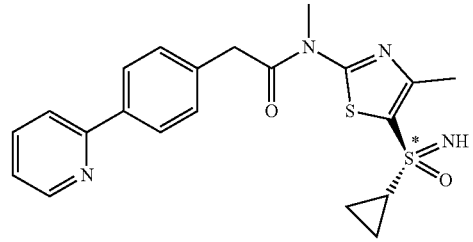

7b(−)

* absolute configuration unknown

Step a)

The racemic mixture 7b resulting from Example 7b, comprising a mixture of the respective enantiomers/stereoisomers was provided.

Step b)

The title compound was prepared by separation of the racemic mixture 7b by chiral SFC chromatography, using as stationary phase Chiralcel OZ-H and as mobile phase 55/45 vol. % CO$_2$/(IPA/ACN, 3:2).

The following conditions were applied:

| | |
|---|---|
| Co-Solvent | IPA:ACN = 3:2 |
| Column | OZ-H 100*4.6 mm 5 um |
| Sample | CD-MIX |
| Sample Well | P1: 5C |
| Column Temperature | 39.9 |
| CO2 Flow Rate | 2.2 |
| Co-Solvent Flow Rate | 1.8 |
| Co-Solvent % | 45 |
| Total Flow | 4 |
| Front Pressure | 156 |
| Back Pressure | 117 |
| Pressure Drop | 39 |
| PDA Start Wavelength | 214 |
| PDA Stop Wavelength | 359 |

Example 7b(−) is the enantiomer eluting first (retention time: 1.8 min, FIGS. 3a and 3b).

Said enantiomer is further characterized by a negative specific optical rotation of $[\alpha]^{20}_{Hg365\ nm}$ −171° (c=1 g/100 mL, CHCl$_3$), $[\alpha]^{20}_{Na589\ nm}$ −24° (c=1 g/100 mL, CHCl$_3$).

$^1$H-NMR (DMSO-d$_6$, 500 MHz) δ: 8.67-8.66 (m, 1H), 8.07 (d, J=8.5 Hz, 2H), 7.97-7.87 (m, 2H), 7.39 (d, J=8.5 Hz, 2H), 7.36-7.34 (m, 1H), 4.65 (s, 1H), 4.22 (s, 2H), 3.71 (s, 3H), 2.82-2.79 (m, 1H), 2.54 (s, 3H), 1.11-1.07 (m, 1H), 0.99-0.91 (m, 3H). MS found: 427.2 [M+H]+.

Example 7b(+): (+)-N-(5-(Cyclopropanesulfonimidoyl)-4-methylthiazol-2-yl)-N-methyl-2-(4-(pyridin-2-yl)phenyl)acetamide

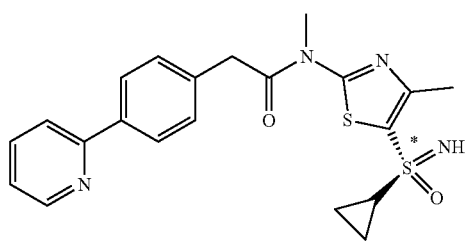

7b(+)

*absolute configuration unknown

Step a)

The racemic mixture 7b resulting from Example 7b, comprising a mixture of the respective enantiomers/stereoisomers was provided.

Step b)

The title compound was prepared by separation of the racemic mixture 7b by chiral SFC chromatography, using as stationary phase Chiralcel OZ-H and as mobile phase 55/45 vol. % CO$_2$/(IPA/ACN, 3:2).

The following conditions were applied:

| | |
|---|---|
| Co-Solvent | IPA:ACN = 3:2 |
| Column | OZ-H 100*4.6 mm 5 um |
| Sample | CD-P2 |
| Sample Well | P1: 5B |
| Column Temperature | 40.1 |
| CO2 Flow Rate | 2.2 |
| Co-Solvent Flow Rate | 1.8 |
| Co-Solvent % | 45 |
| Total Flow | 4 |
| Front Pressure | 157 |
| Back Pressure | 118 |
| Pressure Drop | 39 |
| PDA Start Wavelength | 214 |
| PDA Stop Wavelength | 359 |

Example 7b(+) is the enantiomer eluting second (retention time: 2.8 min, FIGS. 3a and 3c).

Said enantiomer is further characterized by a positive specific optical rotation of $[\alpha]^{20}_{Hg365\ nm}$ +170° (c=1 g/100 mL, CHCl$_3$), $[\alpha]^{20}_{Na589\ nm}$ +22° (c=1 g/100 mL, CHCl$_3$).

$^1$H-NMR (DMSO-d$_6$, 500 MHz) δ: 8.67-8.66 (m, 1H), 8.07 (d, J=8.5 Hz, 2H), 7.97-7.87 (m, 2H), 7.39 (d, J=8.5 Hz, 2H), 7.36-7.34 (m, 1H), 4.65 (s, 1H), 4.22 (s, 2H), 3.71 (s, 3H), 2.82-2.79 (m, 1H), 2.54 (s, 3H), 1.11-1.07 (m, 1H), 0.99-0.91 (m, 3H). MS found: 427.2 [M+H]+.

Example 7c: N-Methyl-N-[4-methyl-5-(methylsulfonimidoyl)thiazol-2-yl]-2-[4-(2-pyridyl)phenyl]acetamide

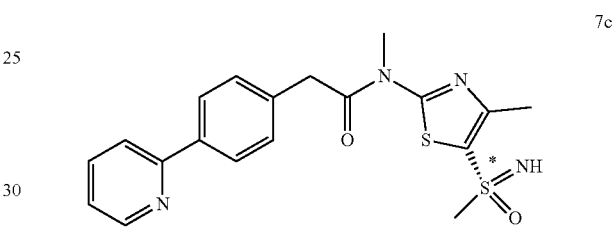

7c

Example 7c was prepared similar as described for Example 7, using 2-(4-(pyridin-2-yl)phenyl)acetic acid in place of 2-(2',5'-difluoro-[1,1'-biphenyl]-4-yl)acetic acid.

$^1$H-NMR (DMSO-d$_6$, 400 MHz) δ: 8.67-8.66 (m, 1H), 8.07 (d, J=8.4 Hz, 2H), 7.97-7.88 (m, 2H), 7.40-7.34 (m, 3H), 4.67 (s, 1H), 4.23 (s, 2H), 3.71 (s, 3H), 3.13 (s, 1H), 2.52 (s, 3H). MS found: 401.1 [M+H]+.

The resulting product comprises a mixture of the respective enantiomers/stereoisomers and can be used for preparing the particular enantiomeric compounds according to the present invention, e.g. in step a) of the process of the present invention as described above, by isolating the enantiomers therefrom.

Preparation of Enantiomers of Example Compound 7c

Example 7c(−): (−)-N-Methyl-N-(4-methyl-5-(S-methylsulfonimidoyl)thiazol-2-yl)-2-(4-(pyridin-2-yl)phenyl)acetamide

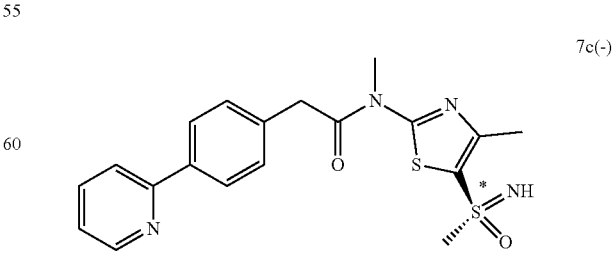

7c(−)

*absolute configuration unknown

The title compound was prepared by separation of the racemic mixture 7c by chiral SFC chromatography, using as stationary phase Chiralcel OD-3 and as mobile phase 70/30 vol. % CO$_2$/(MeOH/ACN, 1:1).

The following conditions were applied:
Column: CHIRALCEL OD-3(4.610 mm, 3 um)
Co_Solvent: ACN/MeOH(1:1)
Column_Temperature: 35
Co_Solvent %: 30
Back_Pressure: 2000 psi
Flow_rate: 2 mL/min
Proc. Chnl. Descr.: PDA 280.0 nm (200-600) nm
PDA_Start_Wavelength: 200 nm
PDA_Stop_Wavelength: 400 nm Example 7c(−) is the enantiomer eluting first (retention time: 5.6 min, FIGS. 4a and 4b).

Said enantiomer is further characterized by a negative specific optical rotation of $[\alpha]^{20}_{Hg365\ nm}$ −19° (c=1 g/100 mL, CHCl$_3$).

$^1$H-NMR (DMSO-d$_6$, 400 MHz) δ: 8.67-8.66 (m, 1H), 8.07 (d, J=8.4 Hz, 2H), 7.97-7.88 (m, 2H), 7.40-7.34 (m, 3H), 4.67 (s, 1H), 4.23 (s, 2H), 3.71 (s, 3H), 3.13 (s, 1H), 2.52 (s, 3H). MS found: 401.1 [M+H]$^+$.

Example 7c(+): (+)-N-Methyl-N-(4-methyl-5-(S-methylsulfonimidoyl)thiazol-2-yl)-2-(4-(pyridin-2-yl)phenyl)acetamide

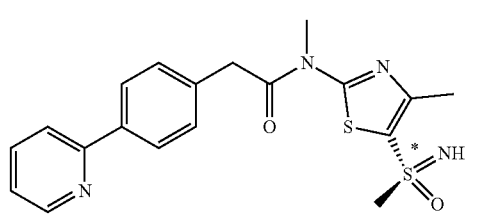

*absolute configuration unknown

Step a)
The racemic mixture 7c resulting from Example 7c, comprising a mixture of the respective enantiomers/stereoisomers was provided.

Step b)
The title compound was prepared by separation of the racemic mixture 7c by chiral SFC chromatography, using as stationary phase Chiralcel OD-3 and as mobile phase 70/30 vol. % CO$_2$/(MeOH/ACN, 1:1).

The following conditions were applied:
Column: CHIRALCEL OD-3(4.6*100 mm, 3 um)
Co_Solvent: ACN/MeOH(1:1)
Column_Temperature: 35
Co_Solvent %: 30
Back_Pressure: 2000 psi
Flow_rate: 2 mL/min
Proc. Chnl. Descr.: PDA 280.0 nm (200-600) nm
PDA_Start_Wavelength: 200 nm
PDA_Stop_Wavelength: 400 nm The Example 7c(+) is the enantiomer eluting second (retention time: 6.0 min, FIGS. 4a and 4c).

Said enantiomer is further characterized by a positive specific optical rotation of $[\alpha]^{20}_{Hg365\ nm}$ +18° (c=1 g/100 mL, CHCl$_3$).

$^1$H-NMR (DMSO-d$_6$, 400 MHz) δ: 8.67-8.66 (m, 1H), 8.07 (d, J=8.4 Hz, 2H), 7.97-7.88 (m, 2H), 7.40-7.34 (m, 3H), 4.67 (s, 1H), 4.23 (s, 2H), 3.71 (s, 3H), 3.13 (s, 1H), 2.52 (s, 3H). MS found: 401.1 [M+H]$^+$.

Example 8: (R)-N-(5-(N-Acetyl-S-methylsulfonimidoyl)-4-methylthiazol-2-yl)-2-(2',5'-difluoro-[1,1'-biphenyl]-4-yl)-N-methylacetamide (8)

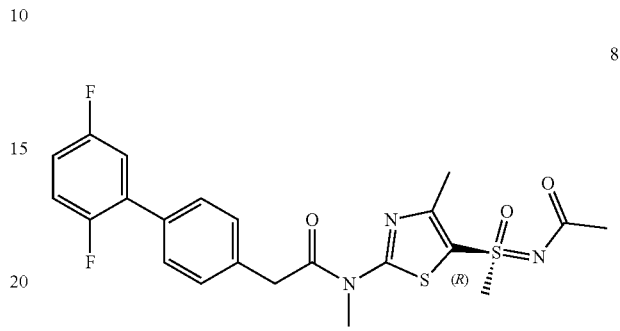

To a solution of the second eluting isomer of Example 7 (400 mg, 0.91 mmol) in DCM (10 mL) was added NEt$_3$ (185 mg, 1.82 mmol). The reaction was stirred for 10 min and then AcCl (107 mg, 1.35 mmol) was added in one portion. After stirring for an additional 30 minutes, the mixture was concentrated in vacuo and purified by prep-HPLC to give Example 8 (280 mg, 63%) as a white solid. $^1$H-NMR (400 MHz, DMSO) δ: 7.57 (d, J=6.8 Hz, 2H), 7.46-7.36 (m, 4H), 7.30-7.25 (m, 1H), 4.26 (s, 2H), 3.75 (s, 3H), 3.53 (s, 3H), 2.53 (s, 3H), 1.97 (s, 3H). MS found: 478.1 [M+H]+.

Determination of the Absolute Stereochemistry:

Compound 8 was crystallized from diisopropyl ether at rt (slow evaporation) to obtain colorless prism. The absolute configuration could be determined properly for the examined crystal to be the (R)-configuration at the acetylated sulfoximine moiety. The Ortep-Plot (50%) of Example 8 with labeling scheme illustrates these findings (FIG. 5).

Crystal data and structure refinement for compound 8:

| | | |
|---|---|---|
| Empirical formula | C22 H21 F2 N3 O3 S2 | |
| Formula weight | 477.54 | |
| Temperature | 110 K | |
| Wavelength | 1.54178 Å | |
| Crystal system | Monoclinic | |
| Space group | P2$_1$ | |
| Unit cell dimensions | a = 10.3167(5) Å | α = 90°. |
| | b = 8.3533(4) Å | β = 96.088(2)°. |
| | c = 13.1044(6) Å | γ = 90°. |
| Volume | 1122.95(9) Å$^3$ | |
| Z | 2 | |
| Density (calculated) | 1.412 Mg/m$^3$ | |
| Absorption coefficient | 2.557 mm$^{-1}$ | |
| F(000) | 496 | |
| Crystal size | 0.16 × 0.08 × 0.04 mm$^3$ | |
| Theta range for data collection | 5.765 to 65.122°. | |
| Index ranges | −12 ≤ h ≤ 12, −9 ≤ k ≤ 9, −15 ≤ l ≤ 15 | |
| Reflections collected | 15475 | |
| Independent reflections | 3791 [R(int) = 0.0190] | |
| Completeness to theta = 65.122° | 99.8% | |
| Absorption correction | Semi-empirical from equivalents | |
| Max. and min. transmission | 0.90 and 0.77 | |
| Refinement method | Full-matrix least-squares on F$^2$ | |
| Data/restraints/parameters | 3791/1/293 | |
| Goodness-of-fit on F$^2$ | 1.060 | |
| Final R indices [I > 2sigma(I)] | R1 = 0.0213, wR2 = 0.0582 | |

| | |
|---|---|
| R indices (all data) | R1 = 0.0214, wR2 = 0.0585 |
| Absolute structure parameter | 0.048(3) |
| Extinction coefficient | n/a |
| Largest diff. peak and hole | 0.216 and −0.188 e.Å$^{-3}$ |

Bond lengths [Å] and angles [°] for compound 8:

| | | | |
|---|---|---|---|
| S(1)—C(16) | 1.735(2) | C(8)—C(9) | 1.388(3) |
| S(1)—C(17) | 1.736(2) | C(8)—H(8) | 0.9500 |
| S(2)—O(2) | 1.4479(15) | C(9)—C(10) | 1.389(3) |
| S(2)—N(3) | 1.5655(18) | C(9)—H(9) | 0.9500 |
| S(2)—C(17) | 1.749(2) | C(10)—C(11) | 1.386(3) |
| S(2)—C(20) | 1.758(2) | C(10)—C(13) | 1.509(3) |
| F(1)—C(1) | 1.363(4) | C(11)—C(12) | 1.386(3) |
| F(2)—C(4) | 1.356(3) | C(11)—H(11) | 0.9500 |
| O(1)—C(14) | 1.220(3) | C(12)—H(12) | 0.9500 |
| O(3)—C(21) | 1.221(3) | C(13)—C(14) | 1.523(3) |
| N(1)—C(14) | 1.375(3) | C(13)—H(13A) | 0.9900 |
| N(1)—C(16) | 1.390(3) | C(13)—H(13B) | 0.9900 |
| N(1)—C(15) | 1.474(3) | C(15)—H(15A) | 0.9800 |
| N(2)—C(16) | 1.306(3) | C(15)—H(15B) | 0.9800 |
| N(2)—C(18) | 1.368(3) | C(15)—H(15C) | 0.9800 |
| N(3)—C(21) | 1.381(3) | C(17)—C(18) | 1.362(3) |
| C(1)—C(2) | 1.378(4) | C(18)—C(19) | 1.496(3) |
| C(1)—C(6) | 1.381(3) | C(19)—H(19A) | 0.9800 |
| C(2)—C(3) | 1.385(4) | C(19)—H(19B) | 0.9800 |
| C(2)—H(2) | 0.9500 | C(19)—H(19C) | 0.9800 |
| C(3)—C(4) | 1.381(3) | C(20)—H(20A) | 0.9800 |
| C(3)—H(3) | 0.9500 | C(20)—H(20B) | 0.9800 |
| C(4)—C(5) | 1.388(3) | C(20)—H(20C) | 0.9800 |
| C(5)—C(6) | 1.398(3) | C(21)—C(22) | 1.499(3) |
| C(5)—C(7) | 1.492(3) | C(22)—H(22A) | 0.9800 |
| C(6)—H(6) | 0.9500 | C(22)—H(22B) | 0.9800 |
| C(7)—C(12) | 1.395(3) | C(22)—H(22C) | 0.9800 |
| C(7)—C(8) | 1.401(3) | | |
| C(16)—S(1)—C(17) | 87.15(10) | N(3)—S(2)—C(20) | 101.41(10) |
| O(2)—S(2)—N(3) | 120.48(9) | C(17)—S(2)—C(20) | 105.19(10) |
| O(2)—S(2)—C(17) | 106.66(9) | C(14)—N(1)—C(16) | 120.05(17) |
| N(3)—S(2)—C(17) | 111.81(10) | C(14)—N(1)—C(15) | 122.54(17) |
| O(2)—S(2)—C(20) | 110.27(10) | C(16)—N(1)—C(15) | 117.42(16) |
| C(16)—N(2)—C(18) | 110.98(17) | C(11)—C(12)—C(7) | 120.99(19) |
| C(21)—N(3)—S(2) | 117.68(14) | C(11)—C(12)—H(12) | 119.5 |
| F(1)—C(1)—C(2) | 119.1(2) | C(7)—C(12)—H(12) | 119.5 |
| F(1)—C(1)—C(6) | 117.5(3) | C(10)—C(13)—C(14) | 112.96(18) |
| C(2)—C(1)—C(6) | 123.4(3) | C(10)—C(13)—H(13A) | 109.0 |
| C(1)—C(2)—C(3) | 117.6(2) | C(14)—C(13)—H(13A) | 109.0 |
| C(1)—C(2)—H(2) | 121.2 | C(10)—C(13)—H(13B) | 109.0 |
| C(3)—C(2)—H(2) | 121.2 | C(14)—C(13)—H(13B) | 109.0 |
| C(4)—C(3)—C(2) | 119.1(2) | H(13A)—C(13)—H(13B) | 107.8 |
| C(4)—C(3)—H(3) | 120.4 | O(1)—C(14)—N(1) | 121.11(18) |
| C(2)—C(3)—H(3) | 120.4 | O(1)—C(14)—C(13) | 122.83(19) |
| F(2)—C(4)—C(3) | 117.0(2) | N(1)—C(14)—C(13) | 116.06(18) |
| F(2)—C(4)—C(5) | 119.0(2) | N(1)—C(15)—H(15A) | 109.5 |
| C(3)—C(4)—C(5) | 123.9(2) | N(1)—C(15)—H(15B) | 109.5 |
| C(4)—C(5)—C(6) | 116.3(2) | H(15A)—C(15)—H(15B) | 109.5 |
| C(4)—C(5)—C(7) | 123.3(2) | N(1)—C(15)—H(15C) | 109.5 |
| C(6)—C(5)—C(7) | 120.3(2) | H(15A)—C(15)—H(15C) | 109.5 |
| C(1)—C(6)—C(5) | 119.6(2) | H(15B)—C(15)—H(15C) | 109.5 |
| C(1)—C(6)—H(6) | 120.2 | N(2)—C(16)—N(1) | 120.74(18) |
| C(5)—C(6)—H(6) | 120.2 | N(2)—C(16)—S(1) | 116.02(15) |
| C(12)—C(7)—C(8) | 117.83(19) | N(1)—C(16)—S(1) | 123.24(15) |
| C(12)—C(7)—C(5) | 119.10(19) | C(18)—C(17)—S(1) | 111.71(16) |
| C(8)—C(7)—C(5) | 123.1(2) | C(18)—C(17)—S(2) | 129.52(16) |
| C(9)—C(8)—C(7) | 120.6(2) | S(1)—C(17)—S(2) | 118.70(12) |
| C(9)—C(8)—H(8) | 119.7 | C(17)—C(18)—N(2) | 114.13(17) |
| C(7)—C(8)—H(8) | 119.7 | C(17)—C(18)—C(19) | 127.9(2) |
| C(8)—C(9)—C(10) | 121.2(2) | N(2)—C(18)—C(19) | 117.95(18) |
| C(8)—C(9)—H(9) | 119.4 | C(18)—C(19)—H(19A) | 109.5 |
| C(10)—C(9)—H(9) | 119.4 | C(18)—C(19)—H(19B) | 109.5 |
| C(11)—C(10)—C(9) | 118.25(19) | H(19A)—C(19)—H(19B) | 109.5 |
| C(11)—C(10)—C(13) | 119.9(2) | C(18)—C(19)—H(19C) | 109.5 |
| C(9)—C(10)—C(13) | 121.9(2) | H(19A)—C(19)—H(19C) | 109.5 |
| C(10)—C(11)—C(12) | 121.1(2) | H(19B)—C(19)—H(19C) | 109.5 |
| C(10)—C(11)—H(11) | 119.4 | S(2)—C(20)—H(20A) | 109.5 |
| C(12)—C(11)—H(11) | 119.4 | S(2)—C(20)—H(20B) | 109.5 |
| H(20A)—C(20)—H(20B) | 109.5 | C(21)—C(22)—H(22A) | 109.5 |
| S(2)—C(20)—H(20C) | 109.5 | C(21)—C(22)—H(22B) | 109.5 |
| H(20A)—C(20)—H(20C) | 109.5 | H(22A)—C(22)—H(22B) | 109.5 |
| H(20B)—C(20)—H(20C) | 109.5 | C(21)—C(22)—H(22C) | 109.5 |

-continued

| | | | |
|---|---|---|---|
| O(3)—C(21)—N(3) | 125.8(2) | H(22A)—C(22)—H(22C) | 109.5 |
| O(3)—C(21)—C(22) | 121.8(2) | H(22B)—C(22)—H(22C) | 109.5 |
| N(3)—C(21)—C(22) | 112.37(18) | | |

Torsion angles [°] for compound 8:

| | | | |
|---|---|---|---|
| O(2)—S(2)—N(3)—C(21) | 62.35(19) | C(9)—C(10)—C(11)—C(12) | −0.2(3) |
| C(17)—S(2)—N(3)—C(21) | −64.09(18) | C(13)—C(10)—C(11)—C(12) | −179.3(2) |
| C(20)—S(2)—N(3)—C(21) | −175.72(16) | C(10)—C(11)—C(12)—C(7) | 0.6(3) |
| F(1)—C(1)—C(2)—C(3) | 179.8(2) | C(8)—C(7)—C(12)—C(11) | −0.7(3) |
| C(6)—C(1)—C(2)—C(3) | 0.1(4) | C(5)—C(7)—C(12)—C(11) | −179.9(2) |
| C(1)—C(2)—C(3)—C(4) | −0.3(4) | C(11)—C(10)—C(13)—C(14) | −110.6(2) |
| C(2)—C(3)—C(4)—F(2) | 179.1(2) | C(9)—C(10)—C(13)—C(14) | 70.4(3) |
| C(2)—C(3)—C(4)—C(5) | 0.4(4) | C(16)—N(1)—C(14)—O(1) | 1.7(3) |
| F(2)—C(4)—C(5)—C(6) | −179.0(2) | C(15)—N(1)—C(14)—O(1) | −178.5(2) |
| C(3)—C(4)—C(5)—C(6) | −0.3(3) | C(16)—N(1)—C(14)—C(13) | −178.76(18) |
| F(2)—C(4)—C(5)—C(7) | −1.0(3) | C(15)—N(1)—C(14)—C(13) | 1.1(3) |
| C(3)—C(4)—C(5)—C(7) | 177.7(2) | C(10)—C(13)—C(14)—O(1) | −3.6(3) |
| F(1)—C(1)—C(6)—C(5) | −179.7(2) | C(10)—C(13)—C(14)—N(1) | 176.87(18) |
| C(2)—C(1)—C(6)—C(5) | 0.0(4) | C(18)—N(2)—C(16)—N(1) | −179.56(18) |
| C(4)—C(5)—C(6)—C(1) | 0.1(3) | C(18)—N(2)—C(16)—S(1) | −0.4(2) |
| C(7)—C(5)—C(6)—C(1) | −178.0(2) | C(14)—N(1)—C(16)—N(2) | 177.30(19) |
| C(4)—C(5)—C(7)—C(12) | −145.5(2) | C(15)—N(1)—C(16)—N(2) | −2.5(3) |
| C(6)—C(5)—C(7)—C(12) | 32.4(3) | C(14)—N(1)—C(16)—S(1) | −1.8(3) |
| C(4)—C(5)—C(7)—C(8) | 35.3(3) | C(15)—N(1)—C(16)—S(1) | 178.33(16) |
| C(6)—C(5)—C(7)—C(8) | −146.7(2) | C(17)—S(1)—C(16)—N(2) | −0.11(16) |
| C(12)—C(7)—C(8)—C(9) | 0.4(3) | C(17)—S(1)—C(16)—N(1) | 179.05(18) |
| C(5)—C(7)—C(8)—C(9) | 179.6(2) | C(16)—S(1)—C(17)—C(18) | 0.56(16) |
| C(7)—C(8)—C(9)—C(10) | −0.1(3) | C(16)—S(1)—C(17)—S(2) | 177.73(13) |
| C(8)—C(9)—C(10)—C(11) | 0.0(3) | O(2)—S(2)—C(17)—C(18) | −177.55(19) |
| C(8)—C(9)—C(10)—C(13) | 179.0(2) | N(3)—S(2)—C(17)—C(18) | −43.9(2) |
| C(20)—S(2)—C(17)—C(18) | 65.3(2) | S(1)—C(17)—C(18)—C(19) | 177.80(18) |
| O(2)—S(2)—C(17)—S(1) | 5.86(15) | S(2)—C(17)—C(18)—C(19) | 1.0(3) |
| N(3)—S(2)—C(17)—S(1) | 139.50(12) | C(16)—N(2)—C(18)—C(17) | 0.8(3) |
| C(20)—S(2)—C(17)—S(1) | −111.27(13) | C(16)—N(2)—C(18)—C(19) | −178.03(18) |
| S(1)—C(17)—C(18)—N(2) | −0.9(2) | S(2)—N(3)—C(21)—O(3) | −0.3(3) |
| S(2)—C(17)—C(18)—N(2) | −177.69(16) | S(2)—N(3)—C(21)—C(22) | 179.43(16) |

Example 9: Tert-Butyl ((4-(bromomethyl)-2-(2-(2', 5'-difluoro-[1,1'-biphenyl]-4-yl)-N-methylacetamido)thiazol-5-yl)(methyl)(oxo)-16-sulfaneylidene)carbamate Example 10: 2-(2',5'-Difluoro-[1,1'-biphenyl]-4-yl)-N-(4-(hydroxymethyl)-5-(S-methylsulfon-imidoyl)thiazol-2-yl)-N-methylacetamide

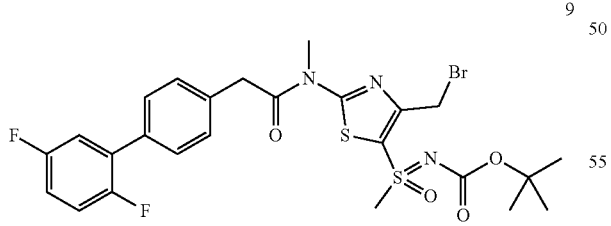

To a solution of Example 6 (1.50 g, 2.80 mmol) in CHCl₃ (50 mL) was added N-bromosuccinimide (524 mg, 2.94 mmol) and benzoyl peroxide (136 mg, 0.56 mmol). The solution was stirred at 70° C. for 2 h, colled to rt, quenched with sat. Na₂S₂O₃ (50 mL) and extracted with DCM (3×100 mL). The combined organic layer was concentrated and purified by FCC (EA:PE=1:2) to give Example 9 as white solid.

To a solution of Example 9 (600 mg, 0.98 mmol) in 1,4-dioxane (15 mL) was added H₂O (10 mL) (396 mg, 2.40 mmol) and then stirred at 100° C. overnight, cooled and extracted with EtOAc (3×100 mL). The combined organic layer was concentrated and purified by FCC (EA:PE=1:1) to give Example 10 as white solid.

Preparation of Enantiomers of Example Compound 10

Example 10a: 2-(2',5'-Difluoro-[1,1'-biphenyl]-4-yl)-N-(4-(hydroxymethyl)-5-(S-methylsulfonimidoyl)thiazol-2-yl)-N-methylacetamide (First Isolated Enantiomer)

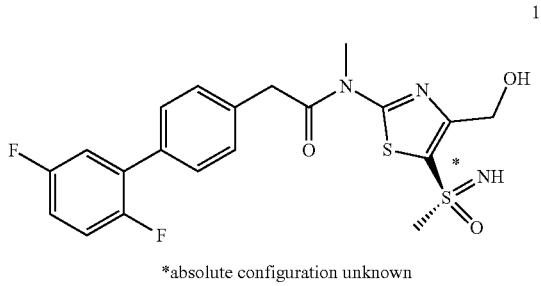

*absolute configuration unknown

The title compound was prepared by separation of the racemic mixture 10, resulting from Example 10, by chiral SFC chromatography, using the following instrument and conditions:
Instrument: SFC-80 (Thar, Waters)
Column name: OZ 20×250 nM, 10 µM (Daicel)
Column temperature: 35° C.
Flow rate: 80 g/min
Back pressure: 100 bar
Cycle time: 4 min
Sample solution: 0.37 g dissolved in 30 mL MeOH
Injection volume: 1 mL
The Example 10a is the first eluting enantiomer (retention time: 2.3 min, FIGS. 6a and 6b).
$^1$H-NMR (500 MHz, DMSO-$d_6$) δ: 7.57 (dd, J=1.3, 7.8 Hz, 2H), 7.45-7.36 (m, 4H), 7.29-7.25 (m, 1H), 5.25 (t, J=5.8 Hz, 1H), 4.78 (s, 1H), 4.75-4.64 (m, 2H), 4.25 (s, 2H), 3.75 (s, 3H), 3.21 (d, J=0.5 Hz, 3H). MS found: 452.1 [M+H]+.

Example 10b: 2-(2',5'-Difluoro-[1,1'-biphenyl]-4-yl)-N-(4-(hydroxymethyl)-5-(S-methylsulfonimidoyl)thiazol-2-yl)-N-methylacetamide (Second Isolated Enantiomer)

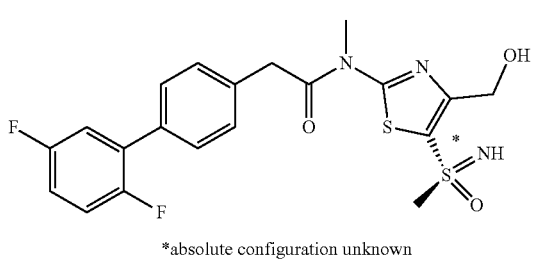

*absolute configuration unknown

The Example 10b is the second eluting enantiomer (retention time: 2.9 min, FIGS. 6a and 6c).
$^1$H-NMR and MS corresponds to Example 10a.
Biological Assays
The novel compounds according to the invention exhibit an unforeseeable surprising spectrum of action. They exhibit not only an antiviral action especially against representatives of the herpes viridae group, particularly against herpes simplex viruses (HSV) but also improved solubility and a reduced carbonic anhydrase activity. These compound characteristics lead to an improved pharmacokinetic profile of the novel compounds of the present invention and consequently profound antiviral activity in vivo. They are thus suitable for the treatment and prophylaxis of disorders which are caused by viruses especially herpes viruses, in particular disorders which are caused by herpes simplex viruses.

The novel compounds according to the invention exhibit an unforeseeable surprising reduced carbonic anhydrase activity.

The novel compounds thus show no or at least reduced off-target activity, in particular no or reduced side effects caused by carbonic anhydrase activity such as urothelial hyperplasia or diuretic pharmacological activity (G. Durand-Cavagna et al. *Fund. Appl. Toxicol.* 1992:18, 137).

The increased solubility improves formulation of the compounds, improves ADME characteristics and especially formulations used for intravenious applications.

The aqueous solubility (PBS, pH 7.4) was determined at Eurofins, Cerep, Panlabs according to C. A. Lipinski et al. *Adv. Drug Del. Rev.* 1997:46, 3.

In-Vitro Activity
Viruses and Cells:
HSV (HSV-1 Walki, HSV-1F, HSV-2 MS, HSV clinical isolates and HSV resistant strains) was cultivated on Vero cells (ATCC CCL-81) under the following conditions: The cells were grown in M199 medium (5% foetal calf serum, 2 mM glutamine, 100 IU/mL penicillin, 100 µg/mL streptomycin) in cell culture bottles at 37° C. and 5% $CO_2$. The cells were splitted twice per week (1:4). For the infection, the medium was removed, the cells were washed with Hank's solution, detached using 0.05% trypsin, 0.02% EDTA and incubacted at a density of 4×10$^5$ cells/mL under the above-mentioned conditions for 24 h. The medium was removed and the virus solution was added at an m.o.i of <0.05 in a volume of 2 mL per 175 cm$^2$ surface. The infected cells were incubated at 37° C., 5% $CO_2$ for 1 h and then the medium was made up to a volume of 50 mL per 175 cm$^2$ bottle. 3 days after the infection, the cultures showed clear signs of a cytopathic effect. The virus was released by freezing (−80° C.) and thwawing (37° C.) the infected cultures twice. Cell debris was removed by centrifugation (300 g, 10 min, 4° C.) and the supernatant was frozen in aliquots at −80° C.

The virus titre was determined using a plaque assay. To this end, Vero cells were seeded in 24-well plates at a density of 4×10$^5$ cells per well and, after 24 h of incubation (37° C., 5% $CO_2$) infected with 100 µL of inoculum (dilutions (10$^{-2}$ to 10$^{-12}$) of the virus stock). 1 h after the infection, the medium was removed and the cells were covered with 1 mL of overlay medium (0.5% methylcellulose, 0.22% sodium bicarbonate, 2 mM glutamine, 100 IU/mL penicillin, 100 µg/mL streptomycin, 5% foetal calf serum in MEM-Eagle medium with Earl's salt) and incubated for 3 d in a cell incubator at (37° C., 5% $CO_2$). The cells were then fixated using 4% formaline for 1 h, washed with water, stained with Giemsa for 30 min and then washed and dried. Using a plaque viewer, the virus titre was determined. The stocks used for the experiments had a titre of 1×10$^5$/mL up to 1×10$^8$/mL.

The antiviral action was determined using a patented (DE10235967 and WO2004/015416) and subsequently published activity selectivity assay (G. Kleymann et al. J. Biomol. Screen. 2004; 9, 578) in 96- or 384-well mictrotitre plates using various cell lines of neuronal, lymphoid and epithelial origin, such as, for example, Vero (african green monkey kidney cells), MEF (murine embryonal fibroblasts), HELF (human embryonal fibroblasts), NT2 (human neuronal cell line) or Jurkat (human lymphoid T-cell line). The relevant experimental details of the above mentioned patent and publication to evaluate the antiviral activity of the invention (disclosed compounds) are described below.

The effect of the substances on the spreading of the cytopathogenic effect was determined in comparision to the reference compound acyclovir-sodium (Zovirax™), a clinically approved anti-herpes chemotherapeutic.

The compounds (50 mM stock solution dissolved in DMSO) are examined on microtitre plates (for example 96-well flat bottom cell culture plates) at a final concentration of 250 to 0.5 µM or, in case of potent antiviral compounds, 250 to 0.5 nM in 2 to 4 replications (4 to 2 substances per plate). Also examined are toxic and cytostatic effects or precipitation of the compounds. After an appropriate dilution of the compounds (1:2) on the microtitre plate in the appropriate medium (100 µL), a suspension of cells (50 µL, 1×10$^4$ cells per well), such as, for example of Vero cells in M199 (medium 199 with 5% foetal calf serum, 2 mM glutamine and optionally 100 IU/mL penicillin and 100 µg/mL streptomycin) or of MEF or HELF cells in EMEM (Eagle's Minimum Essential Medium with 10% foetal calf serum, 2 mM glutamine and optionally 100 IU/mL penicillin and 100 µg/mL streptomycin), or of NT2- and Jurkat cells in DMEM ((4.5 mg/L glucose plus pyridoxin) with 10% foetal calf serum, 2 mM glutamine, 1 mM sodium pyruvate, non-essential amino acids and optionally 100 IU/mL penicillin and 100 µg/mL streptomycin) is added to each well and the cells in the relevant wells are infected with the appropriate amount of virus (HSV-1 or HSV-2 having an m.o.i (multiplicity of infection) of 0.0025 for Vero, HELF and MEF cells and an m.o.i. of 0.1 for NT2 and Jurkat cells). The plates are then incubated at 37° C. in a cell $CO_2$ incubator (5% $CO_2$) for several days. After this time, the cell lawn of, for example, Vero cells in the substance-free virus controls, starting from 25 infections centres, is completely destroyed or lysed by the cytopathogenic effect (CPE) of the herpes viruses (100% CPE). The plates are initially evaluated visually using a microscope and then analysed using a fluorescent dye. To this end, the cell supernatant of all wells of the MTP is aspirated and the wells are filled with 250 µL PBS (phosphate buffered saline) wash solution. The PBS is then aspirated and all the wells are filled with 200 µL of fluorescent dye solution (fluroescein diacetate, 10 µg/mL in PBS). After an incubation time of 30 to 90 min, the test plates are read in a fluorescence detector at an excitation wavelength of 485 nm and an emission wavelength of 538 nm. Here, $IC_{50}$ is the half-maximal fluorescence intensity with respect to the non-infected cell control (100% value). The $IC_{50}$ value [%] ((compound treated infected cells minus non treated virus infected cells) divided by (cell control or Zovirax treated infected cells minus non treated infected cells)×100) can also be referenced to a suitable active compound control (see description of the assay: infected cells in the presence of suitable concentrations of an antiviral compound such as, for example, Zovirax 20 µM). This active compound control reaches fluorescence intensities of about 85 to 100% with respect to the non-infected cell control. The results for some Example compounds, comprising a mixture of the respective enantiomers (indicated in Table 1 by #) as well as of the separated and isolated (+) and (−) enantiomers of Examples 7, 7a, 7b and 7c above are summarized in TABLE 1 below:

TABLE 1

| Example | $IC_{50}$ (HSV-1 infected Vero) | $IC_{50}$ (HSV-2 infected Vero) | $IC_{50}$ (HSV-1 ACV resistant) |
|---|---|---|---|
| 7# | 25-100 nM | 25-100 nM | 25-100 nM |
| 7(−) | 10-50 nM | 10-50 nM | 10-50 nM |
| 7(+) | 30-200 nM | 30-200 nM | 30-200 nM |
| 7a# | 30-100 nM | 50-500 nM | 30-100 nM |
| 7a(−) | 20-50 nM | 30-300 nM | 20-50 nM |
| 7a(+) | 250-750 nM | 500-2000 nM | 250-750 nM |
| 7b# | 100-400 nM | 250-1000 nM | 100-400 nM |
| 7b(−) | 75-250 nM | 200-750 nM | 75-250 nM |
| 7b(+) | 500-1500 nM | 2000-8000 nM | 500-1500 nM |
| 7c# | 150-600 nM | 200-1500 nM | 150-600 nM |
| 7c(−) | 75-300 nM | 100-750 nM | 75-300 nM |
| 7c(+) | 0.3-0.75 µM | 0.5-1.5 µM | 0.3-0.75 µM |
| 8 | 10-50 µM | 50-250 µM | 10-50 µM |
| 10a | 50-250 nM | 1-5 µM | 50-250 nM |
| 10b | 1-5 µM | 5-25 µM | 1-5 µM |
| Acyclovir | 0.5-3 µM | 0.5-3 µM | >25 µM |

Preference is given to antiviral compounds according to the invention whose $IC_{50}$ (HSV-1/Vero) in the activity selectivity assay described above is preferably below 100 µM, more preferably below 10 µM and very particularly preferable below 1 µM.

As shown in Table 1, the Examples 7, 7a, 7b and 7c show antiviral activity even if present as mixtures of the respective enantiomers. Further, Examples 7, 7a, 7b and 7c show antiviral activity also for the isolated enantiomers, which supports, that the individual enantiomers will also exhibit antiviral activity.

The results further show, that surprisingly the enantiomers with a counterclockwise levo or negative specific rotation exhibit more potent antiviral activity compared to the racemate and enantiomers with a clockwise dextro or positive specific rotation.

The results also show, that surprisingly the 7(−) enantiomer with the absolute (S)-configuration exhibit more potent antiviral activity compared to the racemate and 7(+) enantiomer with the absolute (R)-configuration.

The novel compounds according to the invention are thus useful active compounds for the treatment and prophylaxis of disorders caused by viruses, in particular herpes viruses and very particularly herpes simplex viruses. Particularly active enantiomers are those showing a negative specific optical rotation and which elute first on the defined chiral column in case of 7(−) the absolute configuration is (S), as those are at least a factor of two more potent than the respective enantiomers with opposite absolute configuration (R) with a specific positive optical rotation and which elute second on the defined chiral column in case of 7(+).

Examples of indication areas which may be mentioned are:

1) Treatment and prophylaxis of herpes infections, in particular herpes simplex infections in patients displaying herpes disease such as herpes labialis, herpes genitalis and herpes-related keratitis, Alzheimer's disease, encephalitis, pneumonia, hepatitis or viral shedding etc.

2) Treatment and prophylaxis of herpes infections, in particular herpes simplex infections, in patients with a suppressed immune system (for example AIDS patients, cancer patients, patients having a genetic or inherited immunodeficiency, transpant patients).

3) Treatment and prophylaxis of herpes infections, in particular herpes simplex infections, in new-born children and infants 4) Treatment and prophylaxis of herpes infections, in particular herpes simplex infections, and in herpes-positive patients, in particular herpes-simplex-positive patients, for suppressing recurrence or viral shedding (suppression therapy).

5) Treatment and prophylaxis of herpes infections, in particular herpes simplex infections, and in herpes-positive patients, in particular herpes-simplex-positive patients, resistant to nucleosidic antiviral therapy such as acyclovir, penciclovir, famciclovir, ganciclovir, valacyclovir etc.

Carbonic Anhydrase Activity

Carbonic anhydrase II activity and its respective inhibition was performed according to R. Iyer et al. *J. Biomol. Screen.* 2006:11, 782 or in the case of carbonic anhydrase I activity according to A. R. Katritzky et al. *J. Med. Chem.* 1987:30, 2058 based on human starting material.

A protocol for determination of the carbonic anhydrase enzymatic activity at rt using the pH indicator method is described below:

1 µL inhibitor (50 mM stock solution in DMSO) is diluted to a final test concentration ranging from 100 µM down to 1 nM (or 1 µL water in controls) and incubated for 2 min with 0.5 to 2 EU human Carboanhydrase I (180 U/mg) in 400 µL water and 200 µL phenol red indicator solution (20 mg/L). An enzymactic unit (EU) is defined as an amount which doubles the non catalyzied rate. The hydration reaction is initiated by adding 100 µL 0.5M bicarbonate buffer (0.3M $Na_2CO_3$; 0.2M $NaHCO_3$) and subsequent dumping of $CO_2$ through a needle (0.7×30 mm; 22 G×1.25) into the assay solution at a rate of 10 mL gas/minute. The time to colour change (pH 7.2) is determined with a microchronometer or stop watch.

The percentage of inhibition is calculated as described below:

(time to color change without enzyme−time to color change with enzyme and inhibitor)/(time to color change without enzyme−time to color change with enzyme).

$IC_{50}$-values (inhibitory concentration) reflect the molar amount of inhibitor, which reduces the EU-activity in the test system by 50%.

In the test system no or significantly reduced carbonic anhydrase inhibition is detected for Example 7, 7(−), 7(+), 7c, 7c(−), 7c(+) and 7b. In contrast to this finding Example 87 (WO2001/047904) shows carbonic anhydrase inhibition in the range of 1 to 3 µM ($IC_{50}$).

Example compounds, comprising a mixture of the respective enantiomers have been indicated in Table 2 by #.

As shown in Table 2, the Examples 7, 7b and 7c show no or reduced carbonic anhydrase inhibition even if present as mixtures of the respective enantiomers. Further, for Examples 7 and 7c also the isolated enantiomers show no or reduced carbonic anhydrase inhibition. This shows, that the individual enantiomers will also exhibit no or reduced carbonic anhydrase inhibition (even if not explicitly shown herein as e.g. for Example 7b).

Results are shown below in TABLE 2:

TABLE 2

| Example | $IC_{50}$ (µM) Human Carboanhydrase II |
|---|---|
| 7# | >10 |
| 7(−) | >10 |

TABLE 2-continued

| Example | $IC_{50}$ (µM) Human Carboanhydrase II |
|---|---|
| 7(+) | >10 |
| 7c# | >10 |
| 7c(−) | >10 |
| 7c(+) | >10 |
| 7b# | >10 |
| reference example 87 (WO2001/47904) | 1.7 |
| acetazolamide | 0.026 |

Aqueous Solubility (PBS, pH 7.4)

Measurement of the aqueous solubility was performed according to Lipinski, C. A. et al. *Adv. Drug Del. Rev.* 1997:46, 3. The relevant information from the literature is described below.

Aqueous solubility (µM, shake flask, 24 h incubation, rt) of a compound (10 mM Stock in DMSO) was determined by comparing the peak area (HPLC-UV/VIS) of the principal peak in a calibration standard (200 µM) containing organic solvent (methanol/water, 60/40, v/v) with the peak area of the corresponding peak in a buffer sample (PBS, pH 7.4). In addition, chromatographic purity (%) was defined as the peak area of the principal peak relative to the total integrated peak area in the HPLC chromatogram of the calibration standard.

In the aqueous solubility test system significantly increased solubility (at least one order of mangitude) is detected for Example 7 in comparison to Example 87 (WO2001/047904).

Example compounds, comprising a mixture of the respective enantiomers have been indicated in Table 3 by #.

Results are shown below in TABLE 3:

TABLE 3

| Example | Solubility [µM] (PBS, pH 7.4, 200 µM Test concentration) | Wavelength of Dectection [nm] | Chromatographic Purity [%] |
|---|---|---|---|
| 7# | 5 | 260 | 100 |
| reference example 87 (WO2001/47904) | 0.7 | 260 | 100 |
| Simvastatin | 18.7 | 230 | 100 |

Similarly good solubility can be expected for the individual enantiomers.

Mechanism of Action

To elucidate the mechanism of action compound resistant herpesviruses were selected in the presence of e.g. 2 µM of Example 7(−) or Example 7c(−) according to G. Kleymann et al. *Nat. Med.* 2002; 8, 392.

The viral DNA was prepared as described and used as template in a subsequent PCR reaction employing the following method parameters: 5 min denaturation 95° C., 35 cycles 95° denaturation 30 sec, annealing 60° C. 30 sec, amplification/extension 72° C. 30 sec, final step 5 min 72° C. then cool to 4-5° C.; PCR primers: Primer rev HSV1/2 (5' atgagccgcgacaggaac 3'), Primer fwd HSV1/2 (5' ggtggatgattaacgccctg 3'). The amplified products (~849 bp in size) were purified by 1% agarose gel-electrophoresis and subsequently sequenced using the sequencing primer (5' ttaacgccctgtaccacacc 3'). Sequencing revealed the resistance conferring mutations K356Q and K356R in the helicase gene of HSV-1 compared to the sensitive strain used as the starting material to selected resistant viruses in the presence of said compounds Example 7(−) and 7c(−). Mutation K356R is new and has not been described to date for HHV-1.

In Vivo Activity

Pharmacokinetics

Pharmcokinetic parameters were determined for Example 7, 7(−), 7(+) and 7c in male mice strain C57BL/6J at an intraveneous (i.v.) dose of 5 mg/kg (5% DMSO in heterologous plasma, 2.5 mL/kg) and an oral dose (p.o) of 10 mg/kg (DMSO/0.5% HPMC (5:95), 5 mL/kg).

Surprisingly the enantiomers with a specific optical negative rotation can show a better pharmacokinetic profile, exemplified by Example 7c(−), which demonstrates the highest exposure in mice strain C57BL/6J with respect to $C_{max}$ (6647 ng/mL) and AUC (38034 ng*h/mL) at 10 mg/kg p.o (DMSO/0.5% HPMC (5:95), 5 mL/kg) compared to the racemate (Example 7c, $C_{max}$ 4289 ng/mL, AUC 22482 ng*h/mL) and the opposite enantiomer (Example 7c(+), $C_{max}$ 5704 ng/mL, AUC 31237 ng*h/mL) with a specific positive optical rotation. Furthermore especially Example 7 shows the highest brain exposure (~13-14 μM, 6000 ng/g brain) enabling treatment of herpes encephalitis.

Animal Model

Animal experiments were performed according to patent WO2001/047904 or subsequent publications (U. A. K. Betz et al. *Antimicrob. Agents Chemother.* 2002:46, 1766 or G. Kleymann et al. *Nat. Med.* 2002; 8, 392). The relevant experimental details of the above mentioned patent and publication to evaluate the antiviral activity of the invention (disclosed compounds) in-vivo (animal models) are described below.

Animals:

6 week-old female mice, BALB/cABom strain were obtained from a commercial breeder.

Infection: The animals were anaesthetized with $Et_2O$ in a sealed glass vessel. 50 μL of a dilution of the virus stock (infection dose $5 \times 10^4$ PFU (Plaque forming units)) were introduced into the nose of the anaesthetized animals using a pipette. In 90 to 100% of the animals, this infection dose causes death by generalized infection with prominent repiratory and central-nervous symptoms on average after 5 to 8 days.

Treatment and Assessment:

6 hours after infection animals were treated with doses of 0.1-150 mg/kg of body mass, 3 times per day at 7 am, 2 μm and 7 μm (tid) or 2 times per day at 7 am and 7 μm (bid) or once daily at 1 μm (od) for a period of 5 days. The compounds were pre-dissolved in DMSO and resuspended in 0.5% HPMC (hydroxypropylmethylcellulose) in water or PBS (DMSO/0.5% HPMC (max 5:95 ideally 1.5% DMSO, 0.5% HPMC in water or PBS)). After the last administration, the animals were monitored further and the time of death was determined.

A comparison of survival curves showed for the compound of Example 7, for example, an $ED_{50}$ of less than 10 mg/kg for HSV-1 or HSV-2, were $ED_{50}$ means that 50% of the infected animals survive at this dose. In particular enantiomer Example 7(−) shows an $ED_{50}$ of less than 5 mg/kg for HSV-1.

However, from the in vivo data for Example 7, even if tested herein as a mixture of the respective enantiomers, activity of the individual enantiomers can also be expected.

The novel active enantiomers of the present invention can be converted in a known manner into customary formulations, such as tablets, caplets, sugar-coated tablets, pills, granules, aerosols, syrups, pharmaceutically suitable carriers and solvents. Here, the therapeutically active compound should in each case be present in a concentration of about 0.1 to 90% by weight of the total mixture, i.e. in amounts which are sufficient to achieve the dosage range indicated.

The formulations are prepared, for example, by extending the active compounds with solvents and/or excipients, if appropriate using emulsifiers and/or dispersants, if being possible, for example, if the diluent used is water, to use, if appropriate, organic solvents as auxiliary solvents.

Administration is carried out in a customary manner, preferably orally, parenterally or topically, in particular perlingually or intravenously.

In the case of parenteral administration, solutions of the active compounds using suitable liquid carrier materials can be employed.

In general, it has proved advantageous in the case or intravenous administration to administer amounts of from approx. 0.001 to 20 mg/kg, preferably approx. 0.01 to 10 mg/kg of bodyweight to achieve effective results, and in the case of oral administration the dose is approx. 0.01 to 30 mg/kg, preferably 0.1 to 20 mg/kg of body weight.

In spite of this, it may be necessary, if appropriate, to depart from the amounts mentioned, namely depending on the bodyweight or on the type of the administration route, on the individual response to the medicament, the manner of its formulation and the time or interval at which administration takes place. Thus, in some cases it may be adequate to manage with less than the abovementioned minimum amount, while in other cases the upper limit mentioned must be exceeded. In the case of administration of relatively large amounts it may be advisable to divide this into several individual administrations over the course of the day.

If appropriate, it may be useful to combine the compounds according to the invention with other active substances, in particular antiviral active compounds, so called combination therapy.

SEQUENCE LISTING

Figure 1A:
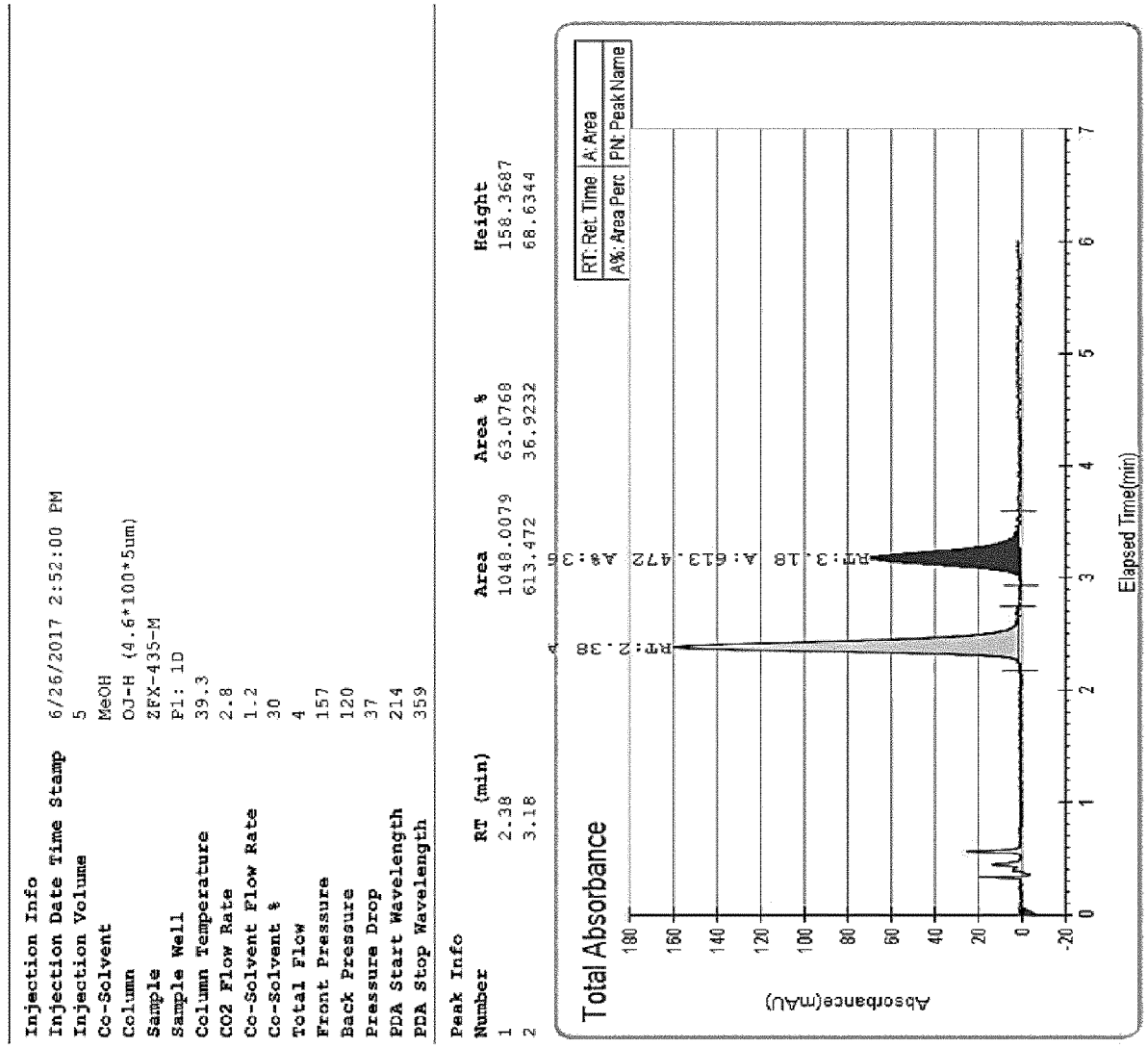
FIG. 1a: Chiral SFC chromatogram of a mixture of Example 7(−) and 7(+).
Figure 1B:
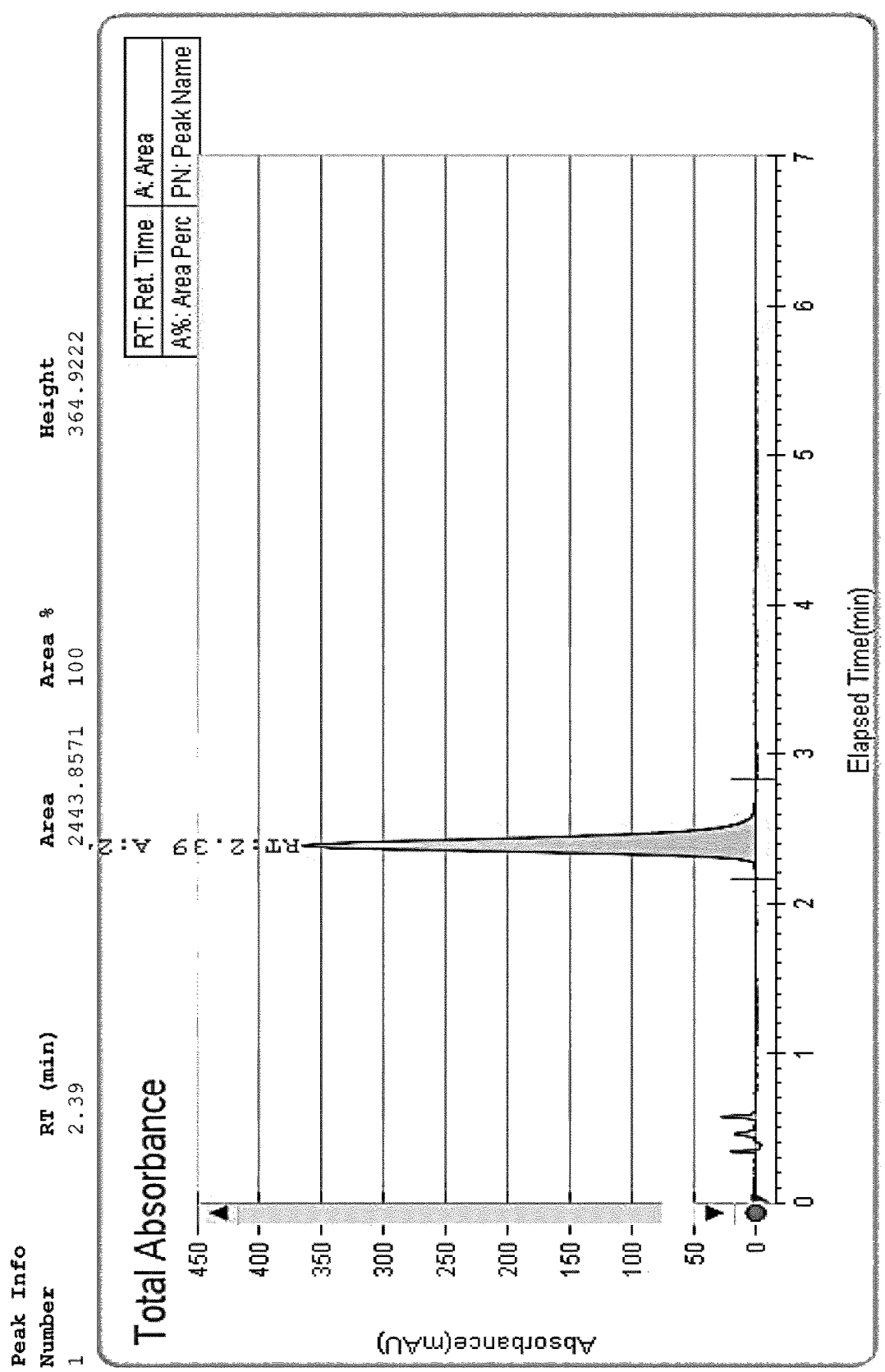
FIG. 1b: Chiral SFC chromatogram of Example 7(−).
Figure 1C:
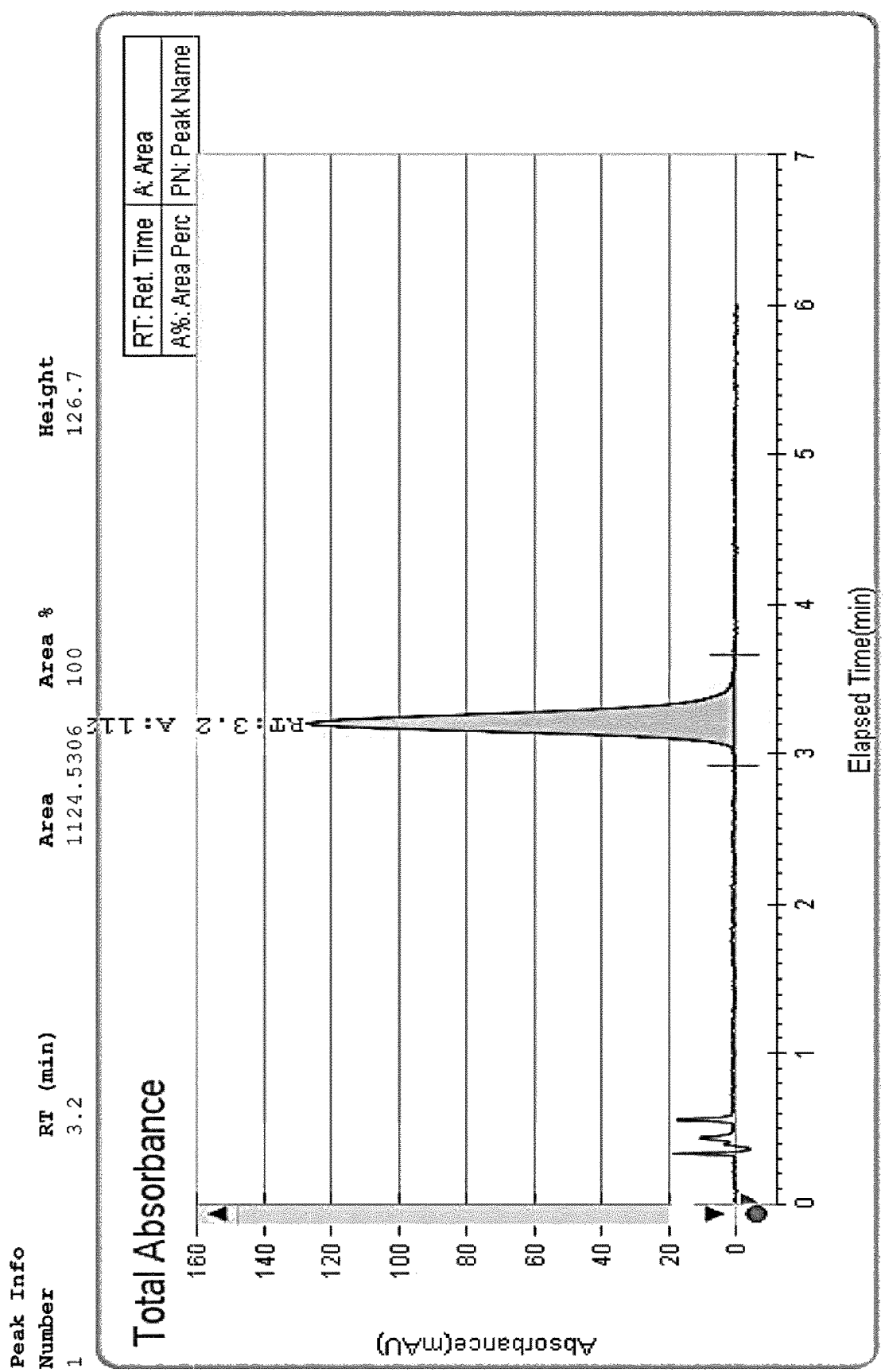
FIG. 1c: Chiral SFC chromatogram of Example 7(+).
Figure 2A:
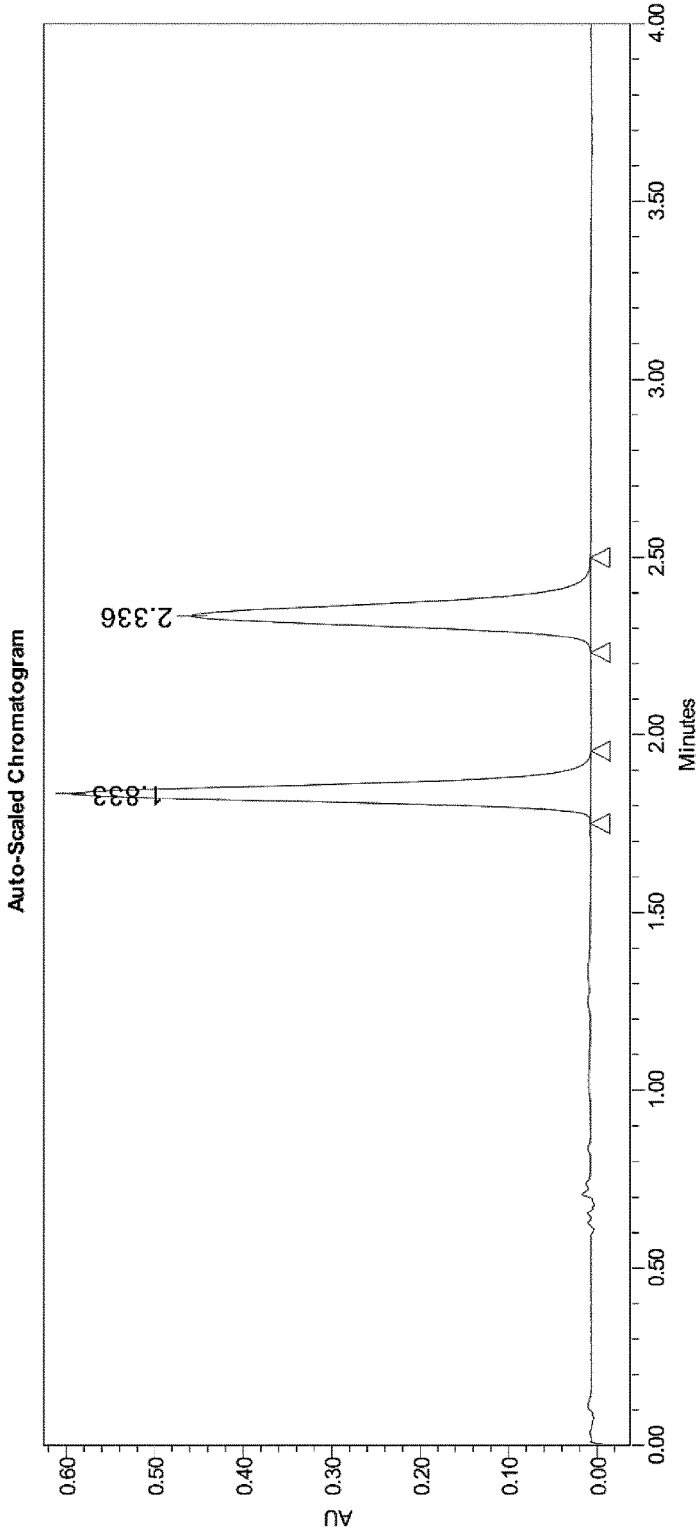
FIG. 2a: Chiral SFC chromatogram of a racemic mixture of 7a(−) and 7a(+).
Figure 2B:
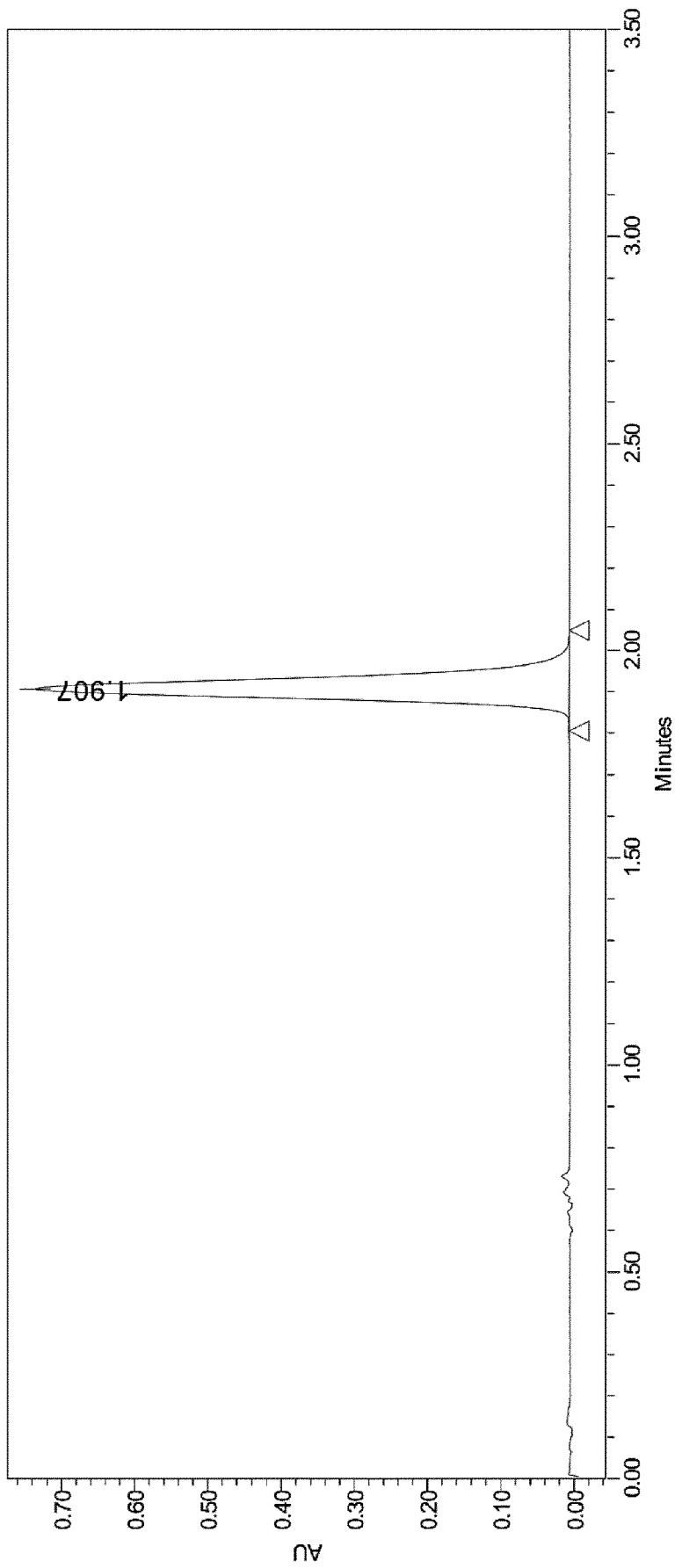
FIG. 2b: Chiral SFC chromatogram of 7a(−).
Figure 2C:
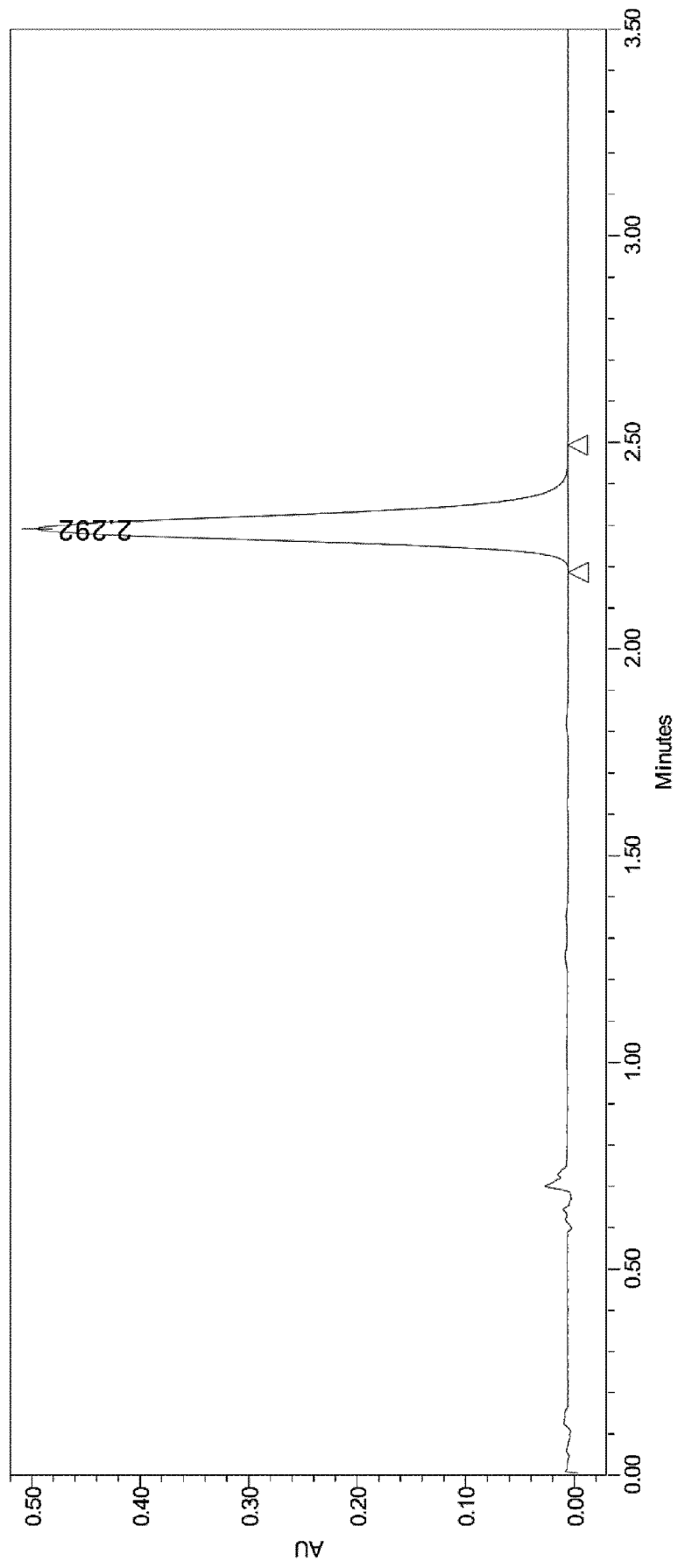
FIG. 2c: Chiral SFC chromatogram of 7a(+).
Figure 3A:
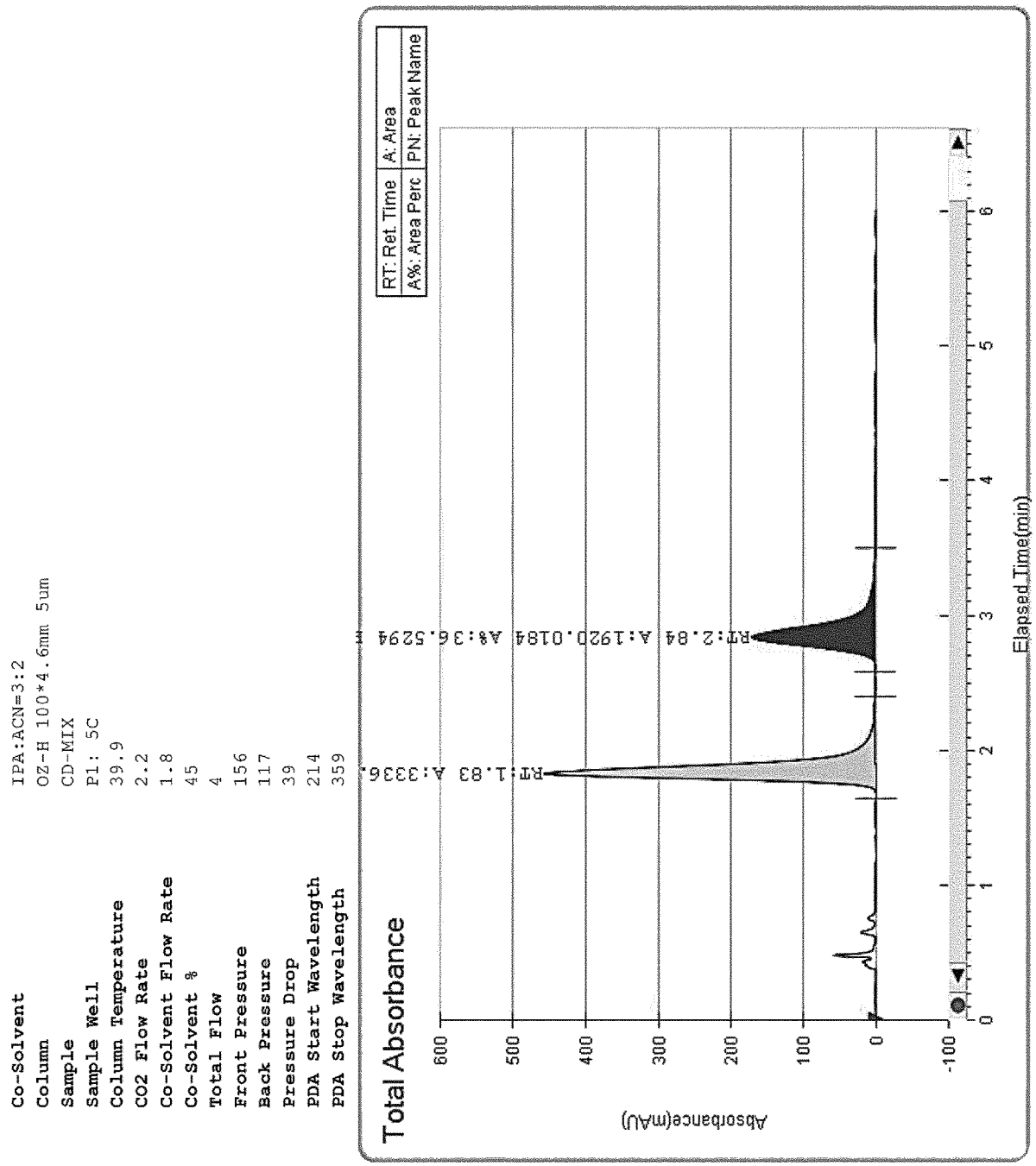
FIG. 3a: Chiral SFC chromatogram of a mixture of 7b(−) and 7b(+).
Figure 3B:
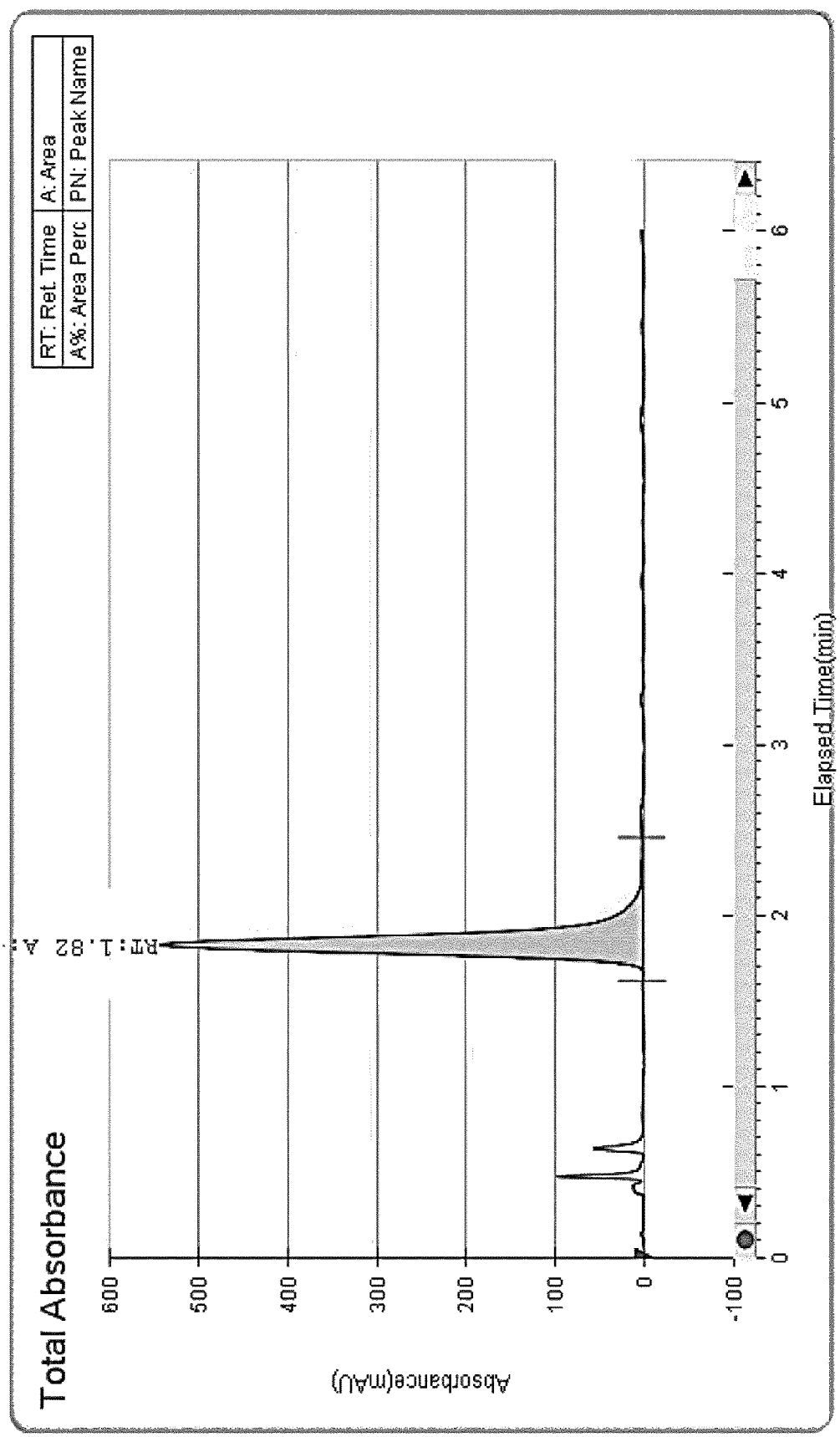
FIG. 3b: Chiral SFC chromatogram of 7b(−).
Figure 3C:
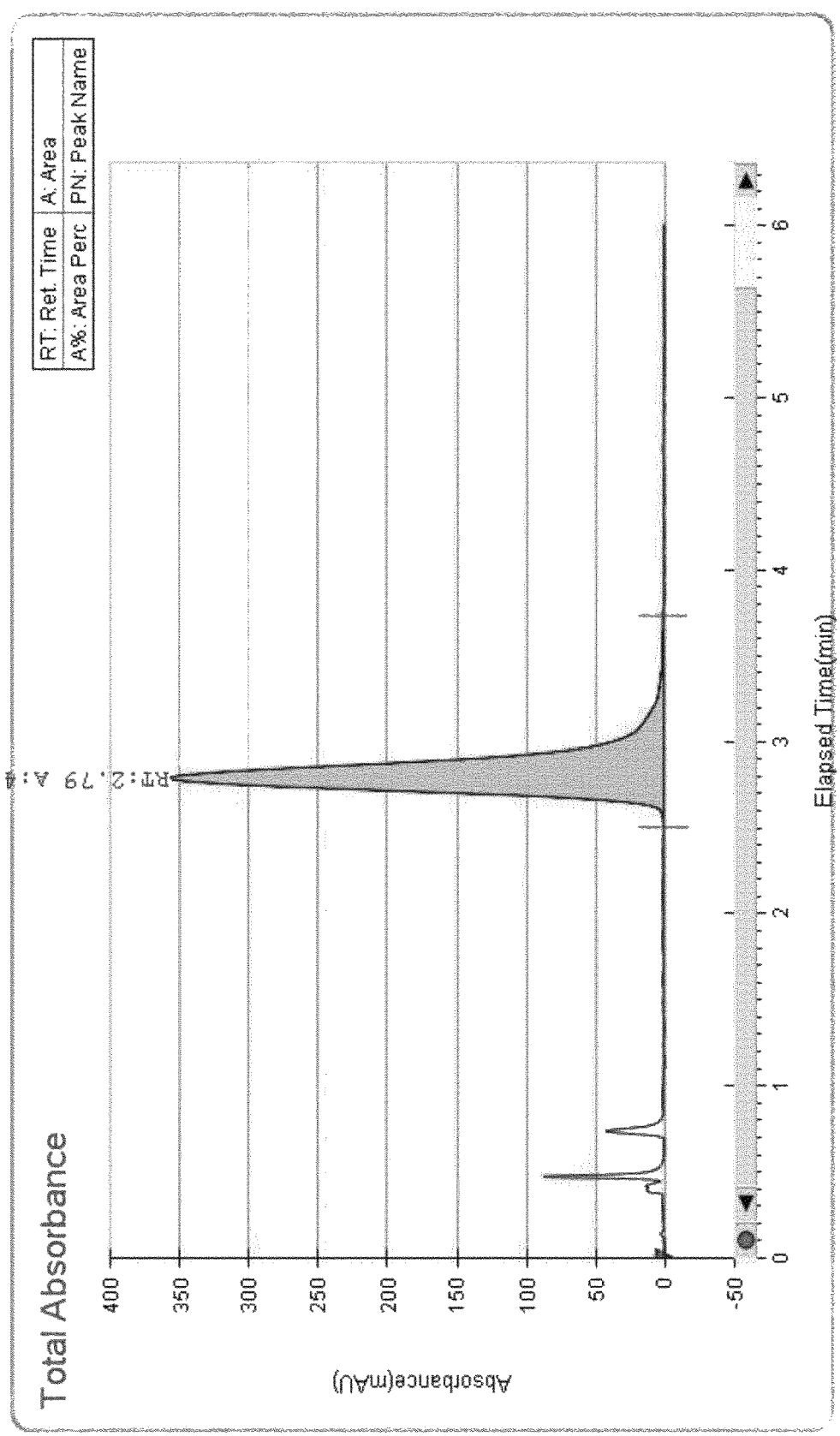
FIG. 3c: Chiral SFC chromatogram of 7b(+).
Figure 4A:
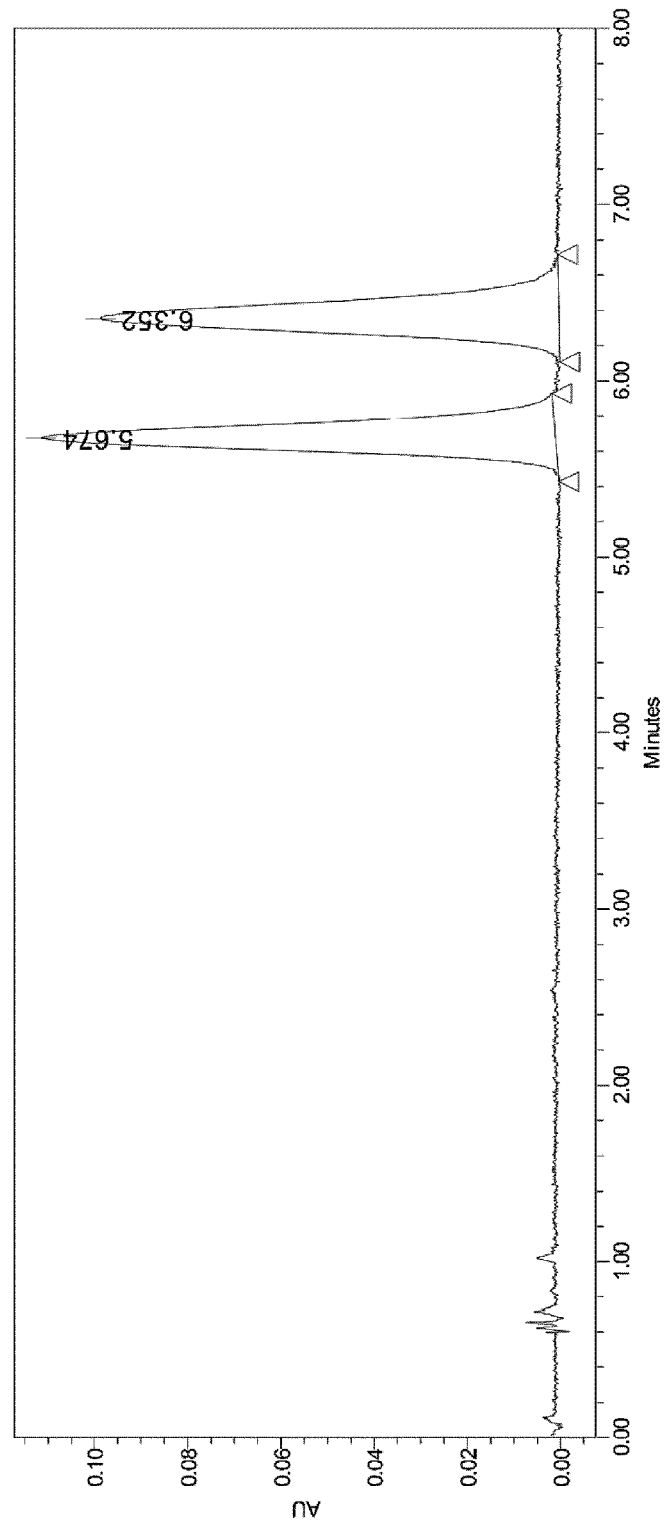
FIG. 4a: Chiral SFC chromatogram of a mixture of 7c(−) and 7c(+).
Figure 4B:
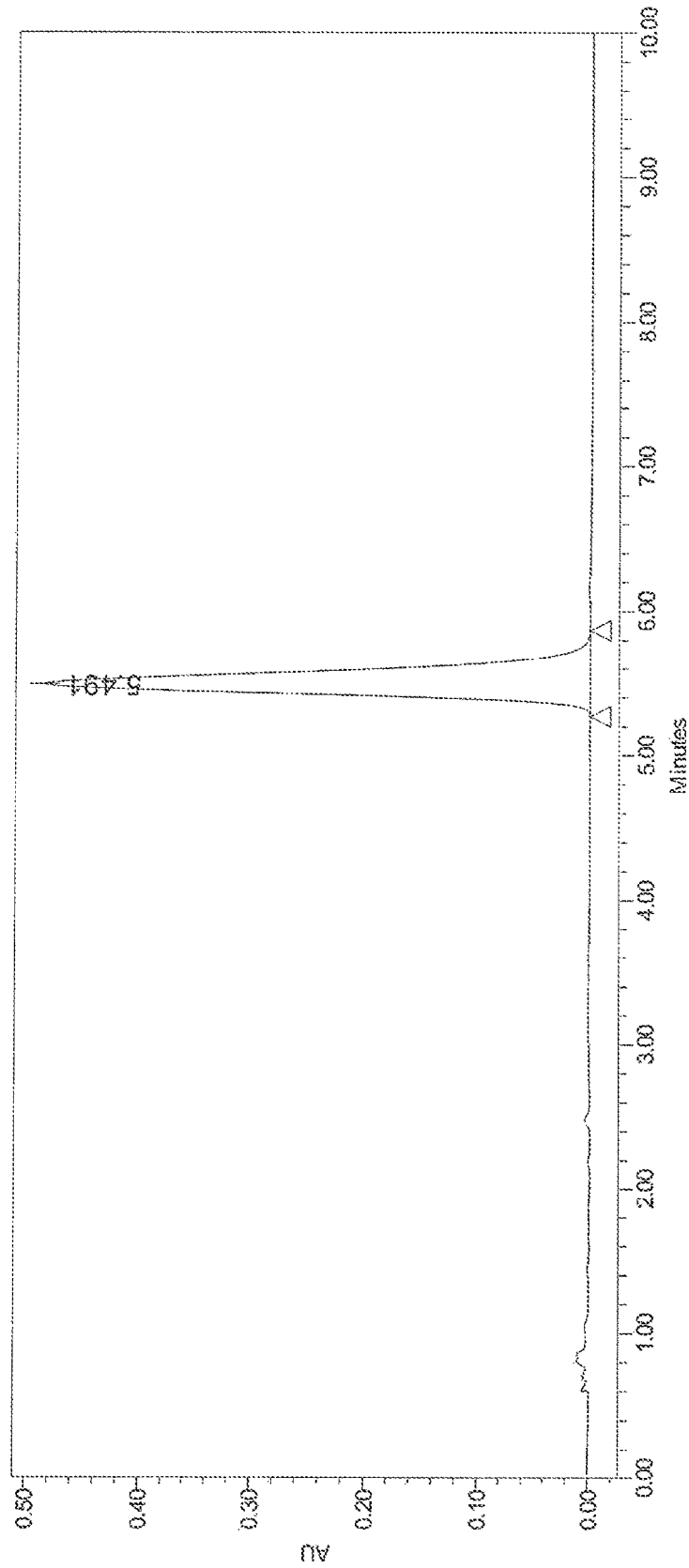
FIG. 4b: Chiral SFC chromatogram of 7c(−).
Figure 4C:
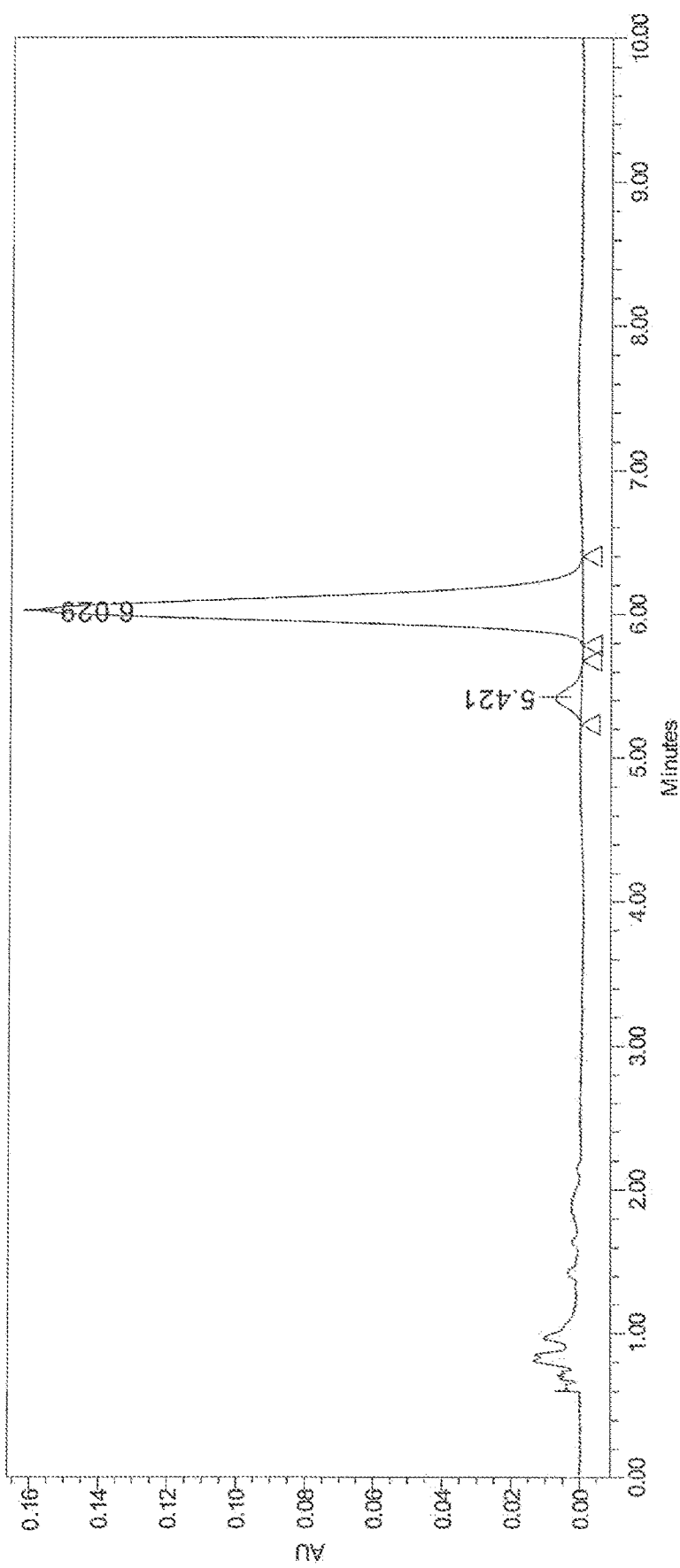
FIG. 4c: Chiral SFC chromatogram of 7c(+).
Figure 5:
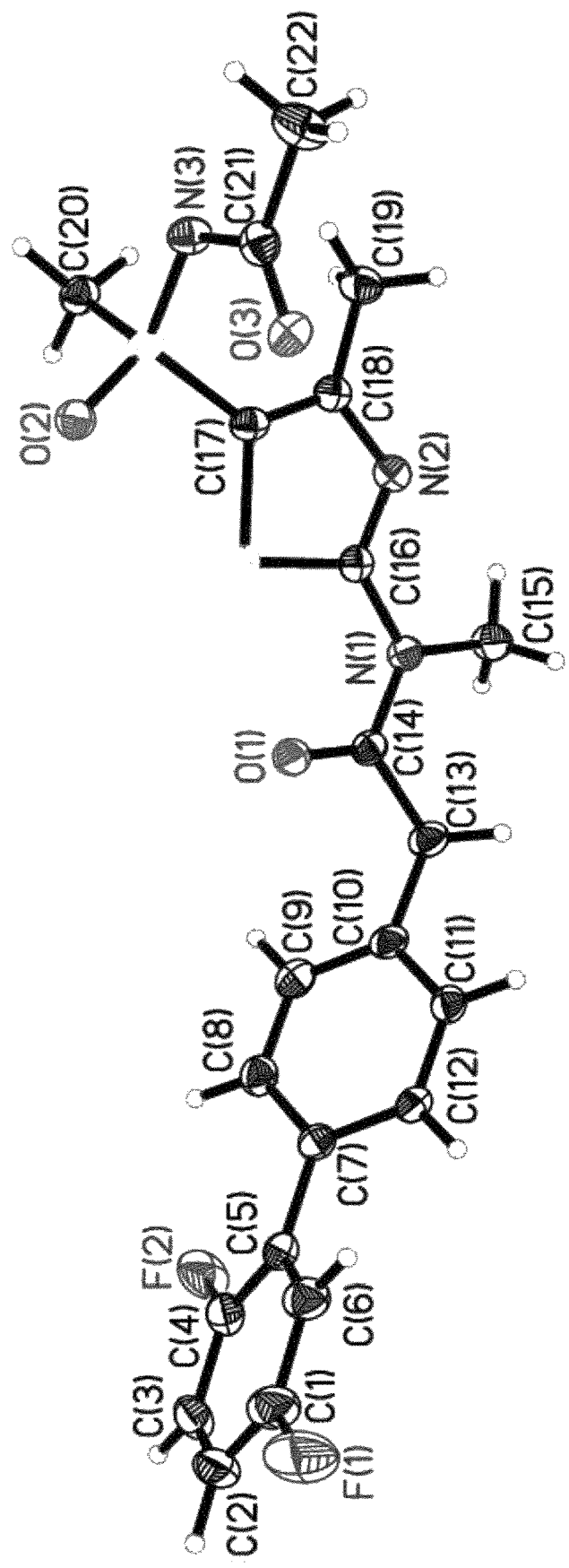
FIG. 5: Ortep-Plot (50%) of Example 8 with labeling scheme.
Figure 6A:
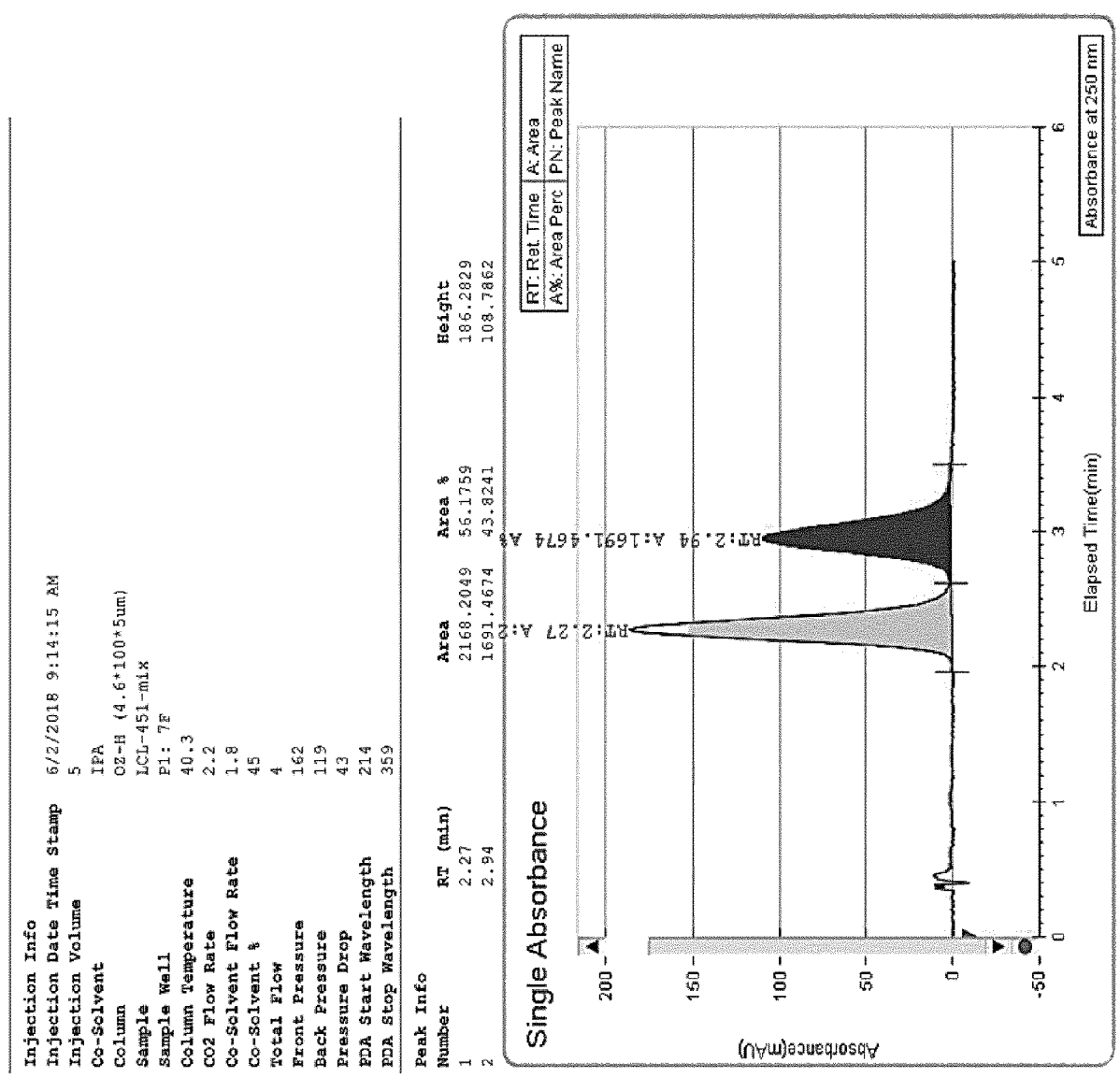
FIG. 6a: Chiral SFC chromatogram of a mixture of 10a and 10b.
Figure 6B:
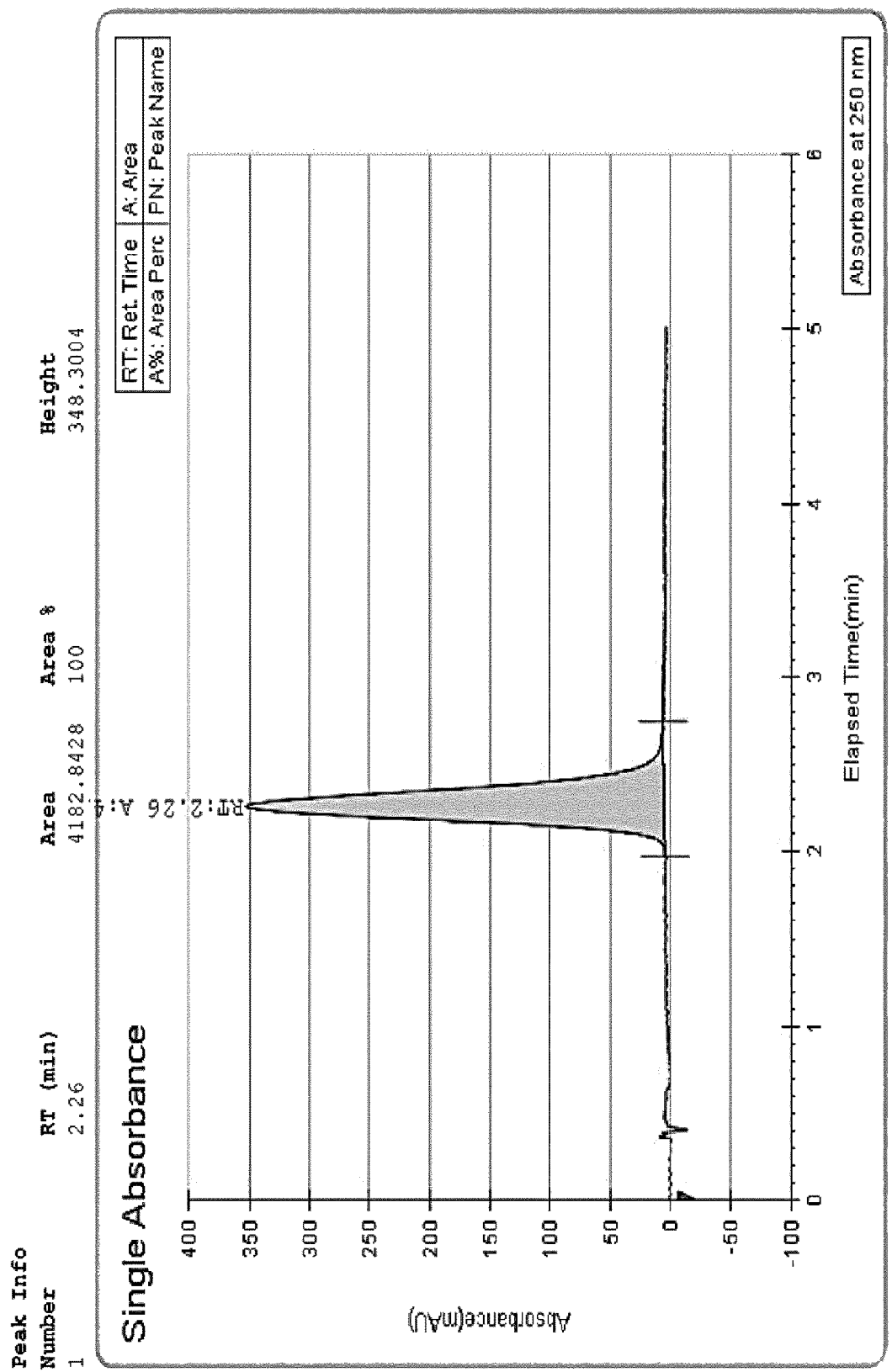
FIG. 6b: Chiral SFC chromatogram of 10a (first eluting isomer).
Figure 6C:
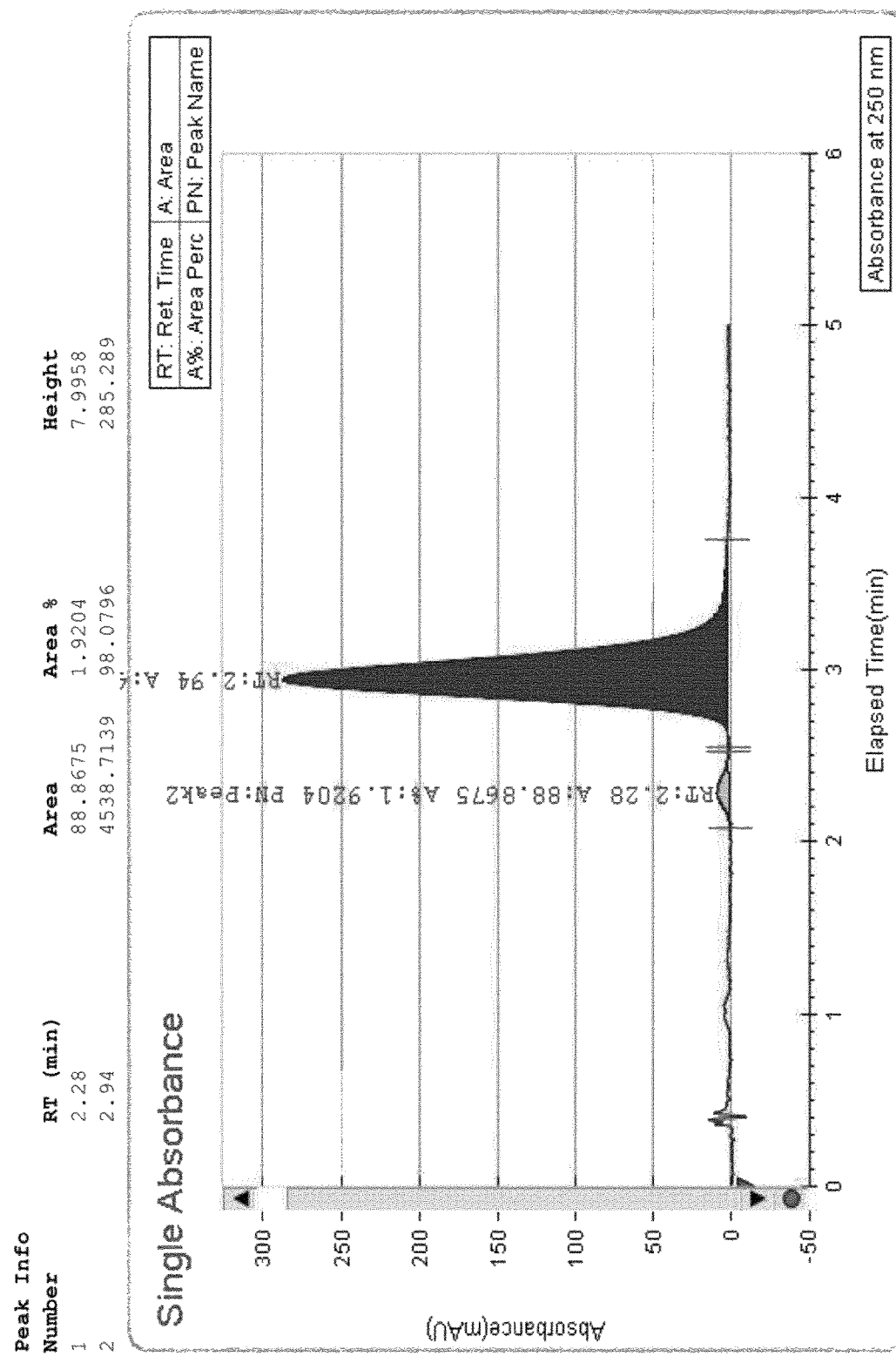
FIG. 6c: Chiral SFC chromatogram of 10b (second eluting isomer).

```
<160> NUMBER OF SEQ ID NOS: 3

<210> SEQ ID NO 1
<211> LENGTH: 18
<212> TYPE: DNA
<213> ORGANISM: herpes simplex virus 7

<400> SEQUENCE: 1
atgagccgcg acaggaac                                                 18

<210> SEQ ID NO 2
<211> LENGTH: 20
<212> TYPE: DNA
<213> ORGANISM: herpes simplex virus 7

<400> SEQUENCE: 2
ggtggatgat taacgccctg                                               20

<210> SEQ ID NO 3
<211> LENGTH: 20
<212> TYPE: DNA
<213> ORGANISM: herpes simplex virus 7

<400> SEQUENCE: 3
ttaacgccct gtaccacacc                                               20
```

The invention claimed is:

1. Compounds according to the Formula (Ia) and/or (Ib):

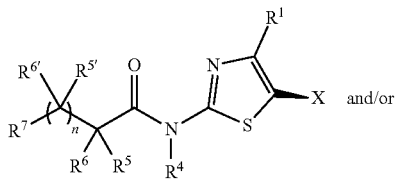

(Ia)

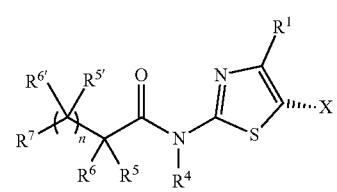

(Ib)

wherein
X is selected from

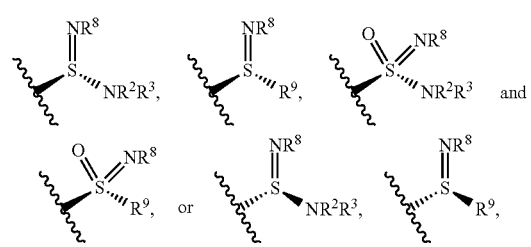

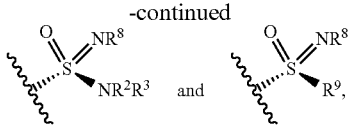

respectively;

$R^1$ is selected from H, halogen, $C_{1-6}$-alkyl, halo-$C_{1-6}$alkyl, hydroxy-$C_{1-6}$-alkyl, $C_{3-6}$-cycloalkyl, halo-$C_{3-6}$-cycloalkyl, —O—$C_{1-6}$-alkyl, —O-halo-$C_{1-6}$-alkyl and —NH—$C_{1-6}$-alkyl;

$R^2$ is selected from H, —CN, —NO$_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$R$^{13}$, $C_{0-10}$-alkylene-SO$_3$R$^{11}$, $C_{0-10}$-alkylene-SO$_2$NR$^{11}$R$^{12}$, $C_{0-10}$-alkylene-NR$^{11}$C(=O)R$^{11}$, $C_{0-10}$-alkylene-NR$^{11}$C(=S)R$^{11}$, $C_{0-10}$-alkylene-NR$^{11}$SO$_2$R$^{13}$, $C_{0-10}$-alkylene-NR$^{11}$C(=O)NR$^{11}$R$^{12}$, $C_{0-10}$-alkylene-NR$^{11}$C(=S)NR$^{11}$R$^{12}$, $C_{0-10}$-alkylene-NR$^{11}$SO$_2$NR$^{11}$R$^{12}$, $C_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, $NR^{11}SO_2R^{13}$, $NR^{11}C(=O)NR^{11}R^{12}$, $NR^{11}SO_2NR^{11}R^{12}$, $C_{3-10}$-cycloalkyl, $O-C_{3-10}$-cycloalkyl, $C_{3-10}$-heterocycloalkyl, $O-C_{3-10}$-heterocycloalkyl and $NR^{11}R^{12}$;

$R^3$ is selected from H, $C_{1-6}$alkyl, halo-$C_{1-6}$-alkyl, $-O-C_{1-6}$alkyl, $-O$-halo-$C_{1-6}$alkyl, $C_{3-6}$-cycloalkyl and $C_{3-6}$-heterocycloalkyl, wherein alkyl, cycloalkyl and heterocycloalkyl are optionally substituted with 1 to 5 substituents independently selected from halogen, $-CN$, OH, oxo, $C_{1-3}$alkyl, halo-$C_{1-3}$-alkyl, $O-C_{1-3}$-alkyl, O-halo-$C_{1-3}$-alkyl, $SO_2$-$C_{1-3}$-alkyl, $CO_2H$;

or $R^2$ and $R^3$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, $-CN$, $-NO_2$, OH, oxo, $C_{1-3}$-alkyl, halo-$C_{1-3}$-alkyl, $O-C_{1-3}$-alkyl, O-halo-$C_{1-3}$-alkyl, $SO_2$-$C_{1-3}$-alkyl, $CO_2H$;

$R^4$ is selected from H, $C_{1-6}$-alkyl, $C_{1-6}$-acyl, $C_{2-6}$-alkenyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, $-CN$, OH, oxo, $C_{1-3}$-alkyl, halo-$C_{1-3}$-alkyl, $O-C_{1-3}$-alkyl, O-halo-$C_{1-3}$-alkyl;

$R^5$ and $R^6$ and $R^{5'}$ and $R^{6'}$ are independently selected from H, halogen, $C_{1-6}$-alkyl, $NH_2$, $NHC_{1-6}$-alkyl, $N(C_{1-6}$-alkyl$)_2$, $C_{0-6}$-alkylene-$C(=O)NH_2$;

or $R^5$ and $R^6$ and $R^{5'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, $-CN$, $-NO_2$, OH, oxo, $C_{1-3}$-alkyl, halo-$C_{1-3}$-alkyl, $O-C_{1-3}$-alkyl, O-halo-$C_{1-3}$-alkyl, $SO_2-C_{1-3}$-alkyl, $CO_2H$;

or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, $-CN$, $-NO_2$, OH, oxo, $C_{1-3}$-alkyl, halo-$C_{1-3}$-alkyl, $O-C_{1-3}$-alkyl, O-halo-$C_{1-3}$-alkyl, $SO_2-C_{1-3}$-alkyl, $CO_2H$;

$R^7$ is selected from a 6-membered aryl and 5- or 6-membered heteroaryl, wherein aryl and heteroaryl are optionally substituted with 1 to 4 substituents independently selected from halogen, $-CN$, $-NO_2$, OH, $C_{1-6}$-alkyl, $O-C_{1-6}$-alkyl, $C_{3-6}$-cycloalkyl, $O-C_{3-6}$-cycloalkyl, $C_{3-6}$-heterocycloalkyl, $O-C_{3-6}$-heterocycloalkyl, $SO_y-C_{1-6}$-alkyl, $CO_2H$, $C(=O)O-C_{1-6}$-alkyl, 6- to 10-membered aryl, 5- or 10-membered heteroaryl, O-(6- to 10-membered aryl) and O-(5- or 10-membered heteroaryl), wherein
alkyl, cycloalkyl, heterocycloalkyl, aryl and heteroaryl are optionally substituted from halogen, $-CN$, $-NO_2$, OH, $R^{13}$, $OR^{13}$, $CO_2R^{11}$, $NR^{11}R^{12}$, $C(=O)R^{11}$, $C(=S)R^{11}$, $C(=O)NR^{11}R^{12}$, $NR^{11}C(=O)R^{12}$, $NR^{11}C(=O)OR^{13}$, $OC(=O)NR^{11}R^{12}$, $C(=S)NR^{11}R^{12}$, $NR^{11}C(=S)NR^{11}R^{12}$, $NR^{11}C(=S)OR^{13}$, $OC(=S)NR^{11}R^{12}$; $SO_y-C_{1-6}$-alkyl, $SO_y$-halo-$C_{1-6}$-alkyl, $SR^{11}$, $SO_xR^{13}$, $SO_3R^{11}$, $SO_2NR^{11}R^{12}$, $NR^{11}SO_2R^{13}$, $NR^{11}SO_2NR^{11}R^{12}$;

$R^8$ is selected from H, $-CN$, $-NO_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5 to 10-membered heteroaryl), $C_{0-10}$-alkylene-(6 to 10-membered aryl), $C_{0-10}$-alkylene-(6 to 10-membered heteroaryl), $C_{0-10}$-alkylene-$OR^{11}$, $C_{0-10}$-alkylene-$CO_2R^{11}$, $C_{0-10}$-alkylene-$C(=O)NR^{11}R^{12}$, $C_{0-10}$-alkylene-$C(=S)NR^{11}R^{12}$, $C_{0-10}$-alkylene-$C(=O)NR^{11}SO_2R^{13}$, $C_{0-10}$-alkylene-$C(=S)NR^{11}SO_2R^{11}$, $C_{0-10}$-alkylene-$C(=O)R^{11}$, $C_{0-10}$-alkylene-$C(=S)R^{11}$, $C_{0-10}$-alkylene-$SR^{11}$, $C_{0-10}$-alkylene-$SO_x-R^{13}$, $C_{0-10}$-alkylene-$SO_3R^{11}$, $C_{0-10}$-alkylene-$SO_2NR^{11}R^{12}$, $C_{0-10}$-alkylene-$NR^{11}C(=O)R^{11}$, $C_{0-10}$-alkylene-$NR^1C(=S)R^{11}$, $C_{0-10}$-alkylene-$NR^{11}SO_2R^{11}$, $C_{0-10}$-alkylene-$NR^{11}C(=O)NR^{11}R^{12}$, $C_{0-10}$-alkylene-$NR^{11}C(=S)NR^{11}R^{12}$, $C_{0-10}$-alkylene-$NR^{11}-SO_2-NR^{11}R^{12}$, $C_{0-10}$-alkylene-$NR^{11}R^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $-NO_2$, $OR^{11}$, $O-C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $PO(OH)_2$, $SO_2NR^{11}R^{12}$, $NR^{11}COR^{11}$, $NR^{11}SO_2R^{11}$, $NR^{11}-CO-NR^{11}R^{12}$, $NR^{11}-SO_2-NR^{11}R^{12}$, $C_{3-10}$-cycloalkyl, $O-C_{3-10}$-cycloalkyl, $C_{3-10}$-heterocycloalkyl, $O-C_{3-10}$-heterocycloalkyl and $NR^{11}R^{12}$;

$R^9$ is selected from $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-$OR^{11}$, $C_{0-10}$-alkylene-$CO_2R^{11}$, $C_{0-10}$-alkylene-$C(=O)NR^{11}R^{12}$, $C_{0-10}$-alkylene-$C(=S)NR^{11}R^{12}$, $C_{0-10}$-alkylene-$C(=O)NR^{11}SO_2R^{13}$, $C_{0-10}$-alkylene-$C(=S)NR^{11}SO_2R^{11}$, $C_{0-10}$-alkylene-$C(=O)R^{11}$, $C_{0-10}$-alkylene-$C(=S)R^{11}$, $C_{0-10}$-alkylene-$SR^{11}$, $C_{0-10}$-alkylene-$SO_xR^{13}$, $C_{0-10}$-alkylene-$SO_3R^{11}$, $C_{0-10}$-alkylene-$SO_2NR^{11}R^{12}$, $C_{0-10}$-alkylene-$NR^{11}C(=O)R^{11}$, $C_{0-10}$-alkylene-$NR^{11}C(=S)R^{11}$, $C_{0-10}$-alkylene-$NR^{11}SO_2R^{13}$, $C_{0-10}$-alkylene-$NR^{11}C(=O)NR^{11}R^{12}$, $C_{0-10}$-alkylene-$NR^{11}C(=S)NR^{11}R^{12}$, $C_{0-10}$-alkylene-$NR^{11}SO_2NR^{11}R^{12}$, $C_{0-10}$-alkylene-$NR^{11}R^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $-NO_2$, $OR^{11}$, $O-C_{2-6}$-alkylene-$OR^{11}$, $C_{1-6}$-alkyl, halo-$C_{1-6}$-alkyl, halogen, $CO_2R^{11}$, $C(=O)NR^{11}R^{12}$, $C(=O)NR^{11}SO_2R^{11}$, $C(=O)R^{11}$, $SR^{11}$, $SO_xR^{11}$, $SO_3R^{11}$, $P(=O)(OR^{11})_2$, $SO_2NR^{11}R^{12}$, $NR^{11}C(=O)R^{11}$, $NR^{11}SO_2R^{13}$, $NR^{11}C(=O)NR^{11}R^{12}$, $NR^{11}SO_2NR^{11}R^{12}$, $C_{3-10}$-cycloalkyl, $O-C_{3-10}$-cycloalkyl, $C_{3-10}$-heterocycloalkyl, $O-C_{3-10}$-heterocycloalkyl and $NR^{11}R^{12}$;

$R^{11}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents independently selected from the group consisting of halogen, $-CN$, OH, oxo, $C_{1-3}$-alkyl, halo-$C_{1-3}$-alkyl, $O-C_{1-3}$-alkyl, O-halo-$C_{1-3}$-alkyl, $NH_2$, $NH(C_{1-3}\text{-alkyl})$, $N(C_{1-3}\text{-alkyl})_2$, $C_{3-6}$-heterocycloalkyl, $C_{3-6}$-cycloalkyl, $SO_2$—$NHC_{1-3}$-alkyl, $SO_2$—$N(C_{1-3}\text{-alkyl})_2$ and $SO_2$—$C_{1-3}$-alkyl, wherein cycloalkyl and heterocycloalkyl is unsubstituted or substituted with 1 to 3 substituents independently selected from the group consisting of F, OH, oxo, $CH_3$, $CHF_2$ and $CF_3$;

$R^{12}$ is independently selected from H, $C_{1-6}$-alkyl, halo-$C_{1-6}$-alkyl and $C_{3-6}$-cycloalkyl;

or $R^{11}$ and $R^{12}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —$NO_2$, OH, oxo, $C_{1-3}$-alkyl, halo-$C_{1-3}$-alkyl, O—$C_{1-3}$-alkyl, O-halo-$C_{1-3}$-alkyl, $SO_2$—$C_{1-3}$-alkyl, $CO_2H$;

$R^{13}$ is independently selected from $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents independently selected from the group consisting of halogen, —CN, OH, oxo, $C_{1-3}$-alkyl, halo-$C_{1-3}$-alkyl, O—$C_{1-3}$-alkyl, O-halo-$C_{1-3}$-alkyl, $NH_2$, $NH(C_{1-3}\text{-alkyl})$, $N(C_{1-3}\text{-alkyl})_2$, $C_{3-6}$-heterocycloalkyl, $C_{3-6}$-cycloalkyl, $SO_2$—$NHC_{1-3}$-alkyl, $SO_2$—$N(C_{1-3}\text{-alkyl})_2$ and $SO_2$—$C_{1-3}$-alkyl, wherein cycloalkyl and heterocycloalkyl is unsubstituted or substituted with 1 to 3 substituents independently selected from the group consisting of F, OH, oxo, $CH_3$, $CHF_2$ and $CF_3$;

n is selected from 0 and 1;

x is independently selected from 1 and 2;

y is independently selected from 0, 1 and 2;

and wherein optionally $R^1$ is connected to one residue selected from $R^2$, $R^3$, $R^8$, $R^9$, $R^{10}$ or $R^{12}$ to form a 5 to 8-membered heterocycle, which is optionally substituted with 1 to 4 substituents independently selected from the group consisting of halogen, —CN, —$NO_2$, OH, oxo, $C_{1-3}$-alkyl, halo-$C_{1-3}$-alkyl, O—$C_{1-3}$-alkyl, O-halo-$C_{1-3}$-alkyl, $SO_2$—$C_{1-3}$-alkyl, $CO_2H$;

or a tautomer, N-oxide, solvate, formulation and pharmaceutically acceptable salt thereof.

2. The compounds according to claim 1, wherein X is selected from

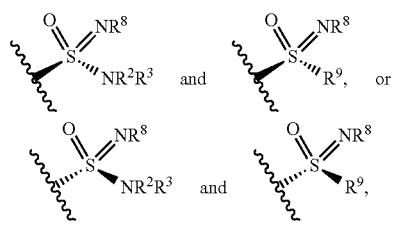

respectively.

3. The compounds according to claim 1, wherein n is 0.

4. The compounds according to claim 1, which are represented by the formula

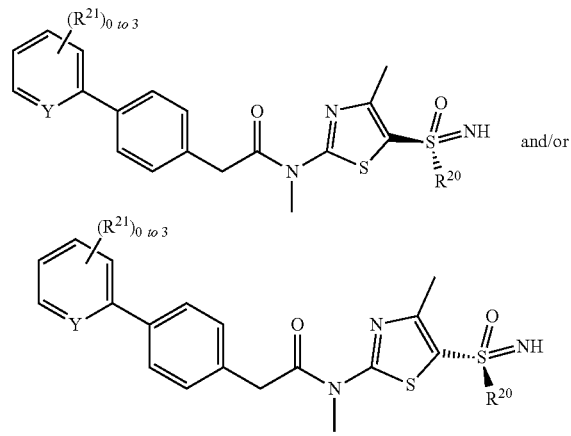

wherein $R^{20}$ is selected from $C_{1-4}$-alkyl and $C_{3-6}$-cycloalkyl, wherein alkyl and cycloalkyl is unsubstituted or substituted with 1 to 3 substituents independently selected from the group consisting of F or Me;

$R^{21}$ is selected from F, Cl, OH, Me, OMe, $CHF_2$, $CF_3$, $OCHF_2$, $OCF_3$; and Y is selected from nitrogen or carbon.

5. The compounds according to claim 1, which are selected from the group consisting of

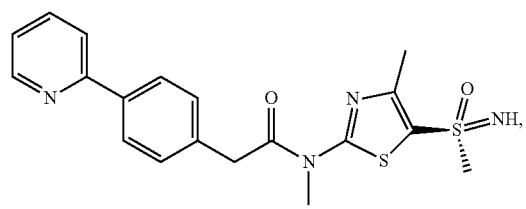

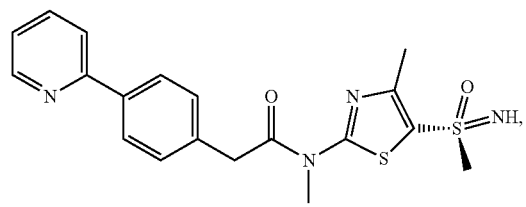

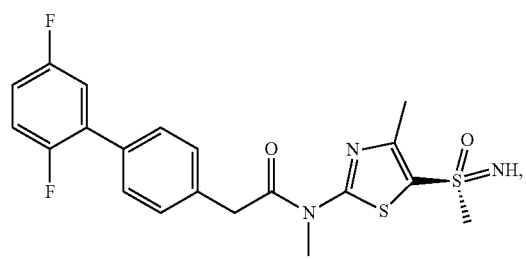

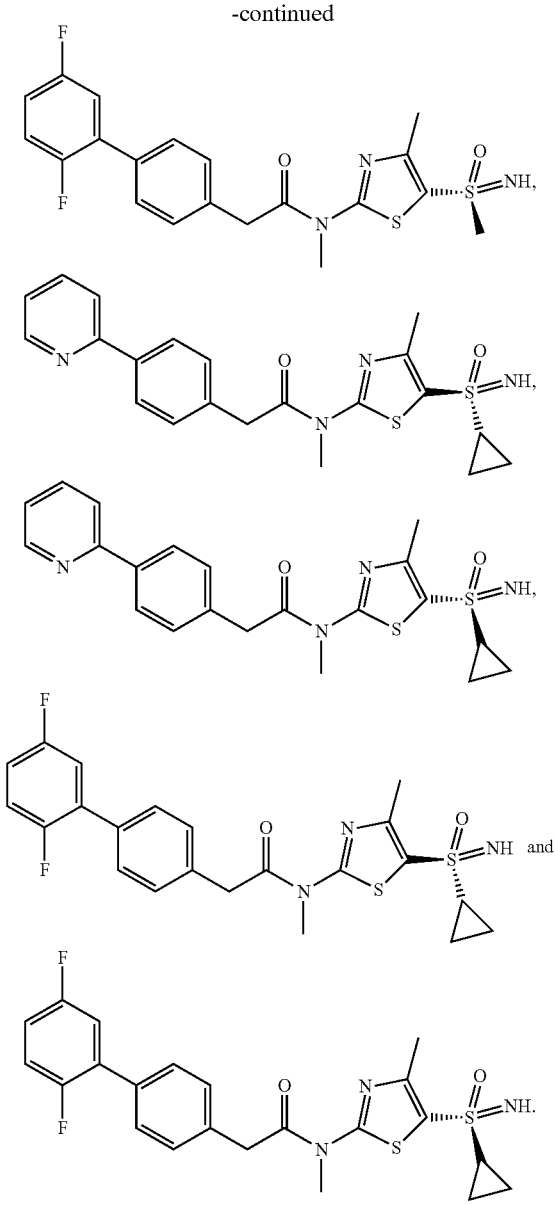

6. The compounds according to claim 1, which are selected from
- (−)-N-Methyl-N-(4-methyl-5-(S-methylsulfonimidoyl)thiazol-2-yl)-2-(4-(pyridin-2-yl)phenyl)acetamide,
- (−)-(S)-2-(2',5'-Difluoro-[1,1'-biphenyl]-4-yl)-N-methyl-N-(4-methyl-5-(S-methylsulfonimidoyl)thiazol-2-yl)acetamide,
- (−)-N-(5-(Cyclopropanesulfonimidoyl)-4-methylthiazol-2-yl)-N-methyl-2-(4-(pyridin-2-yl)phenyl)acetamide, and
- (−)-N-(5-(Cyclopropanesulfonimidoyl)-4-methylthiazol-2-yl)-2-(2',5'-difluoro-[1,1'-biphenyl]-4-yl)-N-methylacetamide.

7. A process for preparing the compounds according to Formula (Ia) and/or (Ib) according to claim 1, the process comprising the steps
a) providing a mixture comprising the compounds of Formulae (Ia) and (Ib), such mixture being represented by Formula (I):

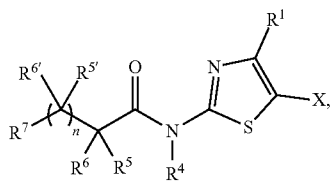

and
b) separating and isolating the compounds of Formulas (Ia) and/or (Ib) using HPLC on a chiral column;
wherein in the Formula (I) the substituents have the meaning as defined in claim 1.

8. The process according to claim 7, wherein Formula (Ia) and/or (Ib) is selected from

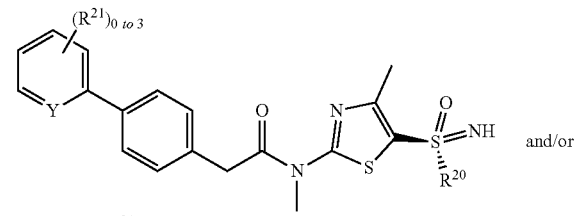

and/or

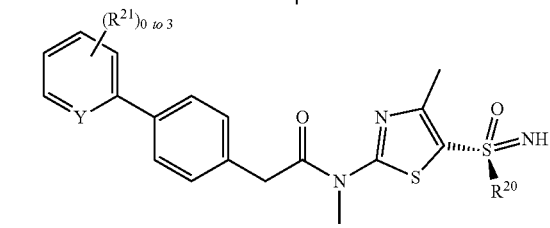

and in step b the separation on a chiral column affords pure (−)-enantiomer.

9. A process for preparing the compounds according to Formula (Ia) and/or (Ib) according to claim 1 by stereoselective synthesis and optionally subsequent preparative HPLC on a chiral column or precipitation with chiral compounds.

10. A method of treating or preventing a condition, disease or disorder associated with herpes virus infection comprising, administering to a human or animal in need thereof, a composition comprising at least one compound according to claim 1.

11. The method according to claim 10, wherein the herpes virus infection comprises herpes simplex viral infection.

12. The method according to claim 10, wherein the herpes virus infection is at least one selected from the group consisting of: herpes labialis, herpes genitalis and herpes-related keratitis.

13. The method according to claim 10,
wherein the human or animal in need thereof is suffering from:
(a) Alzheimer's disease, encephalitis, pneumonia, hepatitis and viral shedding; or
(b) a suppressed immune system, AIDS, cancer, genetic or inherited immunodeficiency, or
(c) the human or animal in need thereof is a transplant patient.

14. The method of claim 10, wherein the human or animal in need thereof is resistant to nucleosidic antivirals selected from the group consisting of acyclovir, penciclovir, famciclovir, ganciclovir, valacyclovir and/or foscarnet or cidofovir.

15. The method according to claim 10, wherein the human in need thereof is selected from the group consisting of new-born children and infants.

16. The method according to claim 10,
   wherein the condition, disease or disorder is viral shedding related to suppression therapy.

17. A method of treating or preventing a condition, disease or disorder associated with herpes virus infection caused by wild type or genetically engineered viruses comprising, administering to a human or animal in need thereof, a composition comprising at least one compound according to claim 1.

18. A method of treating or preventing a neurodegenerative disease caused by herpes viruses comprising, administering to a human or animal in need thereof a composition comprising at least one compound according to claim 1.

19. A method of treating or preventing a condition, disease or disorder associated herpes virus infections comprising, administering to a human or animal in need thereof, a pharmaceutical composition comprising one or more of the compounds according to claim 1, and at least one pharmaceutically acceptable carrier and/or excipient and/or at least one further active substance selected from the group consisting of antiviral active compounds and immune modulating compounds.

* * * * *